US012331062B2

(12) United States Patent
Ie et al.

(10) Patent No.: US 12,331,062 B2
(45) Date of Patent: Jun. 17, 2025

(54) COMPOUND, PRODUCTION METHOD THEREFOR, AND ORGANIC SEMICONDUCTOR MATERIAL OBTAINED USING SAID COMPOUND

(71) Applicants: Osaka University, Osaka (JP); ISHIHARA SANGYO KAISHA, LTD., Osaka (JP)

(72) Inventors: Yutaka Ie, Osaka (JP); Takuji Seo, Osaka (JP); Shreyam Chatterjee, Osaka (JP); Taichi Moriyama, Osaka (JP); Syun Kudo, Osaka (JP)

(73) Assignees: Osaka University, Osaka (JP); ISHIHARA SANGYO KAISHA, LTD., Osaka (JP)

( * ) Notice: Subject to any disclaimer, the term of this patent is extended or adjusted under 35 U.S.C. 154(b) by 1056 days.

(21) Appl. No.: 17/288,949

(22) PCT Filed: Oct. 25, 2019

(86) PCT No.: PCT/JP2019/041840
§ 371 (c)(1),
(2) Date: Apr. 27, 2021

(87) PCT Pub. No.: WO2020/090636
PCT Pub. Date: May 7, 2020

(65) Prior Publication Data

US 2021/0399228 A1 Dec. 23, 2021

(30) Foreign Application Priority Data

Oct. 30, 2018 (JP) ................................ 2018-203735

(51) Int. Cl.
*C07D 513/22* (2006.01)
*C07D 495/22* (2006.01)
(Continued)

(52) U.S. Cl.
CPC ......... *C07D 513/22* (2013.01); *C07D 495/22* (2013.01); *C07D 498/22* (2013.01); (Continued)

(58) Field of Classification Search
None
See application file for complete search history.

(56) References Cited

U.S. PATENT DOCUMENTS

2012/0227812 A1 9/2012 Quinn et al.
2014/0163188 A1 6/2014 Itaru et al.
(Continued)

FOREIGN PATENT DOCUMENTS

CN 103665343 A 3/2014
CN 103703583 A 4/2014
(Continued)

OTHER PUBLICATIONS

Shin. Journal of the American Chemical Society, 2003, 130, 2062-2068 (Year: 2003).*
(Continued)

*Primary Examiner* — Noble E Jarrell
(74) *Attorney, Agent, or Firm* — McCarter & English, LLP; David G. Conlin

(57) ABSTRACT

Provided are a compound having an excellent semiconductor property and a method for producing the compound, an intermediate of the compound and a method for producing the intermediate, and an organic semiconductor material and an organic semiconductor device each obtained with use of the organic semiconductor material.

A compound represented by general formula (2):

(1)

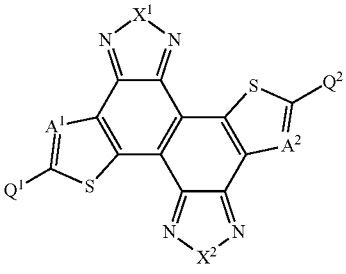

where: $A^1$ and $A^2$ are $CM^1$ or N, and $M^1$ is H or the like; $J^1$ and $J^2$ are each independently a skeleton giving an electron donating property or an electron accepting property; and $X^1$ and $X^2$ are

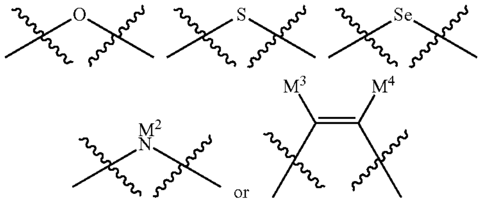

or where: $M^2$ to $M^4$ are H or the like, and $M^3$ and $M^4$ may be bonded to each other to form a ring.

7 Claims, 4 Drawing Sheets

(51) Int. Cl.

| | |
|---|---|
| ***C07D 498/22*** | (2006.01) |
| ***C07D 517/22*** | (2006.01) |
| ***C09K 11/06*** | (2006.01) |
| ***H10K 30/00*** | (2023.01) |
| ***H10K 30/30*** | (2023.01) |
| ***H10K 30/50*** | (2023.01) |
| ***H10K 85/60*** | (2023.01) |
| ***H10K 101/30*** | (2023.01) |

(52) U.S. Cl.

CPC ............ *C07D 517/22* (2013.01); *C09K 11/06* (2013.01); *H10K 85/615* (2023.02); *H10K 85/654* (2023.02); *H10K 85/655* (2023.02); *H10K 85/657* (2023.02); *H10K 85/6572* (2023.02); *H10K 85/6576* (2023.02); *C09K 2211/1018* (2013.01); *H10K 30/00* (2023.02); *H10K 30/30* (2023.02); *H10K 30/50* (2023.02); *H10K 2101/30* (2023.02)

(56) References Cited

U.S. PATENT DOCUMENTS

| | | | |
|---|---|---|---|
| 2015/0112081 | A1 | 4/2015 | Kazuo et al. |
| 2019/0337966 | A1 | 11/2019 | Ie et al. |

FOREIGN PATENT DOCUMENTS

| | | | | |
|---|---|---|---|---|
| CN | 104254538 | A | | 12/2014 |
| JP | 2013-131716 | A | | 7/2013 |
| JP | 2017-066069 | A | | 4/2017 |
| WO | 2015/133471 | A1 | | 9/2015 |
| WO | 2018/123207 | A1 | | 7/2018 |
| WO | WO-2020158256 | A1 | * | 8/2020 |

OTHER PUBLICATIONS

Duvenhage. Physica B, 2014, 439, 46-49 (Year: 2014).*

Taiwan Office Action for Application No. 108138605, dated May 26, 2023, 11 pages.

Chinese Office Action for Application No. 201980071271.7, dated Feb. 11, 2023, 16 pages.

H. Soleiman, "Synthesis of polyfused heterocyclic compounds via reactivity 1, 4-naphthoquinone," Organic Chemistry: An Indian Journal, 2012, 8(8), pp. 307-310.

File Registry on STN, RN 1805797-56-1 (entered STN on Sep. 11, 2015).

International Search Report issued Dec. 10, 2019 in corresponding PCT Application No. PCT/JP2019/041840.

International Preliminary Report on Patentability issued Apr. 27, 2021 in corresponding PCT Application No. PCT/JP2019/041840.

Osaka et al., "Naphthobischalcogenadiazole Conjugated Polymers: Emerging Materials for Organic Electronics," Adv. Mater. 2017, 1605218, pp. 1-20.

* cited by examiner

COMPOUND, PRODUCTION METHOD THEREFOR, AND ORGANIC SEMICONDUCTOR MATERIAL OBTAINED USING SAID COMPOUND

CROSS REFERENCE TO RELATED APPLICATION

The present application is a U.S. National Stage Entry of the International Patent Application No. PCT/JP2019/041840, filed on Oct. 25, 2019, which claims priority to Japanese Application No. 2018-203735, filed on Oct. 30, 2018. The entire contents of those applications are incorporated herein for all purposes by this reference.

TECHNICAL FIELD

The present invention relates to a compound having a semiconductor property, a method for producing the compound, an intermediate of the compound, a method for producing the intermediate, and an organic semiconductor material and an organic semiconductor device each obtained with use of the compound.

BACKGROUND ART

As a compound having a semiconductor property, naphthobisthiadiazole (hereinafter, occasionally referred to as "NTz") is widely used as an organic semiconductor skeleton that is electron-deficient (that has an acceptor property or an n-type semiconductor property), for example. By bonding a π skeleton such as an aromatic ring or a heteroaromatic ring to position 3 or position 7 of the NTz skeleton to extend the conjugated systems, it is possible to achieve various types of materials. It has been reported so far that a compound prepared by incorporating the NTz skeleton into a conjugated system of an oligomer or a polymer by bonding the NTz skeleton to the oligomer or the polymer via a single bond is used for an n-type semiconductor, a p-type semiconductor, or a p-n type semiconductor (see Patent Literature 1 and Non-Patent Literature 1, for example).

CITATION LIST

Patent Literature

Patent Literature 1: Japanese Patent Application Publication Tokukai No. 2013-131716

Non-Patent Literature

Non Patent Literature 1: Itaru Osaka, Kazuo Takimiya, Advanced Materials, 2017, 1605218.

SUMMARY OF INVENTION

Technical Problem

Among compounds each containing the NTz skeleton in its molecular structure, compounds having a favorable semiconductor property have been found. These compounds, however, are still demanded for a further improvement, etc. in the semiconductor property, such as photoelectric conversion efficiency, charge mobility, etc.

An aspect of the present invention has an object to provide a compound having an excellent semiconductor property, a method for producing the compound, an intermediate of the compound, a method for producing the intermediate, and an organic semiconductor material and an organic semiconductor device each obtained with use of the compound.

Solution to Problem

The inventors of the present invention conducted a diligent study on introducing, into a compound including the NTz skeleton in its molecular structure, a condensed ring structure bringing about an improvement in planarity and/or acceptor property. As a result, the inventors of the present invention found that fusing a five-membered heteroaromatic ring, such as a thiophene ring, a thiazole ring, etc., to the NTz skeleton results in excellent planarity and enables extensions of the conjugated systems to improve the acceptor property, thereby providing an excellent semiconductor property. Based on this, the inventors of the present invention completed the present invention.

In order to attain the object, a compound in accordance with a first aspect of the present invention is represented by a general formula (1).

(1)

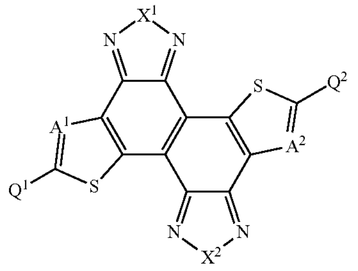

In the general formula (1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

$X^1$ and $X^2$ are each independently

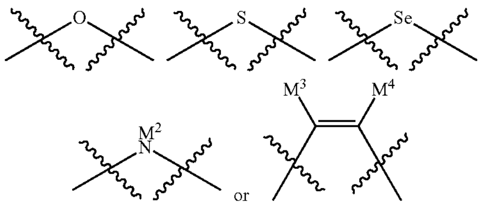

or where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

In addition, the compound in accordance with the first aspect of the present invention may be a compound represented by the above-shown general formula (1), where:

$M^1$ is a hydrogen atom, a halogen atom, an alkyl group optionally substituted with Z, a cyano group, or an alkoxy group optionally substituted with Z; and $M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryl group optionally substituted with Z, or a heterocyclic group optionally substituted with Z, and $M^3$ and $M^4$ are optionally bonded to each other to form a ring in a case where $M^3$ and $M^4$ are an alkyl group or an aryl group.

A compound in accordance with a second aspect of the present invention is represented by a general formula (2).

(2)

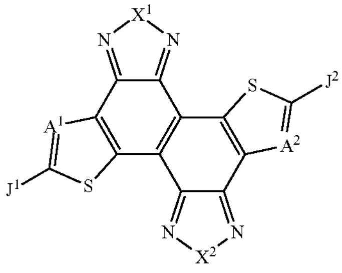

In the general formula (2), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$J^1$ and $J^2$ are each independently a skeleton giving an electron donating property or an electron accepting property;

$X^1$ and $X^2$ are each independently

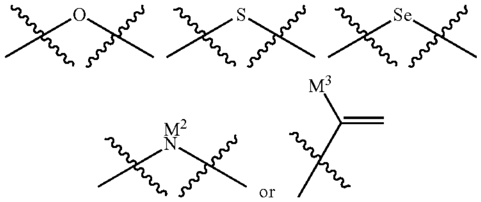

or where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

In addition, the compound in accordance with the second aspect of the present invention may be a compound represented by the above-shown general formula (2), where:

$M^1$ is a hydrogen atom, a halogen atom, an alkyl group optionally substituted with Z, a cyano group, or an alkoxy group optionally substituted with Z; and $M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryl group optionally substituted with Z, or a heterocyclic group optionally substituted with Z, and $M^3$ and $M^4$ are optionally bonded to each other to form a ring in a case where $M^3$ and $M^4$ are an alkyl group or an aryl group.

Advantageous Effects of Invention

A compound in accordance with an aspect of the present invention includes a naphthalene ring having two opposite sides fused with five-membered heteroaromatic rings, and accordingly has excellent planarity. In addition, this compound has a thiophene ring or a thiazole ring at its position α, and therefore the conjugated systems therein can be easily extended. Accordingly, this compound achieves an improved acceptor property, whereby achieves an improved photoelectric conversion efficiency and an improved charge mobility. Thus, this compound possesses an excellent semiconductor property.

In addition, an organic semiconductor material including a compound in accordance with an aspect of the present invention has a high photoelectric conversion efficiency and a high charge mobility, i.e., an excellent semiconductor property, and therefore is applicable to various semiconductor devices, such as photoelectric conversion elements, organic thin-film transistors (e.g., field effect transistors), light emitting devices, etc.

In addition, with a compound in accordance with an aspect of the present invention, it is possible to easily produce various compounds having a semiconductor property.

That is to say, the aspect of the present invention brings about an effect of providing a compound having an excellent semiconductor property, a method for producing the compound, an intermediate of the compound, a method for producing the intermediate, and an organic semiconductor material and an organic semiconductor device each obtained with use of the compound.

DETAILED DESCRIPTION

Figure 1:
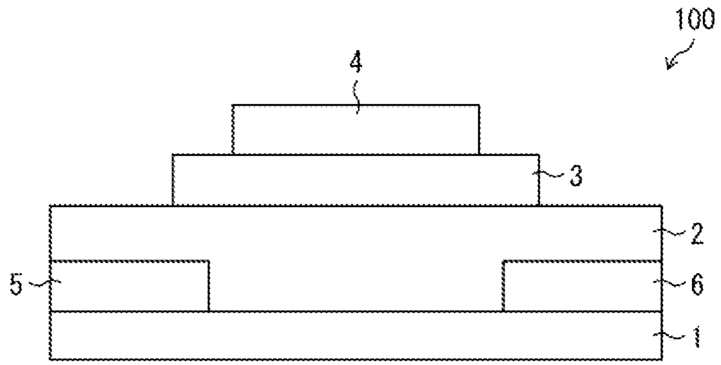
FIG. 1 is a cross-sectional view schematically illustrating an organic thin-film transistor in accordance with Embodiment 1 of the present invention.

The following will provide a detailed description of an embodiment of the present invention.

(Compound Represented by General Formula (1))

A compound in accordance with an aspect of the present invention is represented by a general formula (1).

(1)

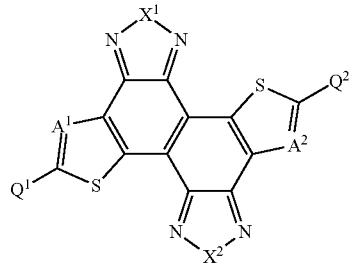

In the general formula (1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

each of $X^1$ and $X^2$ is independently

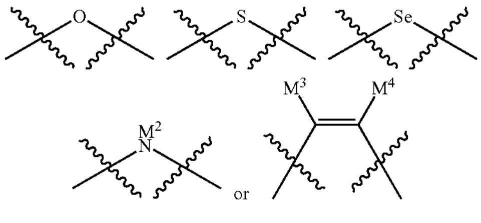

or where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

Examples of the halogen atom encompass fluorine, chlorine, bromine, and iodine (hereinafter, the "halogen atom" means at least one kind selected from fluorine, chlorine, bromine, and iodine, unless otherwise specifically noted).

The alkyl group is preferably $C_{1-30}$, more preferably $C_{6-30}$, and may be in a linear chain form or in a branched chain form. The alkoxy group is preferably $C_{1-30}$, more preferably $C_{1-12}$, and may be in a linear chain form or in a branched chain form. The alkyl ester group is preferably $C_{2-30}$, more preferably $C_{2-12}$, and may be in a linear chain form or in a branched chain form. The alkoxy carbonyl group is preferably $C_{2-30}$, more preferably $C_{2-12}$, and may be in a linear chain form or in a branched chain form. The alkyl amino carbonyl group is preferably $C_{2-40}$, more preferably $C_{2-12}$, and may be in a linear chain form or in a branched chain form. The acyl group is preferably $C_{2-30}$, more preferably $C_{2-12}$, and may be in a linear chain form or in a branched chain form. Examples of the amino group optionally substituted with Z that is an alkyl group encompass, in addition to the amino group, a monoalkylamino group, a dialkylamino group, a trialkylamino group, etc. The alkyl group that is a substituent group substituted for the amino group is preferably $C_{1-30}$, more preferably $C_{1-12}$, and may be in a linear chain form or in a branched chain form. The acylamino group is preferably $C_{2-30}$, more preferably $C_{2-12}$, and may be in a linear chain form or in a branched chain form. Other substituents having an alkyl moiety are each $C_{1-30}$, more preferably $C_{6-30}$, and the alkyl moiety may be in a linear chain form or in a branched chain form. The aryl group or an aryl moiety of each substituent is preferably $C_{6-30}$, more preferably $C_{6-12}$, and particularly preferably a phenyl group. The cycloalkyl group or a cycloalkyl moiety of each substituent is preferably $C_{3-40}$, more preferably $C_{4-20}$. The heterocyclic group is preferably $C_{3-30}$, more preferably $C_{3-12}$, and particularly preferably a thienyl group.

The compound (intermediate) represented by the general formula (1) (hereinafter, such a compound will be referred to as "compound (1)") has rigidity and high planarity. Accordingly, a compound (2), represented by the later-shown general formula (2), synthesized from the above compound serving as the intermediate has rigidity and high planarity. Thus, in a case where the compound (2) is employed as an organic semiconductor material and formed into a film, an organic semiconductor layer (semiconductor active layer) obtained as the film achieves a short intermolecular distance, thereby exhibiting a high charge mobility.

In addition, since the compound (1) has a thiophene ring or a thiazole ring in its a position, and therefore the conjugated systems therein can be easily extended. The derivative thereof, that is, the compound represented by the general formula (1) in which each of $Q^1$ or $Q^2$ is a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group can be easily developed into the compound represented by the general formula (2), etc. by extending the conjugated systems in the manner described later.

(Compound Represented by General Formula (2))

A compound in accordance with an aspect of the present invention has a structure that includes a skeleton represented by the general formula (2) and that corresponds to the compound (1) into which a skeleton giving an electron donating property (donor property) or an electron accepting property (acceptor property) is introduced. Alternatively, the compound in accordance with the aspect may have a repeating unit of the skeleton represented by the compound (1).

(2)

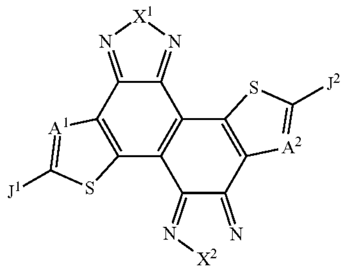

In the general formula (2), $A^1$, $A^2$, $X^1$, and $X^2$ are the same as those defined above;

$J^1$ and $J^2$ are each independently a skeleton giving an electron donating property or an electron accepting property and may be a known skeleton selected as appropriate.

Specifically, the compound represented by the general formula (2) (hereinafter, referred to as a "compound (2)") is preferably a compound represented by a general formula (2-1).

(2-1)

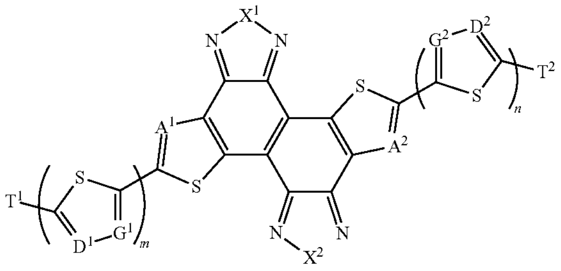

In the general formula (2-1), $A^1$, $A^2$, $X^1$, and $X^2$ are the same as those defined above;

$D^1$, $D^2$, $G^1$, and $G^2$ are each independently $CM^1$ or N, and $M^1$ is the same as that defined above;

m and n are each independently 0 or a natural number; and $T^1$ and $T^2$ are each independently a cyclic functional group including an alkenylene group. For example, each of $T^1$ and $T^2$ is preferably a functional group having any of the structures shown below. $R^1$ to $R^9$ are each independently a hydrogen atom, a halogen atom, an alkyl group, an alkoxy group, an alkoxy carbonyl group, an alkyl carbonyl group, or an aryl group. An alkyl moiety of the alkyl group, the alkoxy group, the alkoxy carbonyl group, or the alkyl carbonyl group selected as $R^1$ to $R^9$ may be in a linear chain form or in a branched chain form, and is preferably $C_{6-30}$, more preferably $C_{8-24}$. The aryl group is preferably a phenyl group, a naphthyl group, or an adamantyl group, for example. Note that * in the structures shown below is a bond.

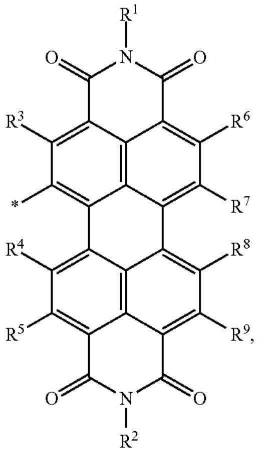

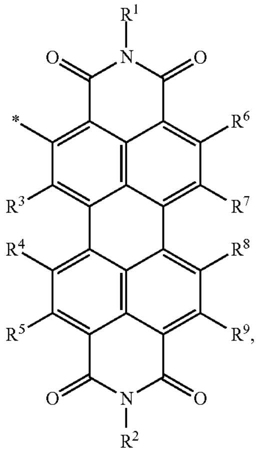

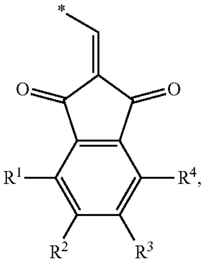

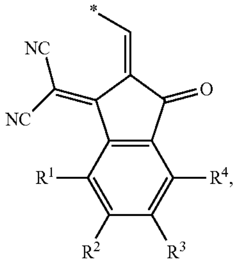

-continued

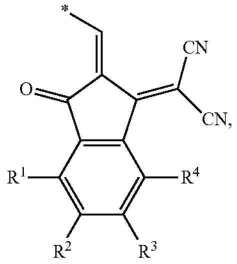

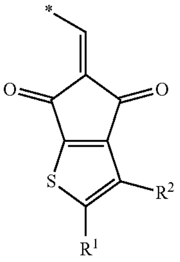

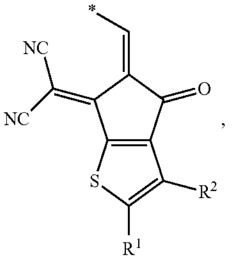

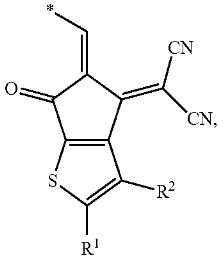

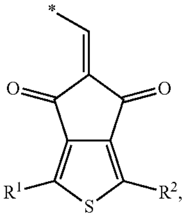

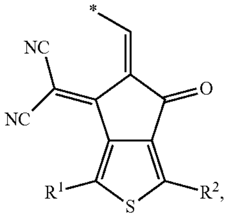

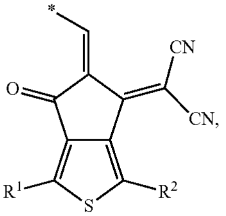

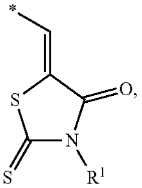

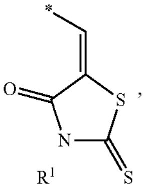

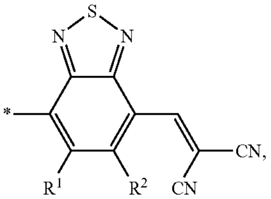

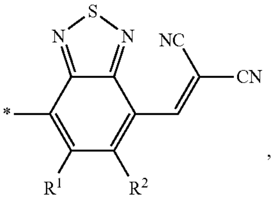

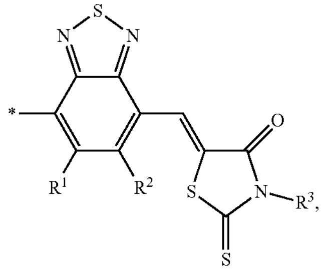

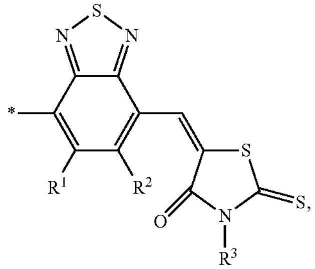

-continued

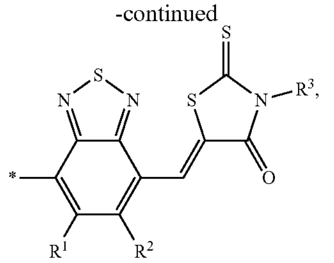

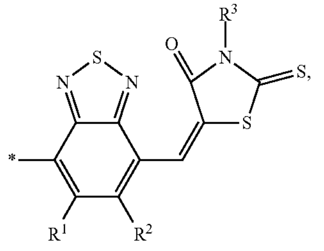

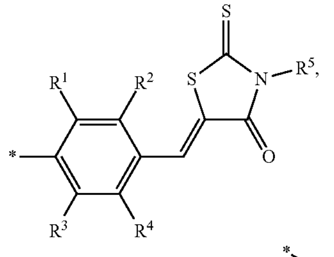

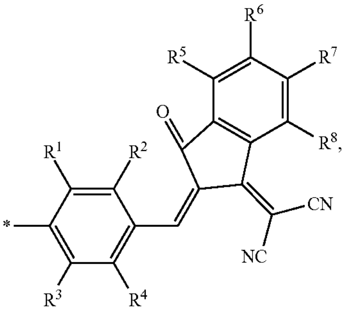

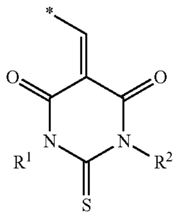

or

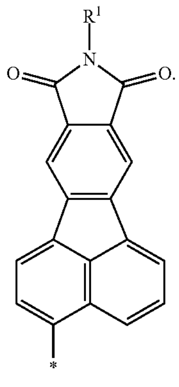

More preferably, the compound represented by the general formula (2-1) is a compound represented by a general formula (2-2).

(2-2)

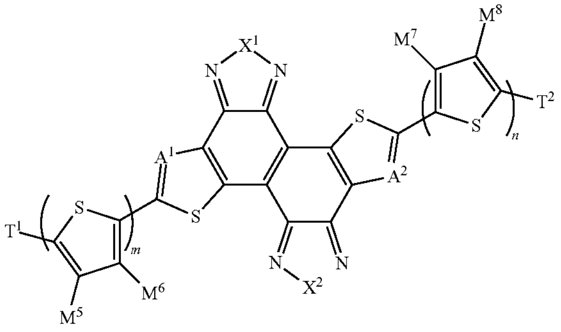

In the general formula (2-2), $A^1$, $A^2$, $T^1$, $T^2$, $X^1$, $X^2$, m, and n are the same as those defined above;

$M^5$ to $M^8$ are each independently a hydrogen atom, a halogen atom, an alkyl group, an alkoxy group, an alkoxy carbonyl group, an alkyl carbonyl group, or an aryl group.

An alkyl moiety of the alkyl group, the alkoxy group, the alkoxy carbonyl group, or the alkyl carbonyl group selected as $M^5$ to $M^8$ may be in a linear chain form or in a branched chain form, and is preferably $C_{6-30}$, more preferably $C_{8-24}$. The aryl group is preferably a phenyl group, a naphthyl group, or an adamantyl group, for example.

(Method 1 for Producing Compound (1))

A method for producing the above-described compound (1) (intermediate) is not limited to any particular one. For example, it is possible to synthesize a compound represented by the general formula (A1) shown below from a commercially-available compound to produce naphthobisthiadiazole fused with a thiophene ring. Preferable steps will be described in accordance with the reaction scheme shown below. A more specific example will be described in the later-described Examples.

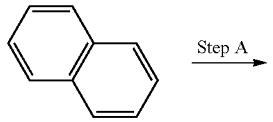

(I)

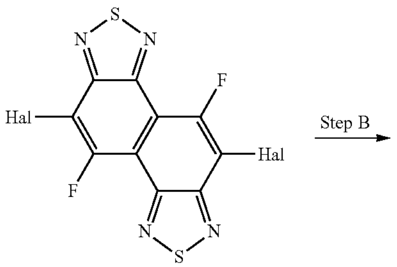

(A1)

-continued

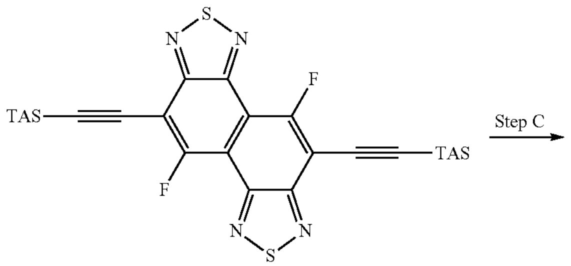

(A2)

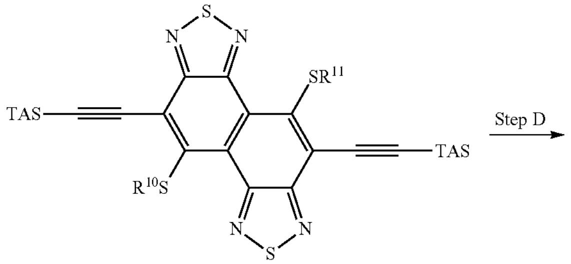

(A3)

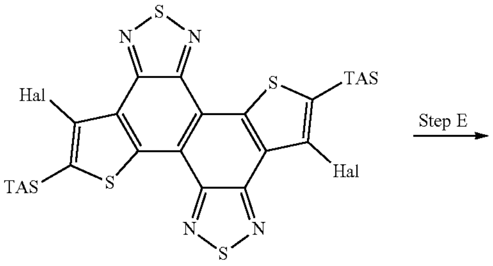

(1-1a)

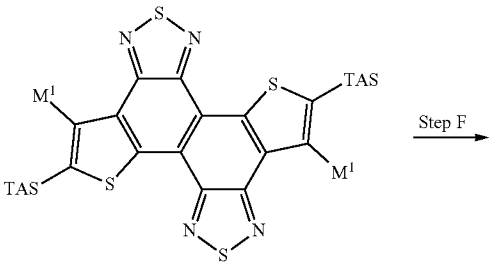

(1-2a)

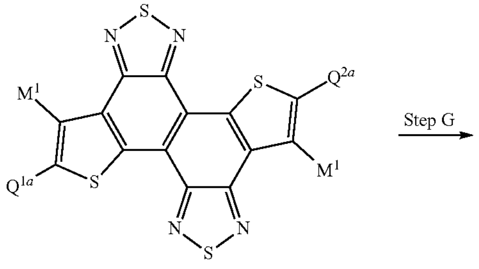

(1-3a)

-continued

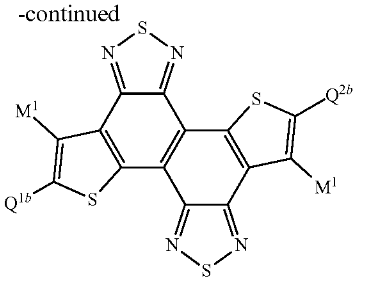

(1-4a)

<Step A>

From commercially-available naphthalene represented by the formula (i), a compound represented by the general formula (A1) (hereinafter, referred to as a "compound (A1)") is produced in accordance with the Examples disclosed in International Publication No. WO 2018/123207 (step A). In the compound (A1), each of Hals is independently a halogen atom.

The steps B to G described below correspond to the steps 1a to 6a of the case involving use of the compound (A1).

<Step B>

Next, from the compound (A1), a compound represented by the general formula (A2) (hereinafter, referred to as a "compound (A2)") is produced (step B). In the general formula (A2), TAS represents a trialkylsilyl group.

The step B corresponds to the step 1a. Specifically, the step B is a step of generating the compound (A2) by causing the compound (A1) to react with trialkylsilylacetylene in presence of a catalyst. Trialkylsilylacetylene is not limited to any particular one, provided that the reaction proceeds with use of it. Examples of trialkylsilylacetylene encompass trimethylsilylacetylene and triethylsilylacetylene, etc. Trialkylsilylacetylene can be preferably used in an equivalent weight of 2 to 20, more preferably in an equivalent weight of 2 to 10, with respect to 1 equivalent weight of the compound (A1). Examples of the catalyst encompass $Pd(PPh_3)_4$, $Pd(PPh_3)_2Cl_2$, $Pd_2(dba)_3$, and CuI, etc. The reaction in the step B can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (A1). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (A2) is preferably refined prior to the step C described below.

<Step C>

Next, from the compound (A2), a compound represented by a general formula (A3) (hereinafter, referred to as a "compound (A3)") is produced (step C). In the general formula (A3), $R^{10}$ and $R^{11}$ are each independently an alkyl group optionally substituted, and TAS represents a trialkylsilyl group.

The step C corresponds to the step 2a. Specifically, the step C is a step of generating the compound (A3) by causing the compound (A2) to react with a sulphurizing agent. The sulphurizing agent is not limited to any particular one, provided that the reaction proceeds with use of it. Examples of the sulphurizing agent encompass: a sulfide salt such as sodium thiomethoxide and sodium thioethoxide; and Lawesson's reagent. The sulphurizing agent can be preferably used in an equivalent weight of 2 to 20, more preferably in an equivalent weight of 2 to 10, with respect to 1 equivalent weight of the compound (A2). The reaction in the step C can be typically carried out in presence of a solvent. Typically, the reaction temperature is preferably 0° C. to 200° C., more preferably 0° C. to 120° C. The reaction time is typically 1 hour to 48 hours. The compound (A3) is preferably refined prior to the step D described below.

<Step D>

Next, from the compound (A3), a compound represented by the general formula (1-1a) (hereinafter, referred to as a "compound (1-1a)") is produced (step D). In the general formula (1-1a), Hal is the same as that defined above, and TAS represents a trialkylsilyl group. Note that the compound (1-1a) is encompassed in the compound (1) of the present invention.

The step D corresponds to the step 3a. Specifically, the step D is a step of generating the compound (1-1a) by causing the compound (A3) to react with a halogenating agent. The halogenating agent is not limited to any particular one, provided that the reaction proceeds with use of it. Examples of the halogenating agent encompass: N-bromosuccinimide; N-iodosuccinimide; halogen such as bromine, iodine, etc., and halide salts thereof; and so on. The halogenating agent can be preferably used in an equivalent weight of 2 to 20, more preferably in an equivalent weight of 2 to 10, with respect to 1 equivalent weight of the compound (A3). The reaction in the step D can be typically carried out in presence of a solvent. Typically, the reaction temperature is preferably 0° C. to 200° C., more preferably 0° C. to 120° C. The reaction time is typically 1 hour to 48 hours. The compound (1-1a) thus obtained may be refined. The compound (1-1a) is preferably refined prior to the step E described below.

<Step E>

Next, from the compound (1-1a), a compound represented by the general formula (1-2a) (hereinafter, referred to as a "compound (1-2a)") is produced (step E). In the general formula (1-2a), $M^1$ is the same as that defined above, and two M's may be identical to each other or may be different from each other. TAS represents a trialkylsilyl group. Note that the compound (1-2a) is encompassed in the compound (1) of the present invention.

The step E corresponds to the step 4a. Specifically, the step E is a step of generating the compound (1-2a) by causing the compound (1-1a) to react with a boron compound in presence of a catalyst. The boron compound is not limited to any particular one, provided that the reaction proceeds with use of it. Examples of the boron compound encompass boronic acid, boronic acid ester, boronic acid diaminonaphthalene amide, N-methyliminodiacetic acid boronate ester, a trifluoroborate salt group, a triolborate salt group, etc. The boron compound can be preferably used in an equivalent weight of 2 to 20, more preferably in an equivalent weight of 2 to 10, with respect to 1 equivalent weight of the compound (1-1a). Examples of the catalyst encompass $Pd(PPh_3)_4$, $Pd(PPh_3)_2Cl_2$, $Pd_2(dba)_3$, CuI, etc. A ligand may be used as needed. Examples of the ligand encompass triphenylphosphine, Sphos, etc. The reaction in the step E can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (1-1a). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (1-2a) thus obtained may be refined. The compound (1-2a) is preferably refined prior to the step F described below.

<Step F>

Next, from the compound (1-2a), a compound represented by the general formula (1-3a) (hereinafter, referred to as a "compound (1-3a)") is produced (step D). In the general formula (1-3a), $M^1$ is the same as that defined above, and $Q^{1a}$ and $Q^{2a}$ each independently represent a halogen atom. Note that the compound (1-3a) is encompassed in the compound (1) of the present invention.

The step F corresponds to the step 5a. Specifically, the step F is a step of generating the compound (1-3a) by causing the compound (1-2a) to react with a halogenating agent. The halogenating agent is not limited to any particular one, provided that the reaction proceeds with use of it. Examples of the halogenating agent encompass: N-bromosuccinimide; N-iodosuccinimide; halogen such as bromine, iodine, etc., and halide salts thereof. The halogenating agent can be preferably used in an equivalent weight of 2 to 20, more preferably in an equivalent weight of 2 to 10, with respect to 1 equivalent weight of the compound (1-2a). The reaction in the step F can be typically carried out in presence of a solvent. Typically, the reaction temperature is preferably 0° C. to 200° C., more preferably 0° C. to 120° C. The reaction time is typically 1 hour to 48 hours. The compound (1-3a) thus obtained may be refined. The compound (1-3a) is preferably refined prior to the step G described below.

<Step G>

Next, from the compound (1-3a), a compound represented by the general formula (1-4a) (hereinafter, referred to as a "compound (1-4a)") is produced (step G). In the general formula (1-4a), $M^1$ is the same as that defined above, and $Q^{1b}$ and $Q^{2b}$ are each independently a hydrogen atom, an aryl group, a heterocyclic group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group. Note that the compound (1-4a) is encompassed in the compound (1) of the present invention.

The step G corresponds to the step 6a. Specifically, the step G is a step of generating the compound (1-4a) by causing the compound (1-3a) to react with a boron compound or a tin compound in presence of a catalyst. The boron compound is not limited to any particular one, provided that the reaction proceeds with use of it. Examples of the boron compound encompass hydroboration compounds such as pinacol borane, diborane compounds such as bis(pinacolato) diboron, arylboronic acid, arylboronic acid ester, arylboronic acid diaminonaphthalene amide, N-methyliminodiacetic acid arylboronic acid ester, an aryltrifluoroborate salt group, heteroarylboronic acid, heteroarylboronic acid ester, heteroarylboronic acid diaminonaphthalene amide, N-methyliminodiacetic acid heteroarylboronic acid ester, a heteroaryltrifluoroborate salt group, a triolborate salt group, etc. The tin compound is not limited to any particular one, provided that the reaction proceeds with use of it. Examples of the tin compound encompass ditin compounds such as bis(trimethyltin) and bis(tributyltin), trialkylaryltin, trialkylheteroaryltin, etc. The boron compound or the tin compound can be independently used preferably in an equivalent weight of 2 to 20, more preferably in an equivalent weight of 2 to 10, with respect to 1 equivalent weight of the compound (1-3a). Examples of the catalyst encompass $Pd(PPh_3)_4$, $Pd(PPh_3)_2Cl_2$, $Pd_2(dba)_3$, CuI, etc. The reaction in the step G can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (1-3a). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (1-4a) thus obtained may be refined.

(Method 2 for Producing Compound (1))

The method for producing the compound (1) (intermediate) is not limited to the method 1 described above. For another example, it is possible to synthesize a compound represented by the general formula (A1) by the step A to produce naphthobisthiadiazole fused with a thiophene ring. Preferable steps will be described in accordance with the reaction scheme shown below.

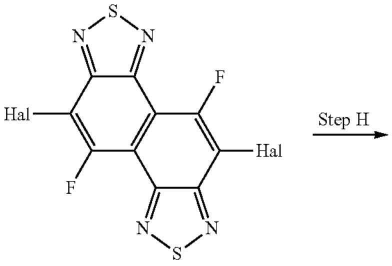

(A1)

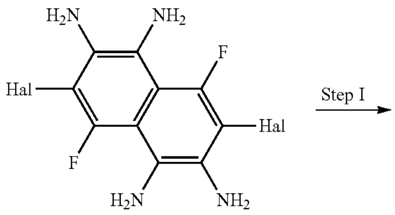

(A4)

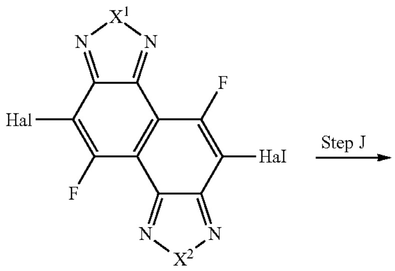

(A5)

-continued

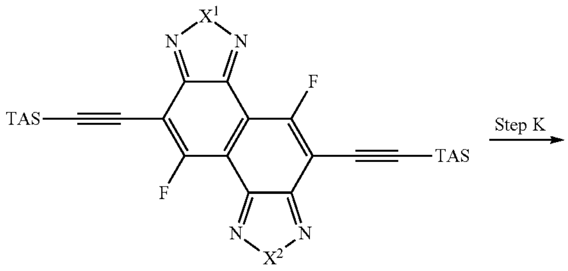

(A6)

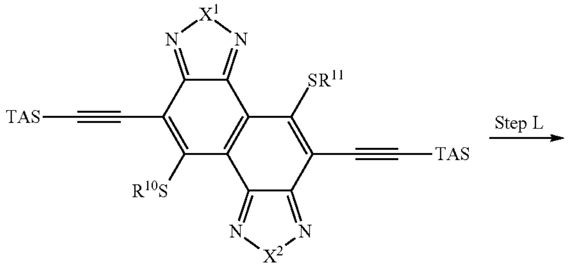

(A7)

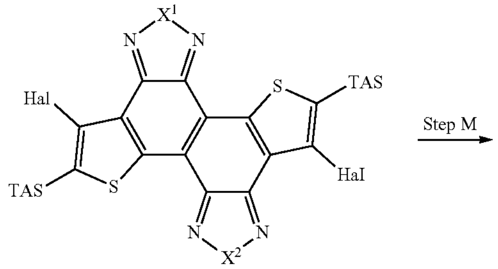

(1-1)

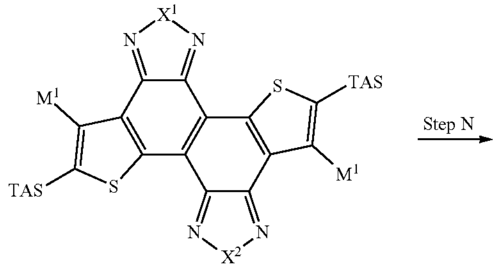

(1-2)

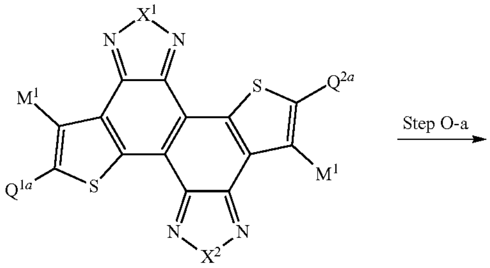

(1-3)

-continued

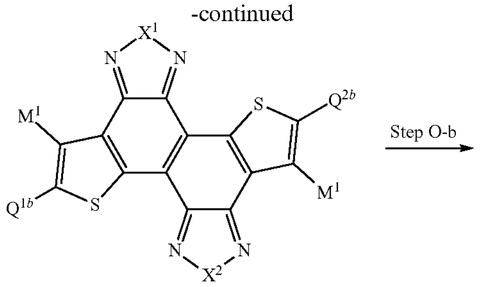

(1-4)

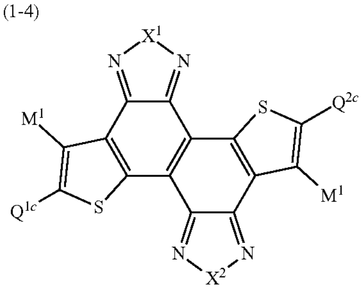

(1-5)

<Step H>

From the compound (A1), a compound represented by the general formula (A4) (hereinafter, referred to as a "compound (A4)") is produced (step H). In the general formula (A4), each of Hals is independently a halogen atom.

The step H is, specifically, a step of generating the compound (A4) by causing the compound (A1) to react with a reducing agent. The reducing agent is not limited to any particular one, provided that the reaction proceeds with use of it. Examples of the reducing agent encompass sodium borohydride, aluminum lithium hydride, etc. The reducing agent can be preferably used in an equivalent weight of 2 to 20, more preferably in an equivalent weight of 2 to 10, with respect to 1 equivalent weight of the compound (A1). The solvent is not limited to any particular one, provided that the reaction proceeds with use of it. Typically, the reaction temperature is preferably 0° C. to 200° C., more preferably 0° C. to 120° C. The reaction time is typically 1 hour to 48 hours. The compound (A4) is preferably refined prior to the step I described below.

<Step I>

From the compound (A4), a compound represented by the general formula (A5) (hereinafter, referred to as a "compound (A5)") is produced (step I). In the general formula (A5), Hal is the same as that defined above. Each of —$X^1$— and —$X^2$— independently represents —O—, —S—, —Se—, —$NM^2$-, or —$CM^3$=$CM^4$-. Each of $M^2$, $M^3$, and $M^4$ is independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is the same as that defined above.

The step I is, specifically, a step of producing the compound (A5) by causing the compound (A4) to react with a chalcogenizing agent, a nitrification agent, or 1,2-diketone. The chalcogenizing agent is not limited to any particular one, provided that the reaction proceeds with use of it. Examples of the chalcogenizing agent encompass hydrogen peroxide, thionyl chloride, selenide chloride, etc. The chalcogenizing agent can be preferably used in an equivalent weight of 2 to 20, more preferably in an equivalent weight of 2 to 10, with respect to 1 equivalent weight of the compound (A4). The nitrification agent is not limited to any particular one, provided that the reaction proceeds with use of it. Examples of the nitrification agent encompass sodium nitrite, etc. The nitrification agent can be preferably used in an equivalent weight of 2 to 20, more preferably in an equivalent weight of 2 to 10, with respect to 1 equivalent weight of the compound (A4). 1,2-diketone is not limited to any particular one, provided that the reaction proceeds with use of it. Examples of 1,2-diketone encompass acetyl, benzil, oxalyl chloride, oxalyl bromide, etc. 1,2-diketone can be preferably used in an equivalent weight of 2 to 20, more preferably in an equivalent weight of 2 to 10, with respect to 1 equivalent weight of the compound (A4). In the above reaction, a base may be used as needed. The base is not limited to any particular one, provided that the above reaction proceeds with use of it. The solvent is not limited to any particular one, provided that the above reaction proceeds with use of it. The solvent may be a solvent that can also function as a base, such as triethanolamine or piperidine. Typically, the reaction temperature is preferably 0° C. to 200° C., more preferably 0° C. to 120° C. The reaction time is typically 1 hour to 48 hours. The compound (A5) is preferably refined prior to the step J described below.

Note that the compound (A5) in which both —$X^1$— and —$X^2$— are —S— corresponds to the compound (A1). In order to produce the compound (A5) other than the one corresponding to the compound (A1), the production method preferably includes the steps H and I.

The steps J to O described below correspond to the steps 1a to 6a of the case involving use of the compound (A5), and to the steps B to G of the case involving use of the compound (A1).

<Step J>

Next, from the compound (A5), a compound represented by the general formula (A6) (hereinafter, referred to as a "compound (A6)") is produced (step J). In the general formula (A6), TAS represents a trialkylsilyl group.

The step J corresponds to the step 1a. Specifically, the step J is a step of generating the compound (A6) by causing the compound (A5) to react with trialkylsilylacetylene in presence of a catalyst. Trialkylsilylacetylene is not limited to any particular one, provided that the reaction proceeds with use of it. Examples of trialkylsilylacetylene encompass trimethylsilylacetylene, triethylsilylacetylene, etc. Trialkylsilylacetylene can be preferably used in an equivalent weight of 2 to 20, more preferably in an equivalent weight of 2 to 10, with respect to 1 equivalent weight of the compound (A5). Examples of the catalyst encompass $Pd(PPh_3)_4$, $Pd(PPh_3)_2Cl_2$, $Pd_2(dba)_3$, CuI, etc. The reaction in the step J can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (A5). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (A6) is preferably refined prior to the step K described below.

<Step K>

Next, from the compound (A6), a compound represented by the general formula (A7) (hereinafter, referred to as a "compound (A7)") is produced (step K). In the general formula (A7), $R^{10}$ and $R^{11}$ are each independently an alkyl group optionally substituted, and TAS represents a trialkylsilyl group.

The step K corresponds to the step 2a. Specifically, the step K is a step of generating the compound (A7) by causing the compound (A6) to react with a sulphurizing agent. The sulphurizing agent is not limited to any particular one, provided that the reaction proceeds with use of it. Examples of the sulphurizing agent encompass: a sulfide salt such as sodium thiomethoxide and sodium thioethoxide; and Lawesson's reagent. The sulphurizing agent can be preferably used in an equivalent weight of 2 to 20, more preferably in an equivalent weight of 2 to 10, with respect to 1 equivalent weight of the compound (A6). The reaction in the step K can be typically carried out in presence of a solvent. Typically, the reaction temperature is preferably 0° C. to 200° C., more preferably 0° C. to 120° C. The reaction time is typically 1 hour to 48 hours. The compound (A7) is preferably refined prior to the step L described below.

<Step L>

Next, from the compound (A7), a compound represented by the general formula (1-1) (hereinafter, referred to as a "compound (1-1)") is produced (step L). In the general formula (1-1), Hal is the same as that defined above, and TAS represents a trialkylsilyl group. Note that the compound (1-1) is encompassed in the compound (1) of the present invention.

The step L corresponds to the step 3a. Specifically, the step L is a step of generating the compound (1-1) by causing the compound (A7) to react with a halogenating agent. The halogenating agent is not limited to any particular one, provided that the reaction proceeds with use of it. Examples of the halogenating agent encompass: N-bromosuccinimide; N-iodosuccinimide; halogen such as bromine, iodine, etc., and halide salts thereof; and so on. The halogenating agent can be preferably used in an equivalent weight of 2 to 20, more preferably in an equivalent weight of 2 to 10, with respect to 1 equivalent weight of the compound (A7). The reaction in the step L can be typically carried out in presence of a solvent. Typically, the reaction temperature is preferably 0° C. to 200° C., more preferably 0° C. to 120° C. The reaction time is typically 1 hour to 48 hours. The compound (1-1) thus obtained may be refined. The compound (1-1) is preferably refined prior to the step M described below.

<Step M>

Next, from the compound (1-1), a compound represented by the general formula (1-2) (hereinafter, referred to as a "compound (1-2)") is produced (step M). In the general formula (1-2), $M^1$ is the same as that defined above, and two M's may be identical to each other or may be different from each other. TAS represents a trialkylsilyl group. Note that the compound (1-2) is encompassed in the compound (1) of the present invention.

The step M corresponds to the step 4a. Specifically, the step M is a step of generating the compound (1-2) by causing the compound (1-1) to react with a boron compound in presence of a catalyst. The boron compound is not limited to any particular one, provided that the reaction proceeds with use of it. Examples of the boron compound encompass boronic acid, boronic acid ester, boronic acid diaminonaphthalene amide, N-methyliminodiacetic acid boronate ester, a trifluoroborate salt group, a triolborate salt group, etc. The boron compound can be preferably used in an equivalent weight of 2 to 20, more preferably in an equivalent weight of 2 to 10, with respect to 1 equivalent weight of the compound (1-1). Examples of the catalyst encompass $Pd(PPh_3)_4$, $Pd(PPh_3)_2Cl_2$, $Pd_2(dba)_3$, CuI, etc. A ligand may be used as needed. Examples of the ligand encompass triphenylphosphine, Sphos, etc. The reaction in the step M can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (1-1). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (1-2) thus obtained may be refined. The compound (1-2) is preferably refined prior to the step N described below.

<Step N>

Next, from the compound (1-2), a compound represented by the general formula (1-3) (hereinafter, referred to as a "compound (1-3)") is produced (step N). In the general formula (1-3), $M^1$ is the same as that defined above, and $Q^{1a}$ and $Q^{2a}$ each independently represent a halogen atom. Note that the compound (1-3) is encompassed in the compound (1) of the present invention.

The step N corresponds to the step 5a. Specifically, the step N is a step of generating the compound (1-3) by causing the compound (1-2) to react with a halogenating agent. The halogenating agent is not limited to any particular one, provided that the reaction proceeds with use of it. Examples of the halogenating agent encompass: N-bromosuccinimide; N-iodosuccinimide; halogen such as bromine, iodine, etc., and halide salts thereof; and so on. The halogenating agent can be preferably used in an equivalent weight of 2 to 20, more preferably in an equivalent weight of 2 to 10, with respect to 1 equivalent weight of the compound (1-2). The reaction in the step N can be typically carried out in presence of a solvent. Typically, the reaction temperature is preferably 0° C. to 200° C., more preferably 0° C. to 120° C. The reaction time is typically 1 hour to 48 hours. The compound (1-3) thus obtained may be refined. The compound (1-3) is preferably refined prior to the step O described below.

<Step O-a>

Next, from the compound (1-3), a compound represented by the general formula (1-4) (hereinafter, referred to as a "compound (1-4)") is produced (step O). In the general formula (1-4), $M^1$ is the same as that defined above, and $Q^{1b}$ and $Q^{2b}$ are each independently a hydrogen atom, an aryl group optionally substituted with Z, a heterocyclic group optionally substituted with Z, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group. Note that the compound (1-4) is encompassed in the compound (1) of the present invention.

The step O-a corresponds to the step 6a. Specifically, the step O-a is a step of generating the compound (1-4) by causing the compound (1-3) to react with a boron compound or a tin compound in presence of a catalyst. The boron compound is not limited to any particular one, provided that the reaction proceeds with use of it. Examples of the boron compound encompass hydroboration compounds such as pinacol borane, diborane compounds such as bis(pinacolato) diboron, arylboronic acid, arylboronic acid ester, arylboronic acid diaminonaphthalene amide, N-methyliminodiacetic acid arylboronic acid ester, an aryltrifluoroborate salt group, heteroarylboronic acid, heteroarylboronic acid ester, heteroarylboronic acid diaminonaphthalene amide, N-methyliminodiacetic acid heteroarylboronic acid ester, a heteroaryltrifluoroborate salt group, a triolborate salt group, etc. The tin compound is not limited to any particular one, provided that the reaction proceeds with use of it. Examples of the tin compound encompass ditin compounds such as bis(trimethyltin) and bis(tributyltin), trialkylaryltin, and trialkylheteroaryltin. The boron compound or the tin compound can be independently used preferably in an equivalent weight of 2 to 20, more preferably in an equivalent weight of 2 to 10, with respect to 1 equivalent weight of the compound (1-3). Examples of the catalyst encompass $Pd(PPh_3)_4$, $Pd(PPh_3)_2Cl_2$, $Pd_2(dba)_3$, CuI, etc. The reaction in the step O can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (1-3). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (1-4) thus obtained may be refined.

<Step O-b>

Next, by formylating the compound (1-4), a compound represented by the general formula (1-5) (hereinafter, referred to as a "compound (1-5)") is produced (step O-b). In the general formula (1-5), $M^1$ is the same as that defined above, and $Q^{1c}$ and $Q^{2c}$ each independently represent a formyl group. Note that the compound (1-5) is encompassed in the compound (1) of the present invention. The step O-b carries out formylation by an ordinarily employed method.

(Method 3 for Producing Compound (1))

The method for producing the compound (1) (intermediate) is not limited to the methods 1 and 2 described above. For further another example, it is possible to synthesize a compound represented by the general formula (A8) shown below from a commercially-available compound to produces naphthobisthiadiazole fused with a thiazole ring. Preferable steps will be described in accordance with the reaction scheme shown below.

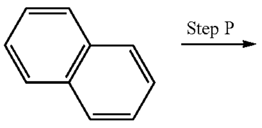

(i)

-continued

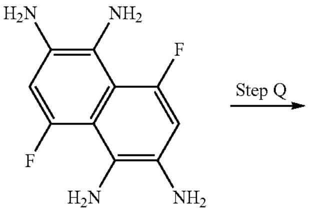

(A8)

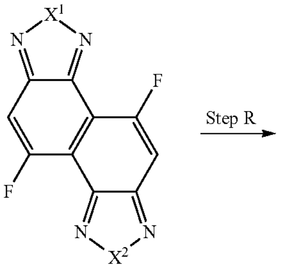

(A9)

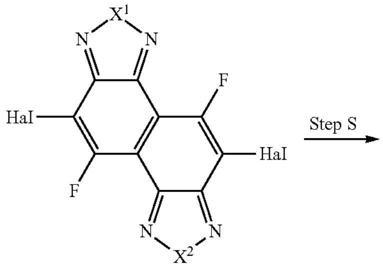

(A10)

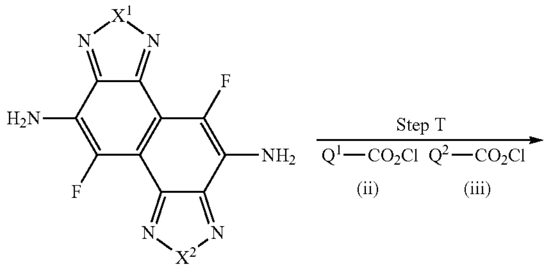

(A11)

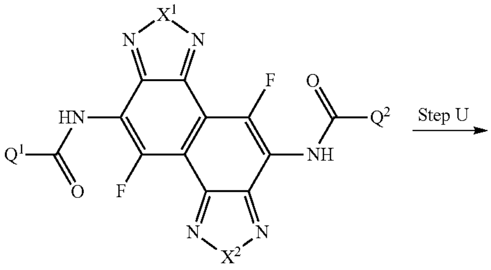

(A12)

-continued

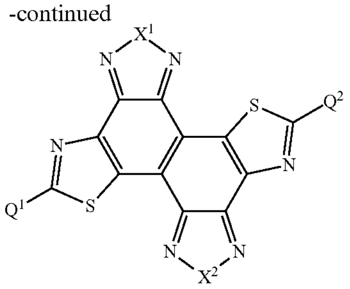

(1-6)

<Step P>

From commercially available naphthalene represented by the formula (i) a compound represented by the general formula (A8) (hereinafter, referred to as a "compound (A8) ") is produced in accordance with the Examples disclosed in International Publication No. WO 2018/123207.

<Step Q>

From the compound (A8), a compound represented by the general formula (A9) (hereinafter, referred to as a "compound (A9)") is produced (step Q). In the general formula (A9), —$X^1$— and —$X^2$— each independently represent —O—, —S—, —Se—, —$NM^2$-, or —$CM^3$=$CM^4$-. Here, $M^2$, $M^3$, and $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is the same as that defined above.

The step Q is, specifically, a step of producing the compound (A9) by causing the compound (A8) to react with a chalcogenizing agent, a nitrification agent, or 1,2-diketone. The chalcogenizing agent is not limited to any particular one, provided that the reaction proceeds with use of it. Examples of the chalcogenizing agent encompass hydrogen peroxide, thionyl chloride, selenide chloride, etc. The chalcogenizing agent can be preferably used in an equivalent weight of 2 to 20, more preferably in an equivalent weight of 2 to 10, with respect to 1 equivalent weight of the compound (A8). The nitrification agent is not limited to any particular one, provided that the reaction proceeds with use of it. Examples of the nitrification agent encompass sodium nitrite, etc. The nitrification agent can be preferably used in an equivalent weight of 2 to 20, more preferably in an equivalent weight of 2 to 10, with respect to 1 equivalent weight of the compound (A8). 1,2-diketone is not limited to any particular one, provided that the reaction proceeds with use of it. Examples of 1,2-diketone encompass acetyl, benzil, oxalyl chloride, oxalyl bromide, etc. 1,2-diketone can be preferably used in an equivalent weight of 2 to 20, more preferably in an equivalent weight of 2 to 10, with respect to 1 equivalent weight of the compound (A8). In the above reaction, a base may be used as needed. The base is not limited to any particular one, provided that the reaction proceeds with use of it. The solvent is not limited to any particular one, provided that the above reaction proceeds with use of it. The solvent may be a solvent that can also function as a base, such as triethanolamine or piperidine. Typically, the reaction temperature is preferably 0° C. to 200° C., more preferably 0° C. to 120° C. The reaction time is typically 1 hour to 48 hours. The compound (A9) is preferably refined prior to the step R described below.

The steps R to U described below correspond to the steps 1b to 4b in the case involving use of the compound (A9).

<Step R>

Next, from the compound (A9), a compound represented by the general formula (A10) (hereinafter, referred to as a "compound (A10)") is produced (step R).

The step R corresponds to the step 1b. Specifically, the step R is a step of generating the compound (A10) by causing the compound (A9) to react with a halogenating agent. The halogenating agent is not limited to any particular one, provided that the reaction proceeds with use of it. Examples of the halogenating agent encompass: N-bromosuccinimide; N-iodosuccinimide; halogen such as bromine, iodine, etc., and halide salts thereof; and so on. The halogenating agent can be preferably used in an equivalent weight of 2 to 20, more preferably in an equivalent weight of 2 to 10, with respect to 1 equivalent weight of the compound (A9). The solvent is not limited to any particular one, provided that the reaction proceeds with use of it. Typically, the reaction temperature is preferably 0° C. to 200° C., more preferably 0° C. to 120° C. The reaction time is typically 1 hour to 48 hours. The compound (A10) is preferably refined prior to the step S described below.

<Step S>

Next, from the compound (A10), a compound represented by the general formula (A11) (hereinafter, referred to as a "compound (A11)") is produced (step S).

The step S corresponds to the step 2b. Specifically, the step S is a step of generating the compound (A11) by causing the compound (A10) to react with an aminating agent. The aminating agent is not limited to any particular one, provided that the reaction proceeds with use of it. Examples of the aminating agent encompass an aqueous ammonia solution, liquid ammonia, etc. The aminating agent can be preferably used in an equivalent weight of 2 to 20, more preferably in an equivalent weight of 2 to 10, with respect to 1 equivalent weight of the compound (A10). The solvent is not limited to any particular one, provided that the reaction proceeds with use of it. Typically, the reaction temperature is preferably 0° C. to 200° C., more preferably 0° C. to 120° C. The reaction time is typically 1 hour to 48 hours. The compound (A11) is preferably refined prior to the step T described below.

<Step T>

Next, a compound represented by the general formula (A12) (hereinafter, referred to as "compound (A12)") is produced from the compound (A11), carboxylic acid chloride represented by a general formula (ii) ($Q^1$-$CO_2Cl$) (hereinafter, such a compound will be referred to as "compound (ii)"), and carboxylic acid chloride represented by a general formula (iii) ($Q^2$-$CO_2Cl$) (hereinafter, such a compound will be referred to as "compound (iii)") (step T). In the general formulae (ii), (iii), and (A12), $Q^1$ and $Q^2$ are each independently a hydrogen atom, a halogen atom, an aryl group, a heterocyclic group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group. Each of the compound (ii) and the compound (iii) can be synthesized with use of commercially-available carboxylic acid with reference to Document: Synthesis 2003, 18, 2795-2798, for example.

The step T corresponds to the step 3b. Specifically, the step T is a step of generating the compound (A12) by causing the compound (A11) to react with the compound (ii) and the compound (iii). Each of the compound (ii) and the compound (iii) can be independently used preferably in an equivalent weight of 1 to 20, more preferably in an equivalent weight of 1 to 10, with respect to 1 equivalent weight of the compound (A11). The reaction in the step T can be typically carried out in presence of a base and a solvent. The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (A11). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (A12) is preferably refined prior to the step U described below.

<Step U>

Next, from the compound (A12), a compound represented by the general formula (1-6) (hereinafter, referred to as a "compound (1-6)") is produced (step U). Note that the compound (1-6) is encompassed in the compound (1) of the present invention.

The step U corresponds to the step 4b. Specifically, the step U is a step of generating the compound (1-6) by causing the compound (A12) to react with a sulphurizing agent. The sulphurizing agent is not limited to any particular one, provided that the reaction proceeds with use of it. Examples of the sulphurizing agent encompass: a sulfide salt such as sodium thiomethoxide and sodium thioethoxide; and Lawesson's reagent. The sulphurizing agent can be preferably used in an equivalent weight of 2 to 20, more preferably in an equivalent weight of 2 to 10, with respect to 1 equivalent weight of the compound (A12). The reaction in the step U can be typically carried out in presence of a solvent. Typically, the reaction temperature is preferably 0° C. to 200° C., more preferably 0° C. to 120° C. The reaction time is typically 1 hour to 48 hours. The compound (1-6) thus obtained may be refined.

(Method for Producing Compound (2))

A method for producing the above-described compound (2) is not limited to any particular one. It is possible to produce the compound (2) by carrying out, by a generally-employed method, a step of introducing, as $Q^1$ and $Q^2$ in the above-described compound (1), $J^1$ and $J^2$, each of which is a skeleton giving an electron donating property and an electron accepting property. Preferable steps will be described in accordance with the reaction scheme shown below.

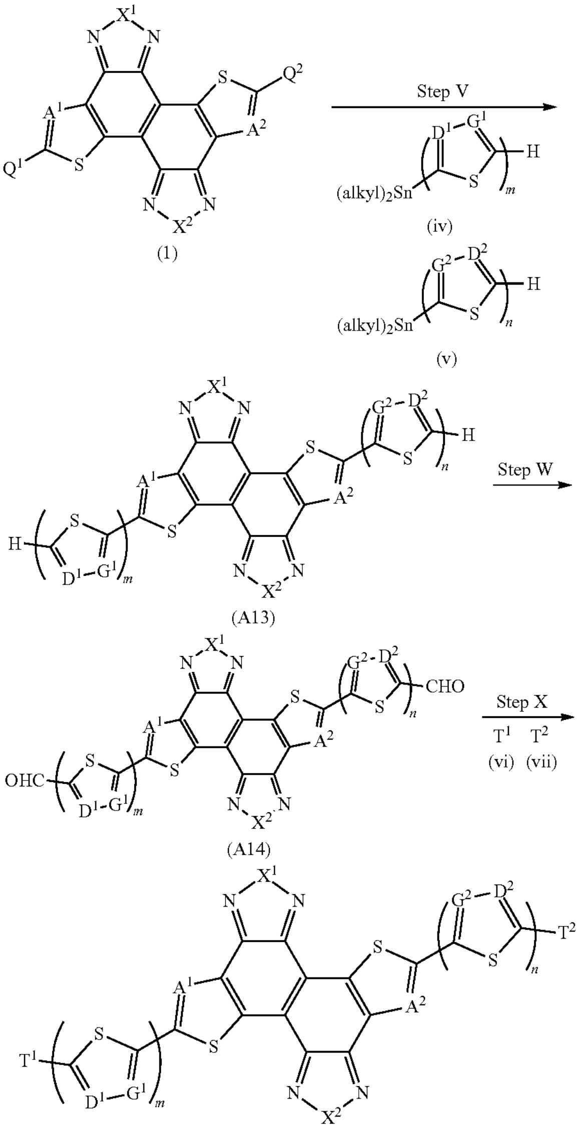

(1) (iv) (v) (A13) (A14) (vi) (vii) (2-1)

<Step V>

A compound represented by the general formula (A13) (hereinafter, referred to as "compound (A13)") is produced from the compound (1), a compound represented by the general formula (iv) (hereinafter, referred to as "compound (iv)"), and a compound represented by the general formula (v) (hereinafter, referred to as "compound (v)") (step V).

In the general formula (1), A1 and A2 are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

$X^1$ and $X^2$ are each independently

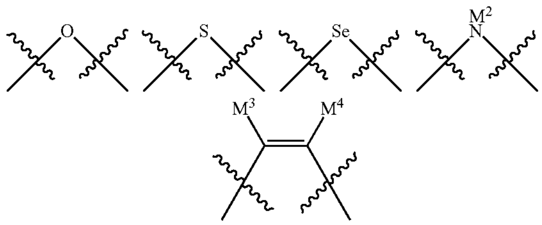

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

The compound (iv) and the compound (v) can be produced from commercially-available thiophene and tin compound. $D^1$ and $G^1$ in the compound (iv) and $D^2$ and $G^2$ in the compound (v) are each independently $CM^1$ or N, and $M^1$ is a hydrogen atom, a halogen atom, an alkyl group optionally substituted with Z, a cyano group, or an alkoxy group optionally substituted. Z is the same as that defined above. The letters “alkyl” represent an alkyl group. The alkyl group may be in a linear chain form or in a branched chain form, and is preferably $C_{1-30}$, more preferably $C_{1-12}$, and even more preferably is methyl, ethyl, propyl, butyl, or pentyl. Each of m and n is independently 0 or a natural number.

The step V is, specifically, a step of generating the compound (A13) by causing the compound (1) to react with the compound (iv) and the compound (v) in presence of a catalyst. Each of the compound (iv) and the compound (v) can be independently used preferably in an equivalent weight of 1 to 20, more preferably in an equivalent weight of 1 to 10, with respect to 1 equivalent weight of the compound (1). Examples of the catalyst encompass $Pd(PPh_3)_4$, $Pd(PPh_3)_2Cl_2$, $Pd_2(dba)_3$, CuI, etc. The solvent is not limited to any particular one, provided that the reaction proceeds with use of it. Typically, the reaction temperature is preferably 0° C. to 200° C., more preferably 0° C. to 120° C. The reaction time is typically 1 hour to 48 hours. The compound (A13) is preferably refined prior to the step W described below.

<Step W>

Next, from the compound (A13), a compound represented by the general formula (A14) (hereinafter, referred to as a “compound (A14)”) is produced (step W). $D^1$, $D^2$, $G^1$, and $G^2$ in the compound (A14) are the same as those defined above. Also, m and n are the same as those defined above.

The step W is, specifically, a step of generating the compound (A14) by causing the compound (A13) to react with N,N-dimethylformamide and phosphoryl chloride. Each of N,N-dimethylformamide and phosphoryl chloride can be independently used preferably in an equivalent weight of 1 to 100, more preferably in an equivalent weight of 1 to 50, with respect to 1 equivalent weight of the compound (A13). The reaction in the step W can be typically carried out in presence of a solvent. Typically, the reaction temperature is preferably 0° C. to 200° C., more preferably 0° C. to 120° C. The reaction time is typically 1 hour to 48 hours. The compound (A14) is preferably refined prior to the step X described below.

<Step X>

A compound represented by the general formula (2-1) (hereinafter, referred to as “compound (2-1)”) is produced from the compound (A14), a commercially-available compound represented by the general formula (vi) (hereinafter, referred to as “compound (vi)”), and a commercially-available compound represented by the general formula (vii) (hereinafter, referred to as “compound (vii)”) (step X). $T^1$ in the compound (vi) and $T^2$ in the compound (vii) are the same as those defined above, and each of $T^1$ and $T^2$ independently represents any of the above-described structures that are cyclic functional groups including an alkenylene group. $D^1$, $D^2$, $G^1$, and $G^2$ in the compound (2-1) are the same as those defined above. Also, m and n are the same as those defined above. Note that the compound (2-1) is encompassed in the compound (2) of the present invention.

The step X is, specifically, a step of generating the compound (2-1) by causing the compound (A14) to react with the compound (vi) and the compound (vii) in presence of a base. Each of the compound (vi) and the compound (vii) can be independently used preferably in an equivalent weight of 1 to 20, more preferably in an equivalent weight of 1 to 10, with respect to 1 equivalent weight of the compound (A14). The base is not limited to any particular one, provided that the reaction proceeds with use of it. The base can be preferably used in an equivalent weight of 1 to 40, more preferably in an equivalent weight of 1 to 20, with respect to 1 equivalent weight of the compound (A14). The solvent is not limited to any particular one, provided that the reaction proceeds with use of it. The solvent may be a solvent that can also function as a base, such as triethylamine or piperidine. Typically, the reaction temperature is preferably 0° C. to 200° C., more preferably 0° C. to 120° C. The reaction time is typically 1 hour to 48 hours. The compound (2-1) thus obtained may be refined.

By the above-described production method, it is possible to produce the compound (2-1), more preferably a compound represented by the general formula (2-2) below (hereinafter, referred to as “compound (2-2)”).

(2-2)

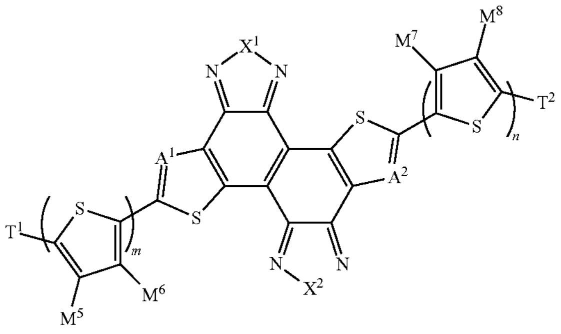

In the general formula (2-2), $A^1$, $A^2$, $T^1$, $T^2$, $X^1$, $X^2$, m, and n are the same as those defined above;

$M^5$ to $M^8$ are each independently a hydrogen atom, a halogen atom, an alkyl group, an alkoxy group, an alkoxy carbonyl group, an alkyl carbonyl group, or an aryl group.

(Organic Semiconductor Material)

An organic semiconductor material in accordance with an aspect of the present invention containing the compound (2) is rigid and has high planarity, as described above. Thus, in a case where the organic semiconductor material is formed into a film so as to yield an organic semiconductor layer (semiconductor active layer), the organic semiconductor layer thus obtained has a short intermolecular distance, thereby exhibiting a high charge mobility.

The organic semiconductor material in accordance with the aspect of the present invention may contain not only the compound (2) but also other component(s), such as an additive(s) and/or other semiconductor material(s), in order to improve the physical properties such as film formability for the organic semiconductor layer or to carry out doping or the like. As a result of addition of the compound (2) and an additive(s) and/or other semiconductor material(s) as needed, a composition for formation of an organic semiconductor film (organic-semiconductor-film forming composition) is formed.

(Organic Semiconductor Device)

The organic semiconductor material in accordance with the above-described aspect of the present invention may be used to produce an organic semiconductor device including the organic semiconductor material. Specifically, it is possible to produce an organic semiconductor device including an organic semiconductor layer (semiconductor active layer) that is a film formed, on a substrate or the like, from the organic semiconductor material. Examples of the organic semiconductor device in accordance with the aspect of the present invention encompass various devices such as a photoelectric conversion element, an organic thin-film transistor (e.g., a field effect transistor), and a light-emitting device each including the organic semiconductor layer.

A method for producing the organic semiconductor layer for the organic semiconductor device is not limited to any particular one, and may be selected from various conventional production methods publicly known. Examples of the production method encompass: coating methods such as a vapor deposition method and a spin-coating method; and solution methods such as an ink-jet method, a screen-printing method, an offset-printing method, and a micro-contact printing method.

(Organic-Semiconductor-Film Forming Composition)

The organic-semiconductor-film forming composition contains the compound in accordance with the aspect of the present invention, and is suitably used to form an organic semiconductor film.

The compound in accordance with the aspect of the present invention is the same as that defined above. One kind of the compounds may be used alone, or two or more kinds may be used in combination. The content of the compound in the organic-semiconductor-film forming composition is not limited to any particular one. For example, the content of the compound in the organic-semiconductor-film forming composition is preferably in a range identical to a range of the content of the compound in the organic semiconductor film, which will be described later, in a case where the content is expressed as the content of the compound in a solid content obtained by removing the later-described solvent. The organic-semiconductor-film forming composition may contain a binder polymer.

(Binder Polymer)

From the organic-semiconductor-film forming composition containing the binder polymer, an organic semiconductor film having high film quality can be obtained.

The binder polymer is not limited to any particular one. Examples of the binder polymer encompass: insulating polymers such as polystyrene, poly(a-methyl styrene), polycarbonate, polyarylate, polyester, polyamide, polyimide, polyurethane, polysiloxane, polysulfone, polymethyl acrylate, polymethyl methacrylate, cellulose, polyethylene, and polypropylene; and copolymers thereof. In addition to these polymers, examples of the binder polymer encompass: rubbers such as an ethylene-propylene rubber, an acrylonitrile-butadiene rubber, a hydrogenized nitrile rubber, a fluoro rubber, a perfluoroelastomer, a tetrafluoroethylene-propylene copolymer, an ethylene-propylene-diene copolymer, a styrene-butadiene rubber, polychloroprene, polyneoprene, a butyl rubber, a methyl phenyl silicone resin, a methyl phenyl vinyl silicone resin, a methyl vinyl silicone resin, a fluorosilicone resin, an acrylic rubber, an ethylene acrylic rubber, chlorosulfonated polyethylene, chloropolyethylene, an epichlorohydrin copolymer, a polyisoprene-natural rubber copolymer, polyisoprene rubber, a styrene-isoprene block copolymer, a polyester-urethane copolymer, a polyether-urethane copolymer, a thermoplastic polyether ester elastomer, and a polybutadiene rubber; and a thermoplastic elastomer polymer. Examples of the binder polymer further encompass: photoconductive polymers such as polyvinyl carbazole and polysilane; electroconductive polymers such as polythiophene, polypyrrole, polyaniline, and polyparaphenylene vinylene; and semiconductor polymers such as those described in, e.g., Chemistry of Materials, 2014, 26, 647.

From the viewpoint of the charge mobility, the binder polymer preferably has a structure not including a polar group. The polar group herein refers to a functional group having a hetero atom other than a carbon atom or a hydrogen atom. The binder polymer having the structure not including the polar group is preferably polystyrene or poly(a-methyl styrene), from among those exemplified above. The semiconductor polymer is also preferable as the binder polymer.

The mass-average molecular weight of the binder polymer is not limited to any particular one. For example, the mass-average molecular weight of the binder polymer is preferably 1,000 to 10 million, more preferably 3,000 to 5 million, and even more preferably 5,000 to 3 million.

The glass-transition temperature of the binder polymer is not limited to any particular one, and is set appropriately according to the purpose, etc. For example, in order to impart high mechanical strength to the organic semiconductor film, the glass-transition temperature is preferably set high. On the contrary, in order to impart flexibility to the organic semiconductor film, the glass-transition temperature is preferably set low.

One kind of binder polymer may be used alone, or two or more kinds of binder polymers may be used in combination. The content of the binder polymer in the organic-semiconductor-film forming composition is not particularly limited. For example, the content of the binder polymer in the organic-semiconductor-film forming composition is preferably in a range identical to the range of a content of the binder polymer in the organic semiconductor film, which will be described later, in a case where the content is expressed as the content of the binder polymer in a solid content obtained by removing the later-described solvent Forming an organic semiconductor film for an organic thin-film transistor from an organic-semiconductor-film forming composition containing a binder polymer so that the content of the binder polymer falls within the above range results in a further improvement in carrier mobility and durability.

In the organic-semiconductor-film forming composition, the compound in accordance with the aspect of the present invention may be uniformly mixed with the binder polymer, or a part of or the whole of the compound may be phase-separated from the binder polymer. In the organic-semiconductor-film forming composition, the compound and the binder polymer are preferably mixed uniformly with each other at least at the time of application of the organic-semiconductor-film forming composition, for the purpose of achieving ease of application or evenness of application.

(Solvent)

The organic-semiconductor-film forming composition may contain a solvent. The solvent is not limited to any particular one, provided that the above-described compound can be dissolved or dispersed in it. Examples of the solvent encompass an inorganic solvent and an organic solvent. Of these, the organic solvent is preferable. One kind of solvent may be used alone, or two or more kinds of solvents may be used in combination.

The organic solvent is not limited to any particular one. Examples of the organic solvent encompass: hydrocarbon solvents such as hexane, octane, decane, toluene, xylene, mesitylene, ethylbenzene, amylbenzene, decalin, 1-methylnaphthalene, 1-ethylnaphthalene, 1,6-dimethylnaphthalene, and tetralin; ketone solvents such as acetone, methyl ethyl ketone, methyl isobutyl ketone, cyclohexanone, acetophenone, propiophenone, and butyrophenone; halogenated hydrocarbon solvents such as dichloromethane, chloroform, tetrachloromethane, dichloroethane, trichloroethane, tetrachloroethane, chlorobenzene, 1,2-dichlorobenzene, 1,2,4-trichlorobenzene, chlorotoluene, and 1-fluoronaphthalene; heterocyclic solvents such as pyridine, picoline, quinoline, thiophene, 3-butylthiophene, and thieno[2,3-b]thiophene; halogenated heterocyclic solvents such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, and 3,4-dichloro-1,2,5-thiadiazole; ester solvents such as ethyl acetate, butyl acetate, amyl acetate, acetic acid-2-ethylhexyl, γ-butyrolactone, and phenyl acetate; alcohol solvents such as methanol, propanol, butanol, pentanol, hexanol, cyclohexanol, methyl cellosolve, ethyl cellosolve, and ethylene glycol; ether solvents such as dibutyl ether, tetrahydrofuran, dioxane, dimethoxyethane, anisole, ethoxybenzene, propoxybenzene, isopropoxybenzene, butoxybenzene, 2-methyl anisole, 3-methyl anisole, 4-methyl anisole, 4-ethyl anisole, dimethyl anisole (2,3-, 2,4-, 2,5-, 2,6-, 3,4-, 3,5-, or 3,6-), and 1,4-benzodioxane; amide or imido solvents such as N,N-dimethylformamide, N,N-dimethylacetamide, 1-methyl-2-pyrrolidone, 1-methyl-2-imidazolidinone, and 1,3-dimethyl-2-imidazolidinone; sulfoxide solvents such as dimethylsulfoxide; phosphoric ester solvents such as trimethyl phosphate; nitrile solvents such as acetonitrile and benzonitrile; and nitro solvents such as nitromethane and nitrobenzene.

Among these, the organic solvent is preferably the hydrocarbon solvent, the ketone solvent, the halogenated hydrocarbon solvent, the heterocyclic solvent, the halogenated heterocyclic solvent, or the ether solvent, more preferably toluene, xylene, mesitylene, amylbenzene, tetralin, acetophenone, propiophenone, butyrophenone, dichlorobenzene, anisole, ethoxybenzene, propoxybenzene, isopropoxybenzene, butoxybenzene, 2-methyl anisole, 3-methyl anisole, 4-methyl anisole, 1-fluoronaphthalene, 3-chlorothiophene, or 2,5-dibromothiophene, and particularly preferably toluene, xylene, tetralin, acetophenone, propiophenone, butyrophenone, anisole, ethoxybenzene, propoxybenzene, butoxybenzene, 2-methyl anisole, 3-methyl anisole, 4-methyl anisole, 1-fluoronaphthalene, 3-chlorothiophene, or 2,5-dibromothiophene.

The content of the solvent in the organic-semiconductor-film forming composition is preferably 90 mass % to 99.95 mass %, more preferably 95 mass % to 99.9 mass %, even more preferably 96 mass % to 99.9 mass %. Thus, the content of the solid content in the organic-semiconductor-film forming composition is preferably 10 mass % to 0.05 mass %, more preferably 5 mass % to 0.1 mass %, even more preferably 4 mass % to 0.1 mass %.

(Other Components)

As described above, the organic-semiconductor-film forming composition may contain not only the compound in accordance with the aspect of the present invention and the solvent but also other component(s) such as an additive(s) and/or other semiconductor material(s), as needed. The additive may be an additive typically added to an organic-semiconductor-film forming composition, and is not limited to any particular one. Examples of the additive encompass a surfactant, an antioxidant, a crystallization control agent, a crystal orientation control agent, etc. Examples of the surfactant and the antioxidant encompass surfactants and antioxidants described in paragraphs [0136] and [0137] of Japanese Patent Application Publication Tokukai No. 2015-195362, and the description in these paragraphs is favorably incorporated herein as it is.

The content of the additive in the organic-semiconductor-film forming composition is not limited to any particular one. For example, the content of the additive in the organic-semiconductor-film forming composition is preferably in a range identical to a range of the content of the additive in the organic semiconductor film, which will be described later, in a case where the content is expressed as the content of the additive in a solid content obtained by removing the solvent. Forming an organic semiconductor film for an organic thin-film transistor from an organic-semiconductor-film forming composition containing an additive so that the content of the additive falls within the above range results in excellent film formability and a further improvement in carrier mobility and heat resistance of the organic semiconductor film.

(Preparation Method)

A method for preparing the organic-semiconductor-film forming composition is not limited to any particular one. The preparation method may be a generally-employed preparation method. For example, it is possible to prepare the organic-semiconductor-film forming composition by appropriately mixing predetermined amounts of components with a mixer or a stirrer, for example.

If necessary, it is possible to heat the components during or after the mixing. The heating temperature is not limited to any particular one. However, the heating temperature is preferably set in a range 40° C. to 150° C. In a case where the solvent is used, it is preferable to heat the components at a temperature that is within the above-described heating temperature range and is below the boiling point of the solvent.

(Organic Semiconductor Film)

Next, the following will describe the organic semiconductor film. The organic semiconductor film contains the compound in accordance with the aspect of the present invention. The organic semiconductor film preferably has a film thickness of 1 nm to 1000 nm, more preferably 2 nm to 1000 nm, even more preferably 5 nm to 500 nm, particularly preferably 20 nm to 200 nm.

A step of producing the organic semiconductor film may include a step of aligning the compound in accordance with the aspect of the present invention. In a case where an organic semiconductor film is made from the compound having been aligned by this step, the organic semiconductor film can achieve a further improved electron mobility or hole mobility, since a main chain part or a side chain part of the compound in accordance with the aspect of the present invention therein is aligned in one direction.

A method for aligning the compound in accordance with the aspect of the present invention may be selected from methods known as liquid crystal aligning methods. Among the liquid crystal aligning methods, the aligning method is favorably a rubbing method, a photo-alignment technique, a shearing method (shearing force applying method), or a dip coating method, since these methods are simple and useful. More preferably, the aligning method is the rubbing method or the shearing method.

The organic semiconductor film has an electron transporting property or a hole transporting property. Therefore, with a technique for regulating transportation of electrons or holes injected by the electrode or charges generated by absorbed light, the organic semiconductor film is applicable to organic semiconductor devices such as an organic thin-film transistor, an organic photoelectric conversion element (such as an organic solar cell and an optical sensor), etc. In a case where the organic semiconductor film is employed in any of these organic semiconductor devices, the compound in accordance with the aspect of the present invention is preferably used after having been aligned by being subjected to an alignment treatment, in order to improve the electron transporting property or the hole transporting property.

The organic semiconductor film is an organic semiconductor having excellent electron transporting property and excellent stability in operation, and therefore is favorably applicable as a material of the organic semiconductor devices such as organic thin-film transistors, organic solar cells, optical sensors, etc.

(Method for Producing Organic Semiconductor Film)

The method for producing the organic semiconductor film is not limited to any particular one, provided that it includes the step of applying the organic-semiconductor-film forming composition onto the substrate.

Herein, the application of the organic-semiconductor-film forming composition onto the substrate encompasses an aspect of applying the organic-semiconductor-film forming composition directly onto the substrate as well as an aspect of applying the organic-semiconductor-film forming composition above the substrate across an additional layer disposed on the substrate (i.e., an aspect of applying the organic-semiconductor-film forming composition such that the substrate and the organic-semiconductor-film forming composition sandwich the additional layer therebetween). The additional layer (i.e., the layer that is in contact with the organic semiconductor film and constitutes a base of the organic semiconductor film) is necessarily determined according to the structure of the organic thin-film transistor. For example, in a case where the structure is a bottom gate type, the additional layer is a gate insulating film. For another example, in a case where the structure is a top gate type (top gate-bottom contact type and top gate-top contact type), the additional layer is a source electrode or a drain electrode.

During the process of forming the organic semiconductor film, the substrate may be heated or cooled. By changing the temperature of the substrate, it is possible to regulate the film quality or packing of the compound in accordance with the aspect of the present invention in the film.

The material of the substrate is not limited to any particular one, provided that it does not inhibit the characteristics as the organic thin-film transistor, for example. Examples of the substrate encompass a glass substrate and a silicon substrate as well as a film substrate and a plastic substrate that may be flexible.

The temperature of the substrate is not limited to any particular one. The temperature is preferably set so as to fall within a range of 0° C. to 200° C., more preferably a range of 15° C. to 100° C., particularly preferably a range of 20° C. to 95° C., for example.

The method for producing the organic semiconductor film is not limited to any particular one, examples of which encompass a vacuum process and a solution process. Each of the vacuum process and the solution process is preferable. Examples of the vacuum process encompass: physical vapor deposition methods such as a vacuum deposition method, a sputtering method, an ion plating method, and a molecular beam epitaxy (MBE) method; and chemical vapor deposition (CVD) methods such as plasma polymerization. Of these, the vacuum deposition method is preferable. The solution process is preferably carried out with use of the organic-semiconductor-film forming composition containing the above solvent.

The compound in accordance with the aspect of the present invention is stable even under atmosphere (in the air). Therefore, the solution process can be carried out under atmosphere. Furthermore, the solution process enables application of the organic-semiconductor-film forming composition in accordance with the aspect of the present invention to a large area.

The solution process can employ, as the method for applying the organic-semiconductor-film forming composition, a generally-employed method. Examples of the application method encompass: coating methods such as a drop-casting method, a casting method, a dip-coating method, a die-coater method, a roll-coater method, a bar-coater method, and a spin-coating method; various printing methods such as an ink-jet method, a screen-printing method, a gravure printing method, a flexography printing method, an offset-printing method, a micro-contact printing method, etc; Langmuir-Blodgett (LB) method, etc. Among these, the drop-casting method, the casting method, the spin-coating method, the ink-jet method, the gravure printing method, the flexography printing method, the offset-printing method, or the micro-contact printing method is preferable.

In the solution process, it is preferable to dry the organic-semiconductor-film forming composition applied on the substrate. Further preferably, the drying is carried out gradually.

From the viewpoint of the film quality, the organic-semiconductor-film forming composition is preferably subjected to natural drying or thermal drying on a heated substrate and then to vacuum drying. The temperature of the substrate under the natural drying or thermal drying is preferably 20° C. to 100° C., more preferably 20° C. to 80° C. The period of time for the natural drying or thermal drying is preferably 0.5 hours to 20 hours, more preferably 1 hour to 10 hours.

The temperature of the vacuum drying is preferably 20° C. to 100° C., more preferably 20° C. to 80° C. The period of time for the vacuum drying is preferably 1 hour to 20 hours, more preferably 2 hours to 10 hours. The pressure of the vacuum drying is preferably $10^{-6}$ Pa to $10^{-2}$ Pa, more preferably $10^{-5}$ Pa to $10^{-3}$ Pa.

The organic-semiconductor-film forming composition thus dried may be subjected to a forming process or the like as needed so as to be formed into a certain shape or a predetermined pattern.

(Organic Thin-Film Transistor)

Next, the following will describe an organic thin-film transistor (also referred to as an organic TFT), which is a more preferable mode among the above-described organic semiconductor devices including the compound in accordance with the aspect of the present invention.

The organic thin-film transistor includes the above-described organic semiconductor film. Consequently, the organic thin-film transistor in accordance with the aspect of the present invention exhibits a high carrier mobility and can effectively reduce deterioration over time in the characteristics even under atmosphere (in the air), and therefore is operable in a stable manner.

In the present invention, an ambient temperature and humidity under atmosphere are not limited to any particular ones, provided that they are the temperature and humidity applicable as operating conditions for the organic thin-film transistor. For example, the temperature may be room temperature (25±15° C.), and the humidity may be 10 RH % to 90 RH %.

The organic thin-film transistor in accordance with the aspect of the present invention is preferably used as a field effect transistor (FET), more preferably as an insulated-gate FET in which the gate and the channel are insulated from each other.

The thickness of the organic thin-film transistor in accordance with the aspect of the present invention is not limited to any particular one. In order to achieve a thinner transistor, the thickness of the entire transistor is preferably set at 0.1 m to 0.5 m, for example.

The organic thin-film transistor includes the organic semiconductor film (also referred to as the organic semiconductor layer or the semiconductor active layer), and may further include a source electrode, a drain electrode, a gate electrode, and a gate insulating film.

The organic thin-film transistor in accordance with the aspect of the present invention includes the gate electrode, the organic semiconductor film, the gate insulating film interposed between the gate electrode and the organic semiconductor film that are disposed on the substrate, the source electrode and the drain electrode being disposed in contact with the organic semiconductor film and being coupled to each other via the organic semiconductor film. In the organic thin-film transistor in accordance with this aspect, the organic semiconductor film and the gate insulating film are disposed so as to be adjacent to each other.

The structure of the organic thin-film transistor in accordance with the aspect of the present invention is not limited to any particular one, provided that it includes the above-described layers. The organic thin-film transistor may have a structure selected from a bottom contact type structure (a bottom gate-bottom contact type structure and a top gate-bottom contact type structure) and a top contact type structure (a bottom gate-top contact type structure and a top gate-top contact type structure), for example. More preferably, the organic thin-film transistor in accordance with the aspect of the present invention is the bottom gate-bottom contact type or the bottom gate-top contact type (these types will be collectively referred to as a bottom gate type).

The following will describe one example of the structure of the organic thin-film transistor with reference to the drawings.

FIG. 1 is a cross-sectional view schematically illustrating an organic thin-film transistor (field-effect organic thin-film transistor) in accordance with Embodiment 1 of the present invention. As shown in FIG. 1, an organic thin-film transistor 100 includes a substrate 1, a source electrode 5 and a drain electrode 6 formed on the substrate 1 so as to be separated from each other by a predetermined distance, an organic semiconductor layer 2 formed on the substrate 1 so as to cover the source electrode 5 and the drain electrode 6, an insulating layer 3 formed on a part of the organic semiconductor layer 2, and a gate electrode 4 formed on a region corresponding to the insulating layer 3, the region being between the source electrode 5 and the drain electrode 6.

Figure 2:
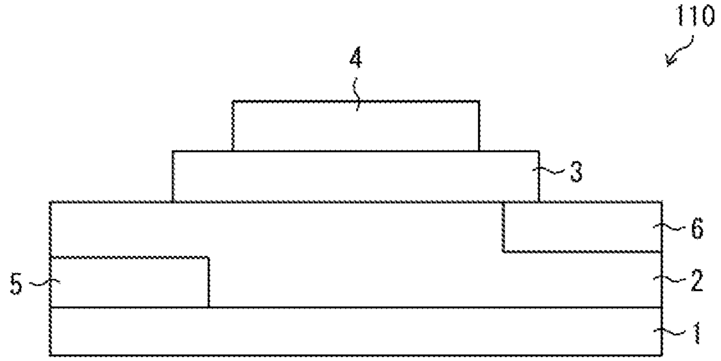
FIG. 2 is a cross-sectional view schematically illustrating an organic thin-film transistor in accordance with Embodiment 2 of the present invention.

FIG. 2 is a cross-sectional view schematically illustrating an organic thin-film transistor (field-effect organic thin-film transistor) in accordance with Embodiment 2 of the present invention. As shown in FIG. 2, an organic thin-film transistor 110 includes a substrate 1, a source electrode 5 formed on the substrate 1, an organic semiconductor layer 2 formed on the substrate 1 so as to cover the source electrode 5, a drain electrode 6 formed on the organic semiconductor layer 2 so as to be separated from the source electrode 5 by a predetermined distance, an insulating layer 3 formed on a part of the organic semiconductor layer 2 so as to partially cover the drain electrode 6, and a gate electrode 4 formed on a region corresponding to the insulating layer 3 so as to partially cover the insulating layer 3, the region being between the source electrode 5 and the drain electrode 6.

Figure 3:
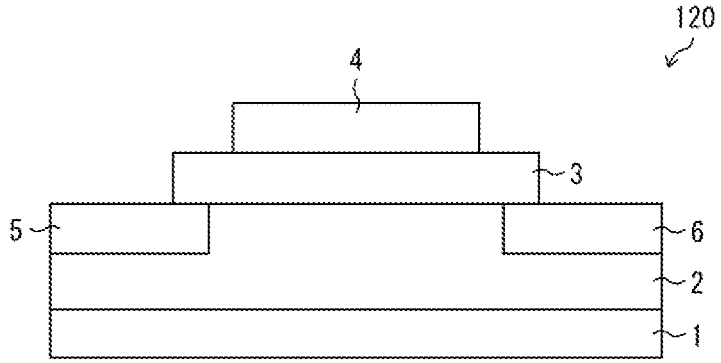
FIG. 3 is a cross-sectional view schematically illustrating an organic thin-film transistor in accordance with Embodiment 3 of the present invention.

FIG. 3 is a cross-sectional view schematically illustrating an organic thin-film transistor (field-effect organic thin-film transistor) in accordance with Embodiment 3 of the present invention. As shown in FIG. 3, an organic thin-film transistor 120 includes a substrate 1, an organic semiconductor layer 2 formed on the substrate 1, a source electrode 5 and a drain electrode 6 formed on the organic semiconductor layer 2 so as to be separated from each other by a predetermined distance, an insulating layer 3 formed on a part of the organic semiconductor layer 2 so as to partially cover the source electrode 5 and the drain electrode 6, and a gate electrode 4 formed on a part of the insulating layer 3 so as to partially cover a region corresponding to the insulating layer 3, the region being between the source electrode 5 and the drain electrode 6.

Figure 4:
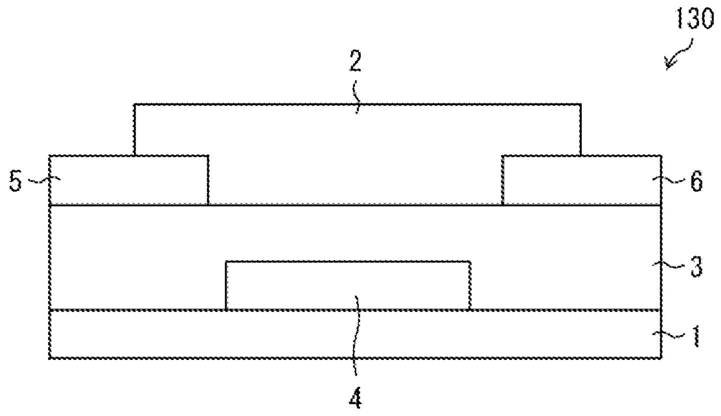
FIG. 4 is a cross-sectional view schematically illustrating an organic thin-film transistor in accordance with Embodiment 4 of the present invention.

FIG. 4 is a cross-sectional view schematically illustrating an organic thin-film transistor (field-effect organic thin-film transistor) in accordance with Embodiment 4 of the present invention. As shown in FIG. 4, an organic thin-film transistor 130 includes a substrate 1, a gate electrode 4 formed on the substrate 1, an insulating layer 3 formed on the substrate 1 so as to cover the gate electrode 4, and a source electrode 5 and a drain electrode 6 formed on the insulating layer 3 so as to partially cover the insulating layer 3 and to be separated from each other by a predetermined distance, and an organic semiconductor layer 2 formed on the insulating layer 3 so as to partially cover the source electrode 5 and the drain electrode 6.

Figure 5:
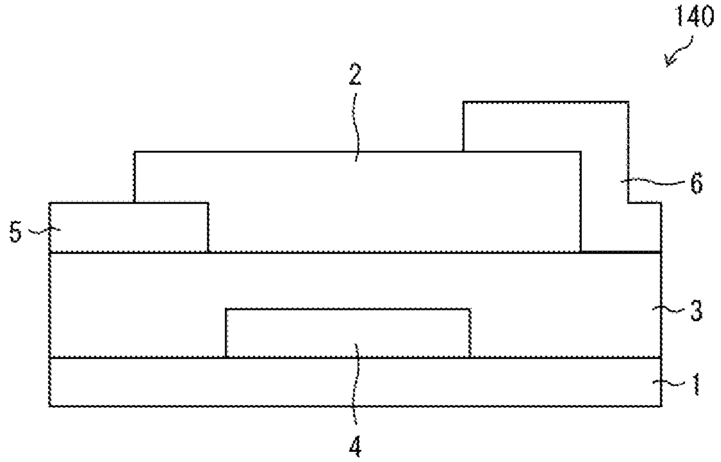
FIG. 5 is a cross-sectional view schematically illustrating an organic thin-film transistor in accordance with Embodiment 5 of the present invention.

FIG. 5 is a cross-sectional view schematically illustrating an organic thin-film transistor (field-effect organic thin-film transistor) in accordance with Embodiment 5 of the present invention. As shown in FIG. 5, an organic thin-film transistor 140 includes a substrate 1, a gate electrode 4 formed on the substrate 1, an insulating layer 3 formed on the substrate 1 so as to cover the gate electrode 4, a source electrode 5 formed on the insulating layer 3 so as to partially cover the insulating layer 3, an organic semiconductor layer 2 formed on a part of the insulating layer 3 so as to partially cover the source electrode 5, and a drain electrode 6 formed so as to partially cover the organic semiconductor layer 2 and partially cover the insulating layer 3 while being separated from the source electrode 5 by a predetermined distance.

Figure 6:
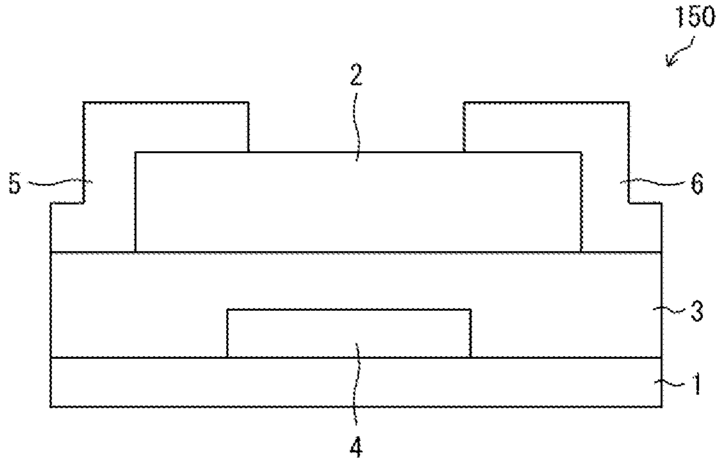
FIG. 6 is a cross-sectional view schematically illustrating an organic thin-film transistor in accordance with Embodiment 6 of the present invention.

FIG. 6 is a cross-sectional view schematically illustrating an organic thin-film transistor (field-effect organic thin-film transistor) in accordance with Embodiment 6 of the present invention. As shown in FIG. 6, an organic thin-film transistor 150 includes a substrate 1, a gate electrode 4 formed on the substrate 1, an insulating layer 3 formed on the substrate 1 so as to cover the gate electrode 4, an organic semiconductor layer 2 formed on a part of the insulating layer 3, a source electrode 5 formed so as to partially cover the organic semiconductor layer 2 and to partially cover the insulating layer 3, and a drain electrode 6 formed so as to partially cover the organic semiconductor layer 2 and partially cover the insulating layer 3 while being separated from the source electrode 5 by a predetermined distance.

Figure 7:
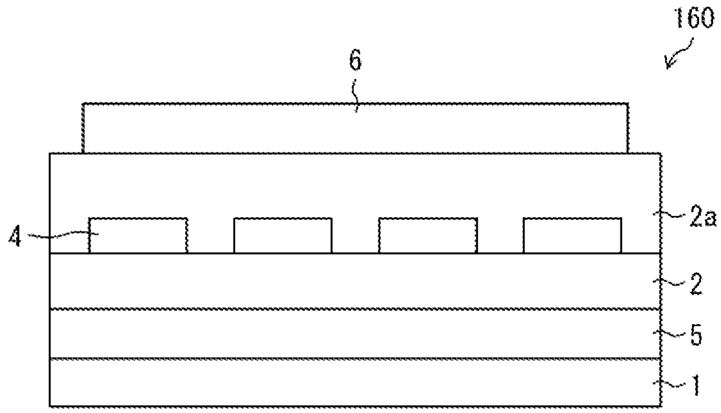
FIG. 7 is a cross-sectional view schematically illustrating an organic thin-film transistor in accordance with Embodiment 7 of the present invention.

FIG. 7 is a cross-sectional view schematically illustrating an organic thin-film transistor (static induction organic thin-film transistor) in accordance with Embodiment 7 of the present invention. As shown in FIG. 7, an organic thin-film transistor 160 includes a substrate 1, a source electrode 5 formed on the substrate 1, an organic semiconductor layer 2 formed on the source electrode 5, plural gate electrodes 4 formed on the organic semiconductor layer 2 so as to be separated from each other by a predetermined distance, an organic semiconductor layer 2*a* formed on the organic semiconductor layer 2 so as to cover all the gate electrodes 4, and a drain electrode 6 formed on the organic semiconductor layer 2*a*. The material of the organic semiconductor layer 2*a* may be the same as or different from the material of the organic semiconductor layer 2.

In each of the organic thin-film transistors in accordance with Embodiments 1 to 7, the organic semiconductor layer 2 (and the organic semiconductor layer 2*a*) contains the compound in accordance with the above-described preferred aspect of the present invention so as to constitute a current path (channel) between the source electrode 5 and the drain electrode 6. Upon application of a voltage, the gate electrode 4 regulates an amount of current flowing through the organic semiconductor layer 2 (and the organic semiconductor layer 2*a*) functioning as the current path (channel).

As described above, the material of the substrate 1 is not limited to any particular one, provided that it does not inhibit the characteristics as the organic thin-film transistor, for example. Examples of the substrate 1 encompass a glass substrate and a silicon substrate as well as a film substrate and a plastic substrate that may be flexible.

In order to form the organic semiconductor layer 2, it is preferable to use a compound soluble in an organic solvent so as to enable coating, i.e., so as to be advantageous in production of the organic thin-film transistor. The compound in accordance with the aspect of the present invention, which has excellent solubility, enables formation of a favorable organic thin film applicable as the organic semiconductor layer 2, when employed together with the above-described method for producing the organic semiconductor film.

The material of the insulating layer 3 only needs to have a high electrical insulating property, and may be a known material. Examples of the material of the insulating layer 3 encompass SiOx, SiNx, $Ta_2O_5$, polyimide, polyvinyl alcohol, polyvinyl phenol, organic glass, and a photoresist. In order to achieve operability at low voltage, the insulating layer 3 is preferably formed of a material with a high dielectric constant.

In a process for forming the organic semiconductor layer 2 on the insulating layer 3, the organic semiconductor layer 2 may be formed on the insulating layer 3 after treating a surface of the insulating layer 3 with a surface treatment agent (such as a silane coupling agent) for surface modification, in order to improve the interfacial quality between the insulating layer 3 and the organic semiconductor layer 2. Examples of the surface treatment agent encompass silylamine compounds such as long chain alkylchlorosilanes, long chain alkylalkoxysilanes, aryl alkylchlorosilaness, aryl alkylalkoxysilanes, fluorinated alkylchlorosilanes, fluorinated alkylalkoxysilanes, and hexamethyldisilazane. Before the treatment with the surface treatment agent, the surface of the insulating layer 3 can be treated with ozone UV or $O_2$ plasma.

Examples of the materials of the gate electrode 4, the source electrode 5, and the drain electrode 6 encompass: metals such as aluminum, gold, silver, copper, alkali metal, and alkaline earth metal; and translucent films and transparent conductive films made from these.

In order to protect the organic thin-film transistor thus formed, a protection film is preferably formed on the organic thin-film transistor. With this, the organic thin-film transistor is shielded from atmosphere (air), which makes it possible to suppress or reduce impairment in the characteristics of the organic thin-film transistor. In addition, with the protection film, it is possible to reduce external effects on the organic thin-film transistor that may otherwise be given in a step of forming, on the organic thin-film transistor, a display device that is to be driven by the organic thin-film transistor.

Examples of the material of the protection film encompass a UV curing resin, a thermosetting resin, and SiONx, which is an inorganic compound. The method for protecting the organic thin-film transistor may be, for example, a method of forming, on the surface of the organic thin-film transistor, a protection film made from a UV curing resin, a thermosetting resin, or SiONx (i.e., covering the organic thin-film transistor with the protection film). In order to effectively shield the organic thin-film transistor from atmosphere, the steps from formation of the organic thin-film transistor to formation of the protection film are preferably carried out under a condition that does not expose the organic thin-film transistor to atmosphere, e.g., under a dry nitrogen atmosphere or under vacuum.

Such a field-effect organic thin-film transistor can be produced by a known method, e.g., by the method described in Japanese Patent Application Publication Tokukaihei No. 5-110069. The static induction organic thin-film transistor can be produced by a known method, e.g., by the method described in Japanese Patent Application Publication Tokukai No. 2004-006476.

(Applications of Organic Thin-Film Transistor)

The application purpose of the above-described organic thin-film transistor is not limited to any particular one. For example, the organic thin-film transistor is applicable to electronic paper, a display device, a sensor, an electronic tag, etc.

An organic thin-film solar cell includes an organic semiconductor film (also referred to as an organic semiconductor layer or a semiconductor active layer), and may further include an anode electrode, a cathode electrode, a hole transport layer, and an electron transport layer.

The structure of the organic thin-film solar cell of the present invention is not limited to any particular one, provided that it includes the above-describer layers. The structure of the organic thin-film solar cell may be any of a forward layer type, a reverse layer type, a tandem type (multijunction type), etc.

The following will describe an example of an organic photoelectric conversion element applied to the organic organic thin-film solar cell, with reference to the drawings.

Figure 8:
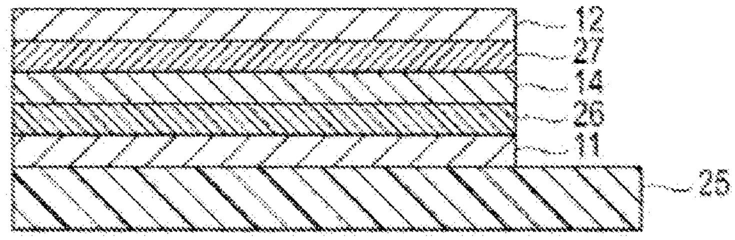
FIG. 8 is a cross-sectional view schematically illustrating an organic thin-film solar cell in accordance with Embodiment 8 of the present invention.

FIG. 8 is a cross-sectional view schematically illustrating a forward layer type organic photoelectric conversion element in accordance with Embodiment 8 of the present invention. Specifically, the organic photoelectric conversion element shown in FIG. 8 includes an anode 11, a hole transport layer 26, a photoelectric conversion layer 14, an electron transport layer 27, and a cathode 12 that are stacked in this order on a substrate 25. Note that the substrate 25 is an optional member provided mainly to facilitate formation of the anode 11 by a coating method, the anode 11 being to be applied on the substrate 25.

While the organic photoelectric conversion element shown in FIG. 8 is under operation, light is emitted from the substrate 25 side. In the present embodiment, the anode 11 is made of a transparent electrode material (e.g., ITO) so that the emitted light reaches the photoelectric conversion layer 14. The light emitted from the substrate 25 side passes through the transparent anode 11 and the hole transport layer 26 so as to reach the photoelectric conversion layer 14.

The photoelectric conversion layer 14 includes a p-type organic semiconductor and an n-type organic semiconductor. When the light enters the photoelectric conversion layer 14, electrons in the p-type organic semiconductor are excited from a highest occupied molecular orbital (hereinafter, occasionally referred to as "HOMO") to a lowest unoccupied molecular orbital (hereinafter, occasionally referred to as "LUMO"), and then the electrons move to a conduction band of the n-type organic semiconductor. Thereafter, the electrons passes through the electron transport layer 27 and the cathode 12, and then move to a conduction band of a conjugated polymer compound via an external circuit. Then, the electrons generated in the conduction band of the p-type organic semiconductor move to LUMO level.

Meanwhile, when light enters the photoelectric conversion layer 14, holes generated in HOMO level of the p-type organic semiconductor pass through the hole transport layer 26 and the anode 11, and then move to a valence band in the n-type organic semiconductor via an external circuit. In this manner, a photoelectric current flows in the photoelectric conversion layer 14, so that electricity is generated. Such photocharge separation is considered to be further promoted with increasing contact interface between the p-type organic semiconductor and the n-type organic semiconductor. Therefore, in the present invention, it is particularly preferable to use a bulk heterojunction type photoelectric conversion layer (not illustrated) in which the p-type organic semiconductor and the n-type organic semiconductor are uniformly mixed. However, the photoelectric conversion layer 14 is not limited only to this.

The hole transport layer 26 is made of a material having a high hole mobility, and has a function to efficiently transport, to the anode 11, holes generated in the pn junction interface of the photoelectric conversion layer 14. Meanwhile, the electron transport layer 27 is made of a material having a high electron mobility, and has a function to efficiently transport, to the cathode 12, electrons generated in the pn junction interface of the photoelectric conversion layer 14.

Figure 9:
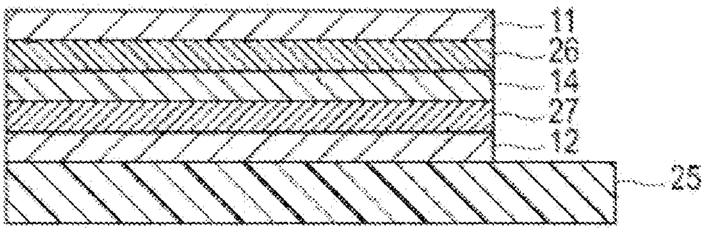
FIG. 9 is a cross-sectional view schematically illustrating an organic thin-film solar cell in accordance with Embodiment 9 of the present invention.

FIG. 9 is a cross-sectional view schematically illustrating a reverse layer type organic photoelectric conversion element in accordance with Embodiment 9 of the present invention. The organic photoelectric conversion element shown in FIG. 9 includes an anode 11 and a cathode 12 arranged in reverse to those in the organic photoelectric conversion element shown in FIG. 8, and includes a hole transport layer 26 and an electron transport layer 27 arranged in reverse to those in the organic photoelectric conversion element shown in FIG. 8. On these points, the organic photoelectric conversion element shown in FIG. 9 differs from the organic photoelectric conversion element shown in FIG. 8. Specifically, the organic photoelectric conversion element shown in FIG. 9 includes the cathode 12, the electron transport layer 27, a photoelectric conversion layer 14, the hole transport layer 26, and the anode 11 that are stacked in this order on a substrate 25. With such a configuration, electrons generated in the pn junction interface of the photoelectric conversion layer 14 are transported to the cathode 12 through the electron transport layer 27, and the holes are transported to the anode 11 through the hole transport layer 26.

Figure 10:
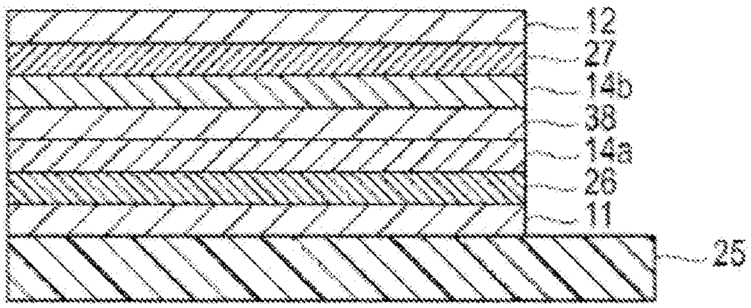
FIG. 10 is a cross-sectional view schematically illustrating an organic thin-film solar cell in accordance with Embodiment 10 of the present invention.

FIG. 10 is a cross-sectional view schematically illustrating an organic photoelectric conversion element including a tandem type (multijunction type) photoelectric conversion layer in accordance with Embodiment 10 of the present invention. The organic photoelectric conversion element shown in FIG. 10 includes, in place of the photoelectric conversion layer 14 of the organic photoelectric conversion element shown in FIG. 8, a lamination of a first photoelectric conversion layer 14*a*, a second photoelectric conversion layer 14*b*, and a charge recombination layer 38 interposed between these two photoelectric conversion layers. On this point, the organic photoelectric conversion element shown in FIG. 10 differs from the organic photoelectric conversion element shown in FIG. 8. The tandem type organic photoelectric conversion element shown in FIG. 10 may be configured such that the first photoelectric conversion layer 14*a* and the second photoelectric conversion layer 14*b* are made of photoelectric conversion materials (a p-type organic semiconductor and an n-type organic semiconductor) having different absorption wavelengths. This configuration makes it possible to efficiently convert light in a broader wavelength range into electricity.

The present invention is not limited to the embodiments described above, but can be altered by a skilled person in the art within the scope of the claims. The present invention also encompasses, in its technical scope, any embodiment derived by combining technical means disclosed in differing embodiments.

As described above, an embodiment of the present invention encompasses the inventions [1] to [8] below.

[1] A compound in accordance with a first aspect of the present invention is represented by a general formula (1).

(1)

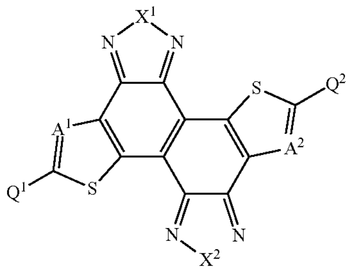

In the general formula (1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

$X^1$ and $X^2$ are each independently

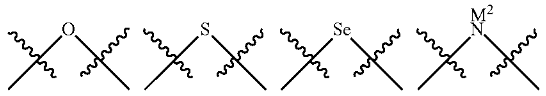

or

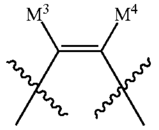

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

[2] A compound in accordance with a second aspect of the present invention is represented by a general formula (2).

(2)

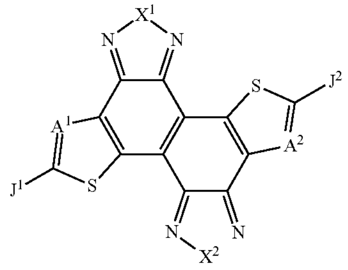

In the general formula (2), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$J^1$ and $J^2$ are each independently a skeleton giving an electron donating property or an electron accepting property;

$X^1$ and $X^2$ are each independently

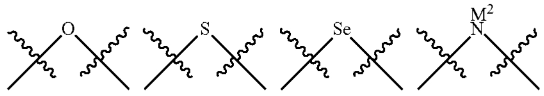

or

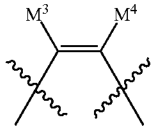

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

[3] The compound represented by the general formula (2) is more preferably a compound represented by a general formula (2-1).

(2-1)

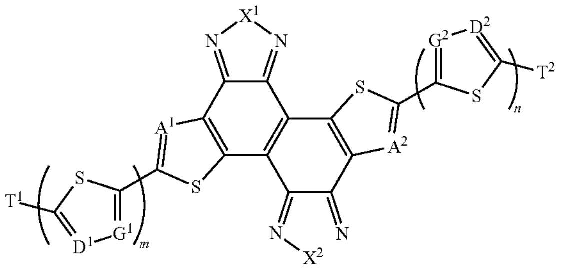

In the general formula (2-1), $A^1$, $A^2$, $X^1$, and $X^2$ are the same as those defined above, $D^1$, $D^2$, $G^1$, and $G^2$ are each independently $CM^1$ or N, and $M^1$ is the same as that defined above m and n are each independently 0 or a natural number, $T^1$ and $T^2$ are each independently

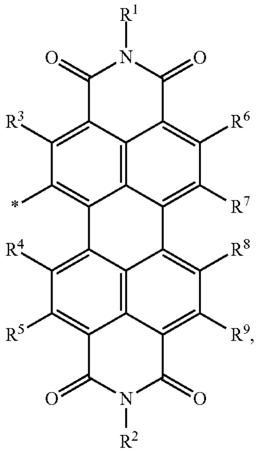

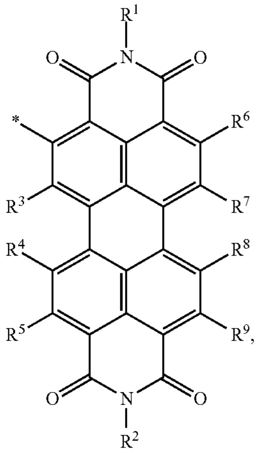

-continued

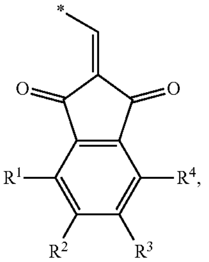

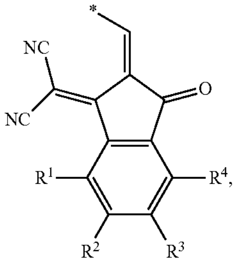

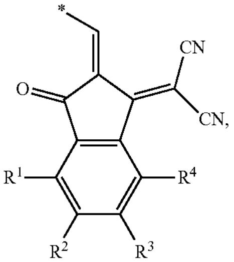

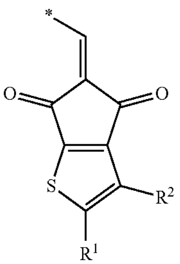

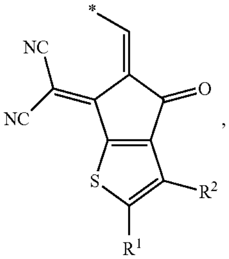

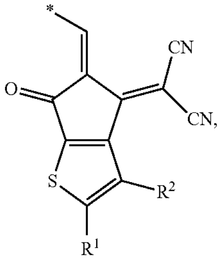

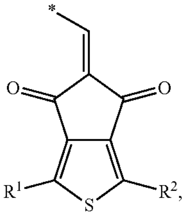

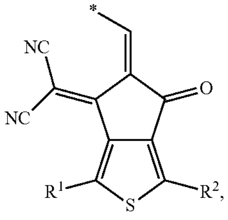

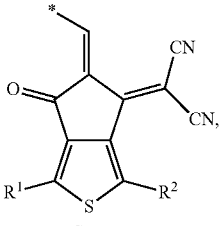

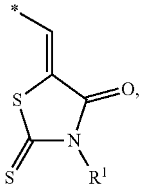

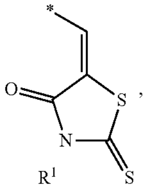

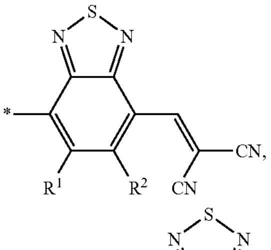

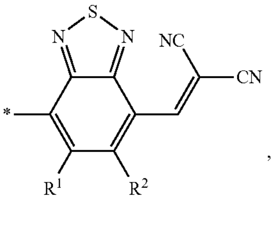

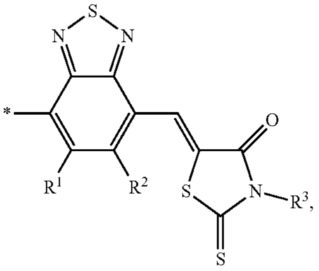

-continued

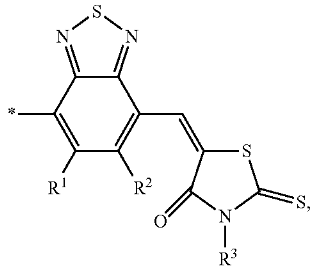

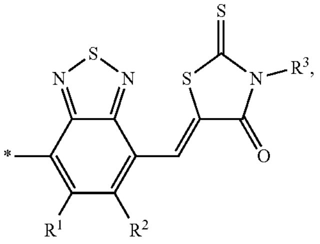

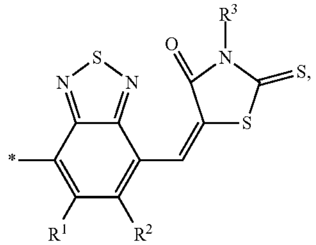

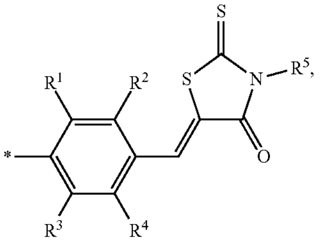

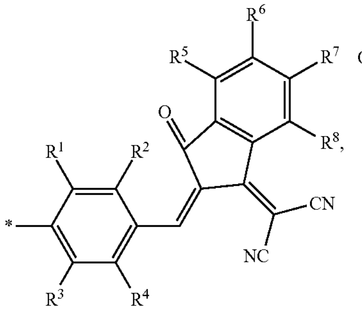

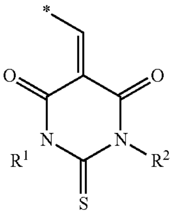

or

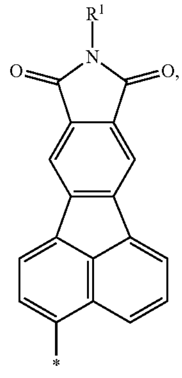

where: $R^1$ to $R^9$ are each independently a hydrogen atom, a halogen atom, an alkyl group, an alkoxy group, an alkoxy carbonyl group, an alkyl carbonyl group, or an aryl group; and * represents a bond.

[4] The compound represented by the general formula (2-1) is more preferably a compound represented by a general formula (2-2).

(2-2)

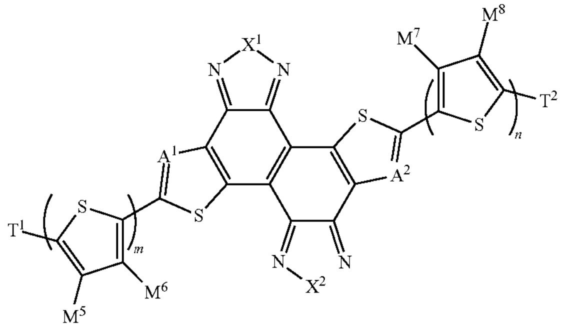

In the general formula (2-2), $A^1$, $A^2$, $T^1$, $T^2$, $X^1$, $X^2$, m, and n are the same as those defined above; and $M^5$ to $M^8$ are each independently a hydrogen atom, a halogen atom, an alkyl group, an alkoxy group, an alkoxy carbonyl group, an alkyl carbonyl group, or an aryl group.

[5] An organic semiconductor material in accordance with a third aspect of the present invention includes the compound in accordance with the first aspect or the second aspect of the present invention.

[6] An organic semiconductor device in accordance with a fourth aspect of the present invention includes the organic semiconductor material in accordance with the third aspect of the present invention.

[7] A method in accordance with a fifth aspect of the present invention for producing the compound represented by the general formula (1), the method being any of the following method (1), (2), (3), (4), (5), or (6):

the method (1) including:

(i) a step 1a of causing a compound represented by a general formula (A5) to react with trialkylsilylacetylene to produce a compound represented by a general formula (A6):

(A5)

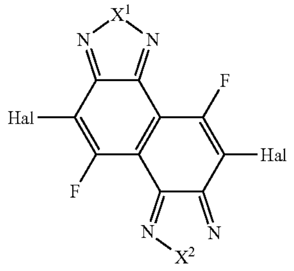

where, in the general formula (A5), each of Hals is independently a halogen atom; and $X^1$ and $X^2$ are the same as those defined above, (A6)

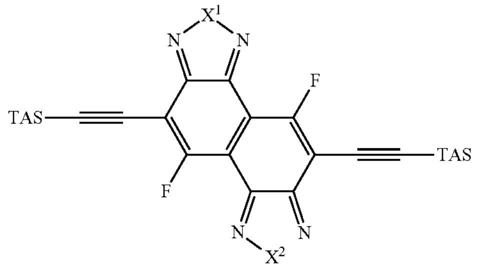

where, in the general formula (A6); TAS represents a trialkylsilyl group; and $X^1$ and $X^2$ are the same as those defined above;

(ii) a step 2a of causing the compound represented by the general formula (A6) obtained in the step 1a to react with a sulphurizing agent to produce a compound represented by a general formula (A7):

(A7)

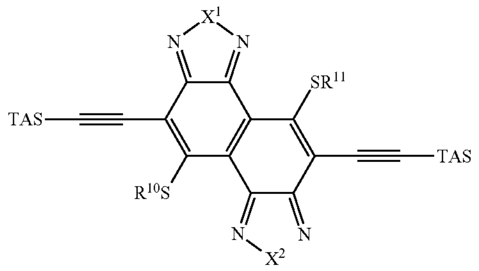

where, in the general formula (A7), TAS, $X^1$, and $X^2$ are the same as those defined above; and $R^{10}$ and $R^{11}$ are each independently an alkyl group optionally substituted with Z, and Z is the same as that defined above; and (iii) a step 3a of causing the compound represented by the general formula (A7) obtained in the step 2a to react with a halogenating agent to produce a compound represented by a general formula (1-1):

(1-1)

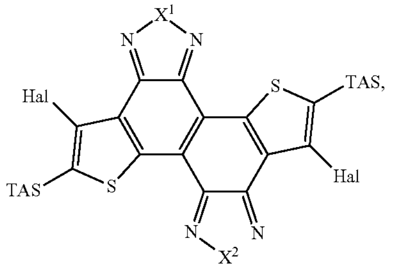

where, in the general formula (1-1), TAS, Hal, $X^1$, and $X^2$ are the same as those defined above, the general formula (1-1) being encompassed in the general formula (1);

the method (2) including:

a step 4a of causing the compound represented by the general formula (1-1) obtained in the step 3a to react with a boron compound to produce a compound represented by a general formula (1-2):

(1-2)

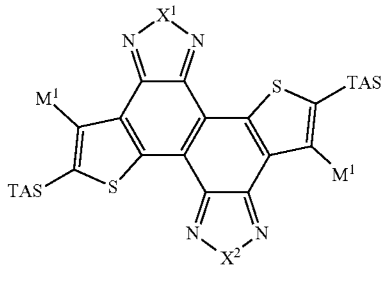

where, in the general formula (1-2), TAS, $M^1$, $X^1$, and $X^2$ are the same as those defined above, the general formula (1-2) being encompassed in the general formula (1);

the method (3) including:

a step 5a of causing the compound represented by the general formula (1-2) obtained in the step 4a to react with a halogenating agent to produce a compound represented by a general formula (1-3):

(1-3)

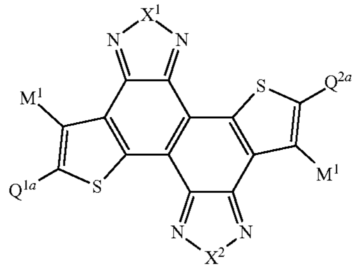

where, in the general formula (1-3), $M^1$, $X^1$, and $X^2$ are the same as those defined above; and $Q^{1a}$ and $Q^{2a}$ are each independently a halogen atom, the general formula (1-3) being encompassed in the general formula (1);

the method (4) including:

a step 6a of causing the compound represented by the general formula (1-3) to react with a boron compound or a tin compound to produce a compound represented by a general formula (1-4):

(1-4)

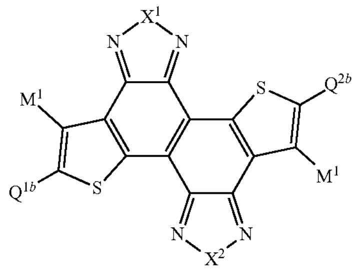

where, in the general formula (1-4), $M^1$, $X^1$, and $X^2$ are the same as those defined above; and $Q^{1b}$ and $Q^{2b}$ are each independently a hydrogen atom, an aryl group optionally substituted with Z, a heterocyclic group optionally substituted with Z, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group, the general formula (1-4) being encompassed in the general formula (1);

the method (5) including:

formylating the compound represented by the general formula (1-4) to produce a compound represented by a general formula (1-5):

(1-5)

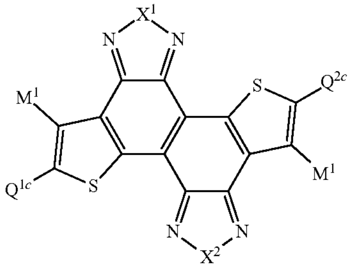

where, in the general formula (1-5), $M^1$, $X^1$, and $X^2$ are the same as those defined above; and $Q^{1c}$ and $Q^{2c}$ are each independently a formyl group;

the method (6) including:

(i) a step 1b of causing a compound represented by a general formula (A9) to react with a halogenating agent to produce a compound represented by a general formula (A10):

(A9)

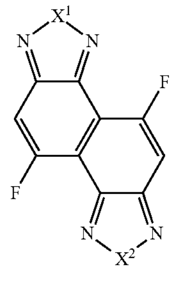

where, in the general formula (A9), $X^1$ and $X^2$ are the same as those defined above;

(A10)

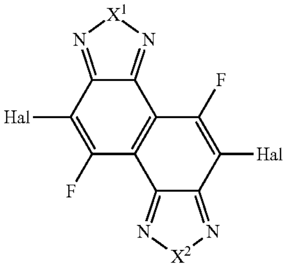

where, in the general formula (A10), $X^1$, $X^2$, and Hal are the same as those defined above;

(ii) a step 2b of causing the compound represented by the general formula (A10) obtained in the step 1b to react with an aminating agent to produce a compound represented by a general formula (A11):

(A11)

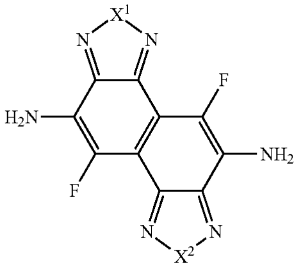

where, in the general formula (A11), $X^1$ and $X^2$ are the same as those defined above;

(iii) a step 3b of causing the compound represented by the general formula (A11) obtained in the step 2b to react with a compound represented by $Q^1$-$CO_2Cl$, where $Q^1$ is the same as that defined above, and a compound represented by $Q^2$-$CO_2Cl$, where $Q^2$ is the same as that defined above, to produce a compound represented by a general formula (A12):

(A12)

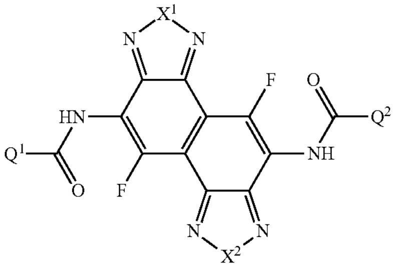

where, in the general formula (A12), $X^1$, $X^2$, $Q^1$, and $Q^2$ are the same as those defined above; and (iv) a step 4b of causing the compound represented by the general formula (A12) obtained in the step 3b to react with a sulphurizing agent to produce a compound represented by a general formula (1-6):

(1-6)

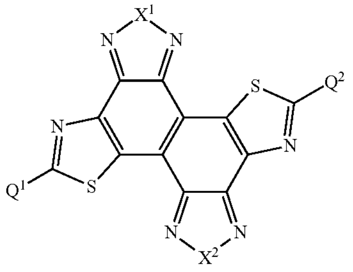

where, in the general formula (1-6), $X^1$, $X^2$, $Q^1$, and $Q^2$ are the same as those defined above, the general formula (1-6) being encompassed in the general formula (1).

[8] A method in accordance with a sixth aspect of the present invention for producing the compound represented by the general formula (2), the method including:

introducing, as $Q^1$ and $Q^2$ in the compound represented by the general formula (1), $J^1$ and $J^2$ each being a skeleton giving an electron donating property or an electron accepting property.

EXAMPLES

On the basis of the Examples, the following will provide a further detailed description of various methods for synthesizing a compound in accordance with an aspect of the present invention that constitutes an organic semiconductor material and characteristics of an organic solar cell as an organic semiconductor device including an organic semiconductor material containing the compound. The description on the synthesis methods and the characteristics is given to describe examples of the present invention, and the present invention is not limited to these Examples.

<Measurement Conditions, Etc.>

A nuclear magnetic resonance (NMR) spectrum was measured with use of JMM-ECS400 (product name) (400 MHz for 1-hour measurement) available from JEOL Ltd. A chemical shift is expressed in parts per million (ppm). Used as an internal standard (0 ppm) was tetramethylsilane (TMS). A coupling constant (J) is expressed in Herz, and abbreviations "s", "d" "t", "q", "m", and "br" denote a singlet, a doublet, a triplet, a quartet, a multiplet, and a broad, respectively. Mass spectroscopy (MALDI TOFMS) was carried out with AXIMA (product name) available from Shimadzu Corporation. Elementary analysis was carried out with JM10 (product name) available from J-Science Lab Co., Ltd. A silica gel used for separation by column chromatography was Silica Gel 60N (product name) (40 m to 50 m) available from Kanto Chemical Co., Inc. All chemical substances used in the Examples were of reagent-grade, and were purchased from Wako Pure Chemical Corporation, Tokyo Chemical Industry Co., Ltd., Kanto Chemical Co., Inc., Nacalai Tesque, Inc., and Sigma-Aldrich Japan.

Example 1

(Synthesis of Compound 1)

A compound 1 shown below was synthesized in accordance with the Examples described in International Publication No. WO 2018/123207.

(Synthesis of Compound 2)

To a 20-mL test tube, the compound 1 (172 mg, 0.393 mmol), tetrakis(triphenylphosphine)palladium (0) (45 mg, 0.039 mmol), copper iodide (7 mg, 0.04 mmol), triethylsilylacetylene (551 mg, 3.93 mmol), toluene (7 mL), and triethylamine (3.5 mL) were added to prepare a reaction liquid. Then, the gas in the test tube was replaced with nitrogen. Thereafter, the reaction liquid was stirred at 110° C. for 18 hours. After the reaction liquid was cooled to room temperature, chloroform was added to the reaction liquid and a resulting mixture was filtered with cerite. Then, the solvent therein was distilled off at reduced pressure. A reaction mixture thus obtained was refined through separation by silica-gel column chromatography employing, as a mobile phase, a hexane:methylene chloride (10:1) solvent, so that a compound 2 shown below was obtained (a yellowish brown solid, 170 mg, a yield of 78%). The reaction formula is shown below.

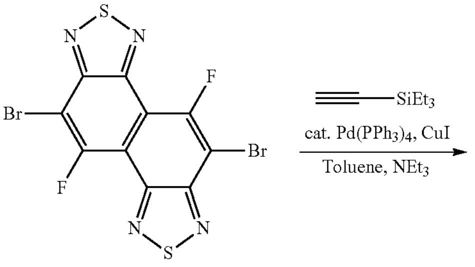

1

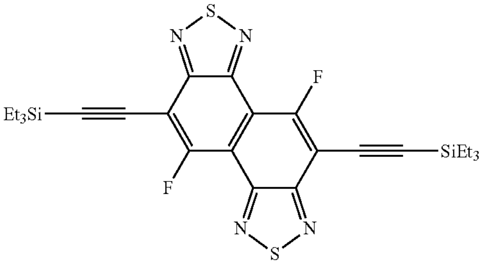

2

The physical properties of the compound 2 thus obtained were as shown below. $^1$H-NMR (400 MHz, $CDCl_3$, TMS) 6=1.15 (t, J=8.2 Hz, 18H), 0.81 (q, J=8.2 Hz, 12H).

(Synthesis of Compound 3)

To a 200-mL eggplant shaped flask, the compound 2 (186 mg, 0.334 mmol) and tetrahydrofuran (15 mL) were added, and the compound 2 was dissolved. Next, sodium thiomethoxide (70 mg, 1.0 mmol) was added thereto in ice bath, and stirred at 0° C. for three hours. Thereafter, ice water was added to the reaction liquid, and an organic layer was extracted with chloroform. Then, the organic layer was washed with a saturated salt solution and water. The organic layer was dried with anhydrous sodium sulfate, and filtered. Then, the solvent therein was distilled off at reduced pressure, so that a compound 3 shown below was obtained (a reddish brown solid, 170 mg, a yield of 83%). The reaction formula is shown below.

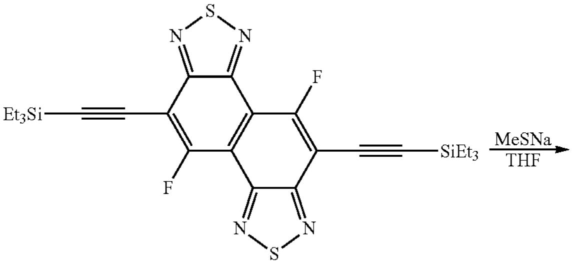

2

-continued

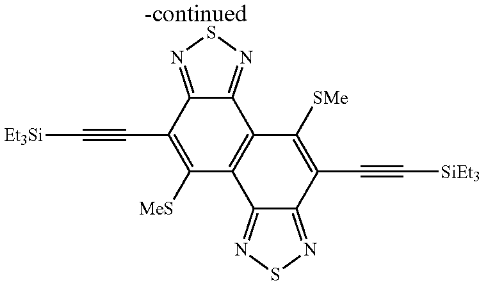

3

The physical properties o the compound us obtained were as s own below. $^1$H-NMR (400 MHz, $CDCl_3$, TMS) 6=2.76 (s, 6H), 1.17 (t, J=7.8 Hz, 18H), 0.83 (q, J=7.8 Hz, 12H).

(Synthesis of Compound 4)

To a 200-mL eggplant shaped flask, the compound 3 (170 mg, 0.277 mmol) and methylene chloride (50 mL) were added, and the compound 3 was dissolved. Next, iodine (353 mg, 1.39 mmol) was added thereto, and a resulting mixture was stirred at room temperature for 17 hours. Thereafter, the solvent therein was distilled off at reduced pressure. To a reaction mixture thus obtained, methanol was added. Then, a solid thus precipitated was filtered, and the solid was washed with methanol, so that a compound 4 shown below was obtained (a blown solid, 214 mg, a yield of 92%). The reaction formula is shown below.

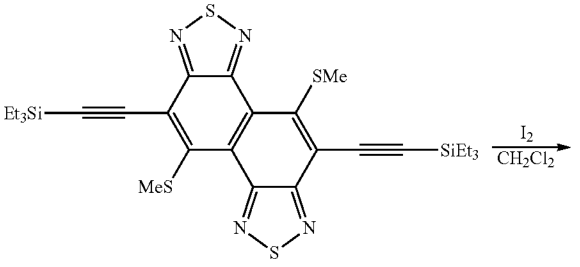

3

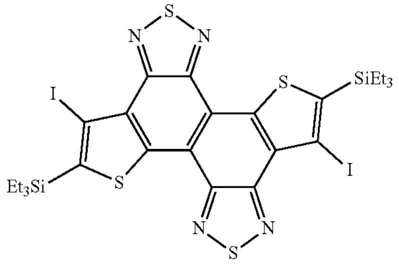

4

The physical properties of the compound 4 thus obtained were as shown below. $^1$H-NMR (400 MHz, $CDCl_3$, TMS) 6=1.24 (q, J=7.8 Hz, 12H), 1.11 (t, J=7.8 Hz, 18H).

(Synthesis of Compound 5)

To a 50-mL test tube, the compound 4 (221 mg, 0.252 mmol), octylboronic acid (199 mg, 1.26 mmol), SPhos (2-dicyclohexylphosphino-2',6'-dimethoxybiphenyl) (8 mg, 0.02 mmol), palladium acetate (2 mg, 0.01 mmol), and 10 mL of toluene were added to prepare a reaction liquid. Then, the gas in the test tube was replaced with nitrogen. Thereafter, the reaction liquid was stirred at 100° C. for 16 hours. After the reaction liquid was cooled to room temperature, water was added to the reaction liquid, and an organic layer was extracted with toluene. Then, the organic layer was washed with saturated salt solution and water. The organic layer was dried with anhydrous sodium sulfate, and filtered. Then, the solvent therein was distilled off at reduced pressure. A reaction mixture thus obtained was refined through separation by silica-gel column chromatography employing hexane as a mobile phase, so that a compound 5 shown below was obtained (a yellow solid, 94 mg, a yield of 46%). The reaction formula is shown below.

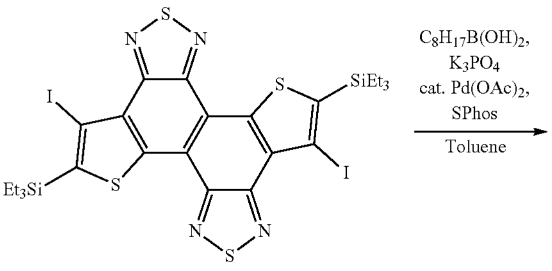

4

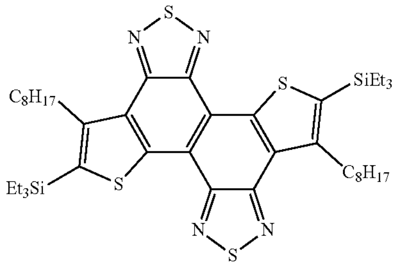

5

The physical properties of the compound 5 thus obtained were as shown below. $^1$HNMR (400 MHz, $CDCl_3$, TMS) 6=3.49-3.45 (m, 4H), 1.82-1.72 (m, 4H), 1.66-1.59 (m, 4H), 1.45-1.33 (m, 16H), 1.10 (s, 30H), 0.91 (t, J=7.0 Hz, 6H).

(Synthesis of Compound 6)

To a 100-mL eggplant shaped flask, the compound 5 (67 mg, 0.083 mmol) and chloroform (8 mL) were added, and the compound 5 was dissolved. Next, bromine (66 mg, 0.41 mmol) was added thereto. A resulting mixture was stirred at room temperature for 30 minutes, and then was stirred at 40° C. for an hour. A reaction liquid was cooled to room temperature, and then methanol was added to the reaction liquid. A reaction mixture thus obtained was filtered, and washed with methanol. so that a compound 6 shown below was obtained (a yellowish brown solid, 54 mg, a yield of 88%). The reaction formula is shown below.

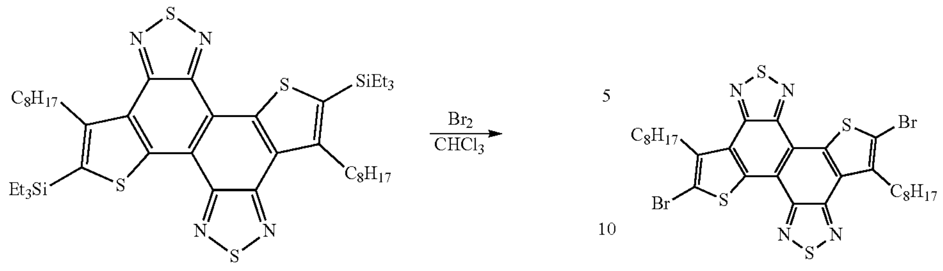

5 6

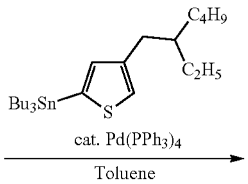

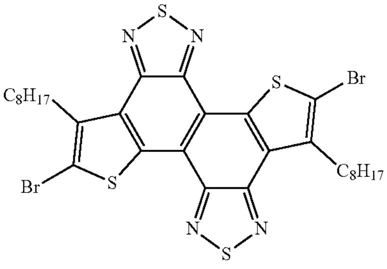

6

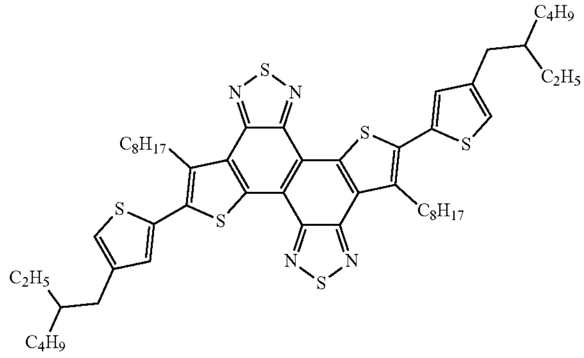

7

The physical properties of the compound 6 thus obtained were as shown below. ¹H-NMR (400 MHz, $CDCl_3$, TMS) 6=3.42 (t, J=7.8 Hz, 4H), 1.77 (q, 7.8 Hz, 4H), 1.44-1.24 (m, 16H), 0.89 (t, J=7.0 Hz, 6H). MS (MALDI) m/z=737.79 ($M^+$).

(Synthesis of Compound 7)

To a reaction container, the compound 6 (30 mg, 0.04 mmol), 4-(2-ethylhexyl)-2-tributylstannylthiophene (60 mg, 0.12 mmol), tetrakis(triphenylphosphine)palladium (0) (5 mg, 0.004 mmol) that is a catalyst, and toluene (2 mL) were added to prepare a reaction liquid. Then, the gas in the test tube was replaced with nitrogen. Thereafter, the reaction liquid was reacted at 180° C. for 10 minutes with use of a μ-wave reactor. After the reaction liquid was cooled to room temperature, water was added to the reaction liquid, and an organic layer was extracted with chloroform. Then, the organic layer was washed with saturated salt solution and water. The organic layer was dried with anhydrous sodium sulfate, and filtered. Then, the solvent therein was distilled off at reduced pressure. A reaction mixture thus obtained was refined through separation by silica-gel column chromatography employing hexane/chloroform as a mobile phase, so that a compound 7 shown below was obtained (a red solid, 30 mg, a yield of 75%). The reaction formula is shown below.

The physical properties of the compound 7 thus obtained were as shown below. ¹H-NMR (400 MHz, $CDCl_3$, TMS) 6=7.19 (s, 2H), 7.02 (s, 2H), 3.43-3.35 (m, 4H), 2.69-2.60 (m, 4H), 1.80-1.65 (m, 6H), 1.5-1.2 (m, 36H), 1.0-0.89 (m, 18H).

(Synthesis of Compound 8)

To a reaction container, the compound 7 (30 mg, 0.03 mmol) and 1,2-dichloroethane (3 mL) were added so as to prepare a reaction liquid. Next, the reaction liquid is cooled to 0° C., and then N,N-dimethylformamide (68 mg) and phosphoryl chloride (120 mg, 0.80 mmol) were added thereto in ice bath. Thereafter, the temperature of the reaction liquid was increased to 95° C., and the reaction liquid was reacted for 12 hours. After the reaction liquid was cooled to room temperature, water was added to the reaction liquid, and an organic layer was extracted with chloroform. Then, the organic layer was washed with saturated salt solution and water. The organic layer was dried with anhydrous sodium sulfate, and filtered. Then, the solvent therein was distilled off at reduced pressure. A reaction mixture thus obtained was refined through separation by silica-gel column chromatography employing hexane/chloroform as a mobile phase, so that a compound 8 shown below was obtained (an orange solid, 25 mg, a yield of 80%). The reaction formula is shown below.

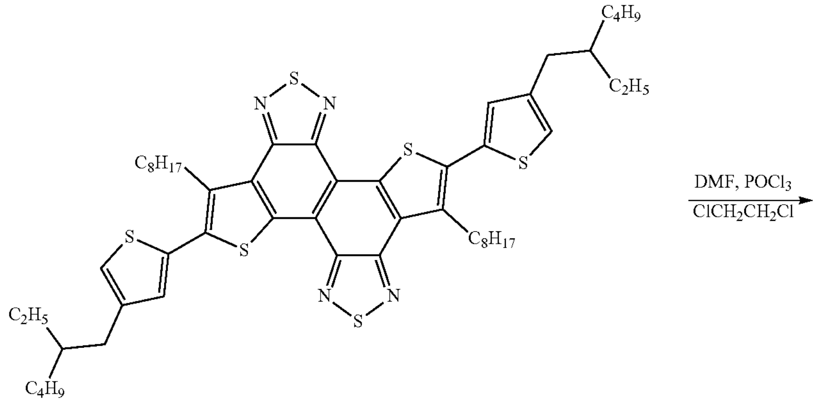

7

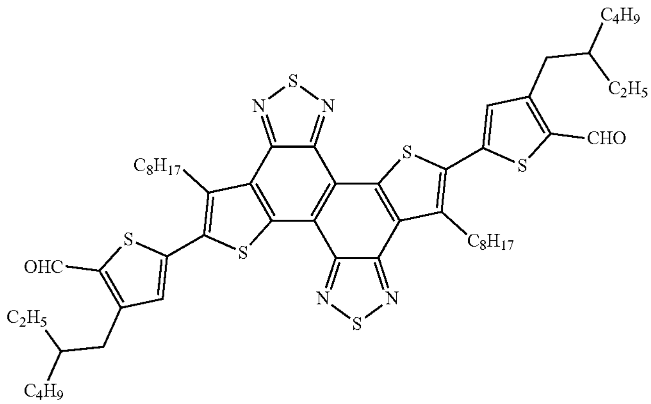

8

The physical properties of the compound 8 thus obtained were as shown below. $^1$H-NMR (400 MHz, $CDCl_3$, TMS) 6=10.06 (s, 2H), 7.19 (s, 2H), 3.35 (t, J=8.0 Hz, 4H), 2.93 (d, J=6.8 Hz, 2H), 1.8-1.2 (m, 36H), 1.0-0.90 (m, 18H).

(Synthesis of Compound 9)

To a reaction container, the compound 8 (25 mg, 0.02 mmol), 3-ethylrhodanine (24 mg, 0.15 mmol), and chloroform (2 mL) were added so as to prepare a reaction liquid. Next, one drop of piperidine was added to the reaction liquid, and then the gas in the reaction container was replaced with nitrogen. Thereafter, the reaction liquid was refluxed for 12 hours. After the reaction liquid was cooled to room temperature, water was added to the reaction liquid, and an organic layer was extracted with chloroform. Then, the organic layer was washed with saturated salt solution and water. The organic layer was dried with anhydrous sodium sulfate, and filtered. Then, the solvent therein was distilled off at reduced pressure. A reaction mixture thus obtained was refined through separation by silica-gel column chromatography employing chloroform as a mobile phase. Then, methanol was added thereto for reprecipitation. Consequently, a compound 9 shown below was obtained (an orange solid, 20 mg, a yield of 65%). The reaction formula is shown below.

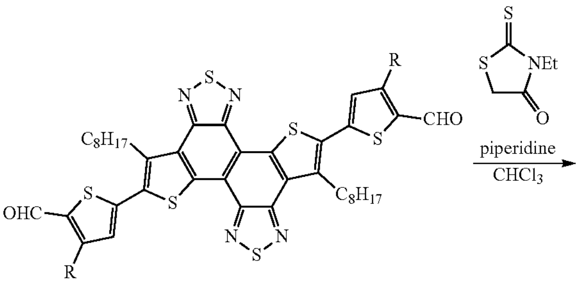

8
(R = 2-ethylhexyl)

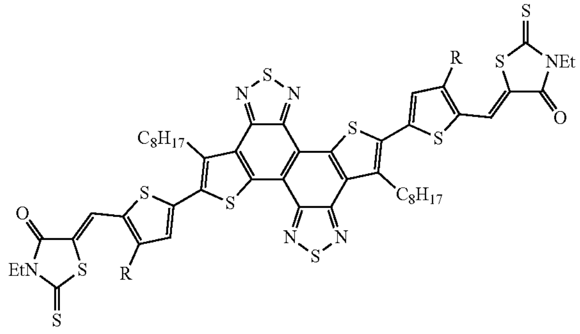

9
(R = 2-ethylhexyl)

The physical properties of the compound 9 thus obtained were as shown below. $^1$H-NMR (400 MHz, $CDCl_3$, TMS) δ=7.95 (s, 2H), 7.37 (s, 2H), 4.3-4.2 (m, 4H), 2.79 (d, J=7.2 Hz, 4H), 2.0-1.8 (m, 6H), 1.8-1.6 (m, 6H), 1.4-1.2 (m, 40H), 1.00-0.80 (m, 18H). MS (MALDI) m/z=1311.68 ($M^+$).

Example 2

(Synthesis of Compound 11)

To a reaction container, the compound 9 (12 mg, 0.016 mmol), the compound 10 (18 mg, 0.036 mmol), a 1 mol/L aqueous potassium carbonate solution (0.2 mL, 0.2 mmol), tetrakis(triphenylphosphine)palladium (0) (2 mg, 0.002 mmol) that is a catalyst, and toluene (2 mL) were added to prepare a reaction liquid. Then, the gas in the test tube was replaced with nitrogen. Thereafter, the reaction liquid was reacted at 150° C. for 10 minutes with use of a μ-wave reactor. The reaction liquid was cooled to room temperature. Thereafter, water was added to the reaction liquid, and an organic layer was extracted with chloroform. Then, the organic layer was washed with saturated salt solution and water. The organic layer was dried with anhydrous sodium sulfate, and filtered. Then, the solvent therein was distilled off at reduced pressure. A reaction mixture thus obtained was refined through separation by silica-gel column chromatography employing hexane/chloroform as a mobile phase, so that a compound 11 shown below was obtained (an orange solid, 10 mg, a yield of 48%). The reaction formula is shown below.

The physical properties of the compound 11 thus obtained were as shown below. $^1$H-NMR (400 MHz, $CDCl_3$, TMS) δ=8.23 (s, 2H), 8.11-8.08 (m, 4H), 8.04-7.96 (m, 2H), 7.95-7.87 (m, 2H), 7.83 (d, J=7.2 Hz, 2H), 7.60-7.52 (m, 2H), 4.45-4.36 (m, 2H), 3.40-3.20 (m, 4H), 2.18-2.06 (m, 2H), 1.88-1.76 (m, 2H), 1.70-1.58 (m, 8H), 1.42-0.92 (m, 28H), 0.88-0.85 (m, 6H), 0.70 (t, J=7.2 Hz, 6H).

<Orbital Energies of Highest Occupied Molecular Orbital and Lowest Unoccupied Molecular Orbital>

Next, orbital energies of highest occupied molecular orbitals (hereinafter, occasionally referred to as "HOMO") and lowest unoccupied molecular orbitals (hereinafter, occasionally referred to as "LUMO") of basic skeletons (i-1) to (i-20) shown below encompassed in the compound in accordance with the aspect of the present invention, represented by the general formula (1), were calculated. The results thereof are shown in Table 1.

The calculation method and condition: The lowest unoccupied molecular orbitals were calculated by a DFT method (density functional theory). For a basic function and a functional, the following function was used.

B3LYP/6-31G (d, p)

i-1

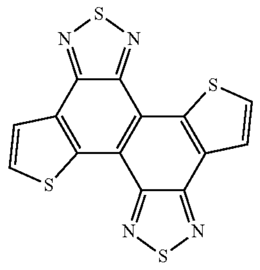

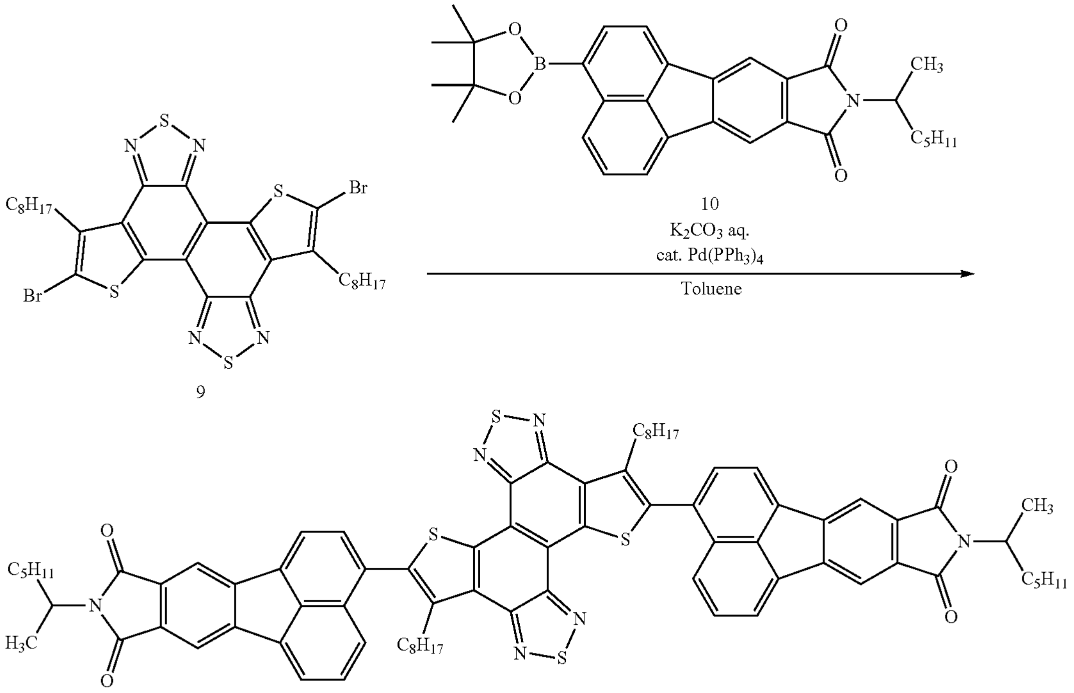

9

10

11

-continued
i-2
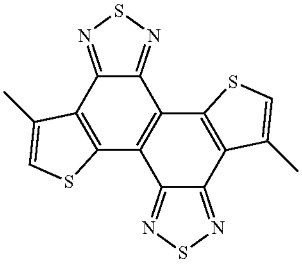
i-3
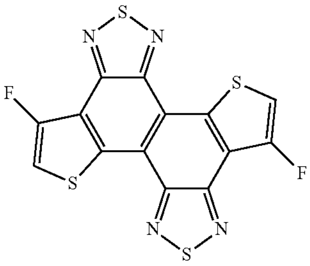
i-4
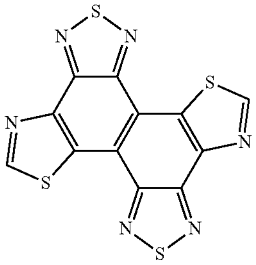
i-5
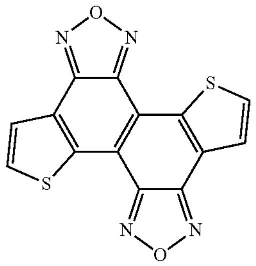
i-6
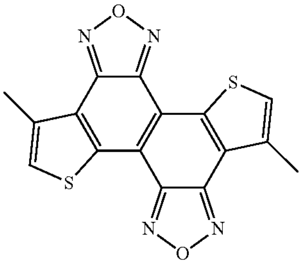
i-7
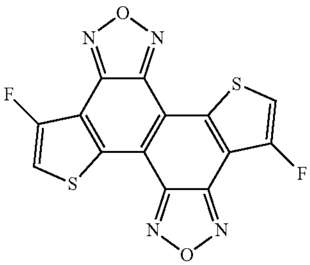
-continued
i-8
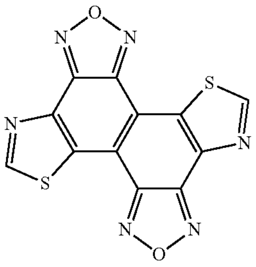
i-9
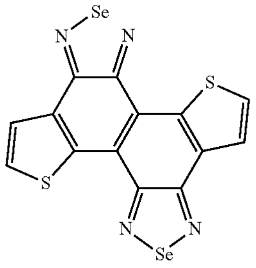
i-10
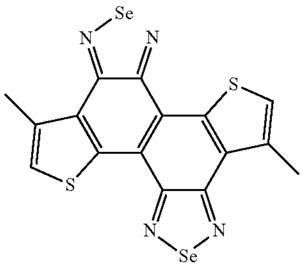
i-11
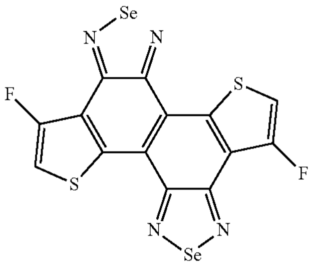
i-12
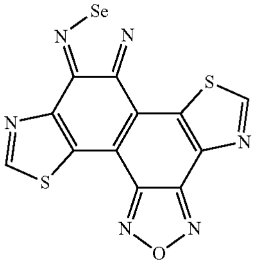

-continued i-13

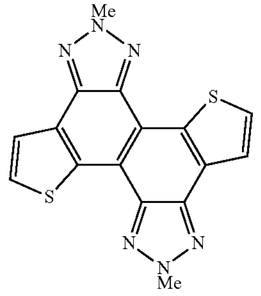

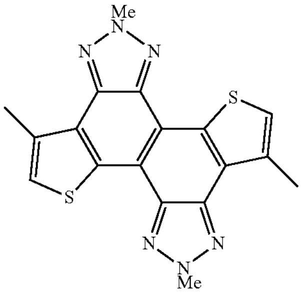

i-15

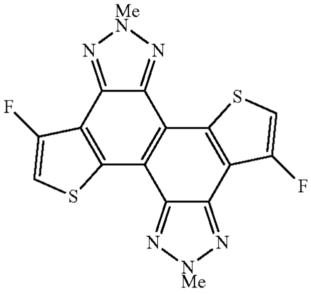

i-16

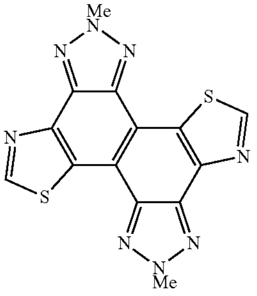

i-17

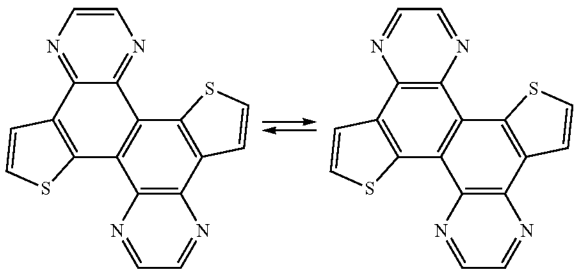

-continued i-18

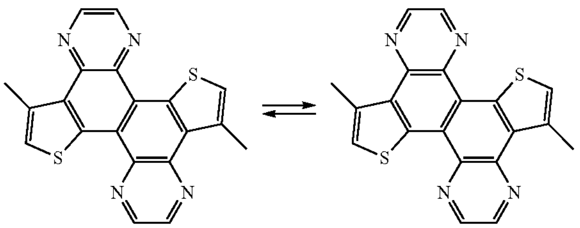

i-19

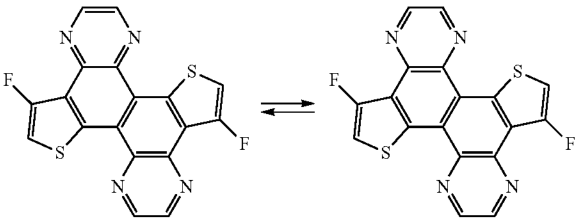

i-20

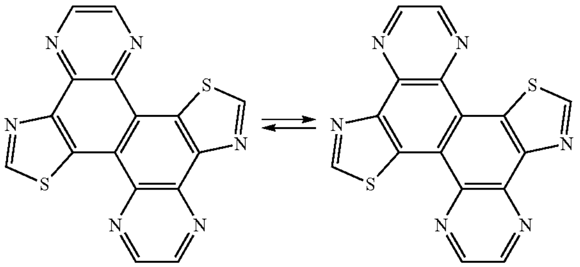

TABLE 1

| Compound | LUMO (eV) | HOMO (eV) | Compound | LUMO (eV) | HOMO (eV) |
|---|---|---|---|---|---|
| i-1 | −2.83 | −5.86 | i-2 | −2.76 | −5.72 |
| i-3 | −3.04 | −6.06 | i-4 | −3.09 | −6.34 |
| i-5 | −3.07 | −6.22 | i-6 | −2.98 | −6.06 |
| i-7 | −3.32 | −6.44 | i-8 | −3.40 | −6.73 |
| i-9 | −2.89 | −5.73 | i-10 | −2.83 | −5.60 |
| i-11 | −3.09 | −5.93 | i-12 | −3.14 | −6.17 |
| i-13 | −1.73 | −5.41 | i-14 | −1.66 | −5.30 |
| i-15 | −1.99 | −5.64 | i-16 | −2.04 | −5.85 |
| i-17 | −2.38 | −5.58 | i-18 | −2.58 | −5.87 |
| i-19 | −2.22 | −5.63 | i-20 | −2.60 | −6.22 |

Next, an organic solar cell was produced with use of the compound 9 synthesized, and performances thereof, such as a photoelectric conversion efficiency, were evaluated. The compound 9 is encompassed in the compound in accordance with the aspect of the present invention, represented by the general formula (2). Examples of the compound represented by the general formula (2) encompass compounds shown in Table 2 below. These compounds can be produced in accordance with the above-described method for producing the compound (2) and the methods described in Examples 1 and 2. In Table 2, Me is a methyl group, Et is an ethyl group, and * is a bond. Similarly to the above-described (i-17) to (i-20), each of the compounds (2)-11, (2)-12, (2)-23, and (2)-24 can be expressed in two patterns due to resonance of electrons. However, in Table 2, each of these compounds is representatively expressed in one of the two patterns, as well as in other parts of the specification of the present application.

TABLE 2

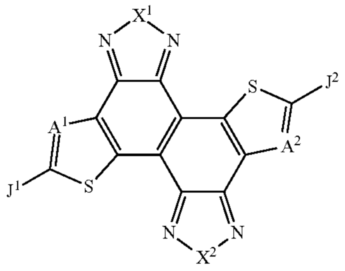

(2)

| No. | $X^1$ | $X^2$ | $A^1$ | $A^2$ | $J^1$ | $J^2$ | Phys. Prop. |
|---|---|---|---|---|---|---|---|
| (2)-1 (Comp. 9) | —S— | —S— | $C—C_8H_{17}$ | $C—C_8H_{17}$ | 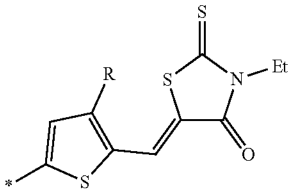 (R = 2-ethylhexyl) | 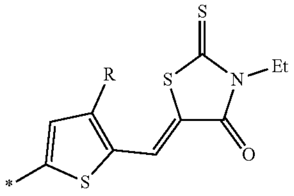 (R = 2-ethylhexyl) | Orange Solid |
| (2)-2 | —S— | —S— | N | N | Same as above | Same as above | |
| (2)-3 | —O— | —O— | $C—C_8H_{17}$ | $C—C_8H_{17}$ | Same as above | Same as above | |
| (2)-4 | —O— | —O— | N | N | Same as above | Same as above | |
| (2)-5 | —Se— | —Se— | $C—C_8H_{17}$ | $C—C_8H_{17}$ | Same as above | Same as above | |
| (2)-6 | —Se— | —Se— | N | N | Same as above | Same as above | |
| (2)-7 | —Se— | —O— | $C—C_8H_{17}$ | $C—C_8H_{17}$ | Same as above | Same as above | |
| (2)-8 | —Se— | —O— | N | N | Same as above | Same as above | |
| (2)-9 | MeN═ | MeN═ | $C—C_8H_{17}$ | $C—C_8H_{17}$ | Same as above | Same as above | |
| (2)-10 | MeN═ | MeN═ | N | N | Same as above | Same as above | |
| (2)-11 | —C═C— | | $C—C_8H_{17}$ | $C—C_8H_{17}$ | Same as above | Same as above | |
| (2)-12 | —C═C— | | N | N | Same as above | Same as above | |
| (2)-13 (Comp. 11) | —S— | —S— | $C—C_8H_{17}$ | $C—C_8H_{17}$ | 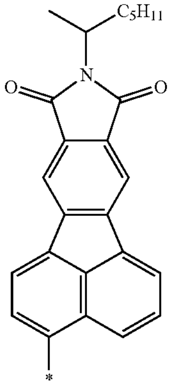 | 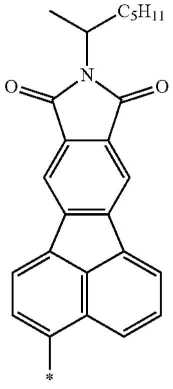 | Orange Solid |
| (2)-14 | —S— | —S— | N | N | Same as above | Same as above | |
| (2)-15 | —O— | —O— | $C—C_8H_{17}$ | $C—C_8H_{17}$ | Same as above | Same as above | |
| (2)-16 | —O— | —O— | N | N | Same as above | Same as above | |
| (2)-17 | —Se— | —Se— | $C—C_8H_{17}$ | $C—C_8H_{17}$ | Same as above | Same as above | |
| (2)-18 | —Se— | —Se— | N | N | Same as above | Same as above | |
| (2)-19 | —Se— | —O— | $C—C_8H_{17}$ | $C—C_8H_{17}$ | Same as above | Same as above | |
| (2)-20 | —Se— | —O— | N | N | Same as above | Same as above | |
| (2)-21 | MeN═ | MeN═ | $C—C_8H_{17}$ | $C—C_8H_{17}$ | Same as above | Same as above | |
| (2)-22 | MeN═ | MeN═ | N | N | Same as above | Same as above | |
| (2)-23 | —C═C— | | $C—C_8H_{17}$ | $C—C_8H_{17}$ | Same as above | Same as above | |
| (2)-24 | —C═C— | | N | N | Same as above | Same as above | |

TABLE 2-continued (2)

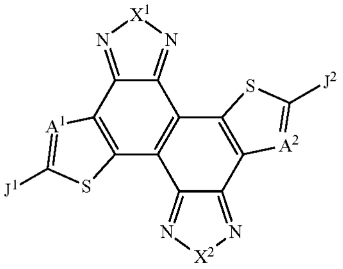

| No. | $X^1$ | $X^2$ | $A^1$ | $A^2$ | $J^1$ | $J^2$ | Phys. Prop. |
|---|---|---|---|---|---|---|---|
| (2)-25 | —S— | —S— | $C—C_8H_{17}$ | $C—C_8H_{17}$ | 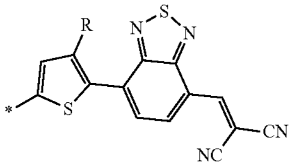 (R = 2-ethylhexyl) | 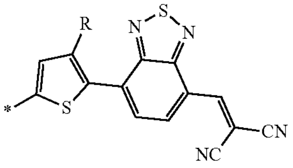 (R = 2-ethylhexyl) | |
| (2)-26 | —S— | —S— | N | N | Same as above | Same as above | |
| (2)-27 | —O— | —O— | $C—C_8H_{17}$ | $C—C_8H_{17}$ | Same as above | Same as above | |
| (2)-28 | —O— | —O— | N | N | Same as above | Same as above | |
| (2)-29 | —Se— | —Se— | $C—C_8H_{17}$ | $C—C_8H_{17}$ | Same as above | Same as above | |
| (2)-30 | —Se— | —Se— | N | N | Same as above | Same as above | |
| (2)-31 | —Se— | —O— | $C—C_8H_{17}$ | $C—C_8H_{17}$ | Same as above | Same as above | |
| (2)-32 | —Se— | —O— | N | N | Same as above | Same as above | |
| (2)-33 | MeN═ | MeN═ | $C—C_8H_{17}$ | $C—C_8H_{17}$ | Same as above | Same as above | |
| (2)-34 | MeN═ | MeN═ | N | N | Same as above | Same as above | |
| (2)-35 | —C═C— | | $C—C_8H_{17}$ | $C—C_8H_{17}$ | Same as above | Same as above | |
| (2)-36 | —C═C— | | N | N | Same as above | Same as above | |
| (2)-37 | —S— | —S— | $C—C_8H_{17}$ | $C—C_8H_{17}$ | 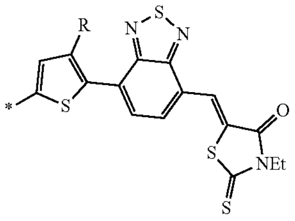 (R = 2-ethylhexyl) | 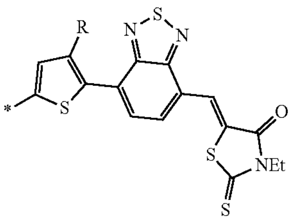 (R = 2-ethylhexyl) | |
| (2)-38 | —S— | —S— | N | N | Same as above | Same as above | |
| (2)-39 | —O— | —O— | $C—C_8H_{17}$ | $C—C_8H_{17}$ | Same as above | Same as above | |
| (2)-40 | —O— | —O— | N | N | Same as above | Same as above | |
| (2)-41 | —Se— | —Se— | $C—C_8H_{17}$ | $C—C_8H_{17}$ | Same as above | Same as above | |
| (2)-42 | —Se— | —Se— | N | N | Same as above | Same as above | |
| (2)-43 | —Se— | —O— | $C—C_8H_{17}$ | $C—C_8H_{17}$ | Same as above | Same as above | |
| (2)-44 | —Se— | —O— | N | N | Same as above | Same as above | |
| (2)-45 | MeN═ | MeN═ | $C—C_8H_{17}$ | $C—C_8H_{17}$ | Same as above | Same as above | |
| (2)-46 | MeN═ | MeN═ | N | N | Same as above | Same as above | |
| (2)-47 | —C═C— | | $C—C_8H_{17}$ | $C—C_8H_{17}$ | Same as above | Same as above | |
| (2)-48 | —C═C— | | N | N | Same as above | Same as above | |
| (2)-49 | —S— | —S— | $C—C_8H_{17}$ | $C—C_8H_{17}$ | 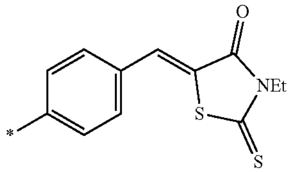 | 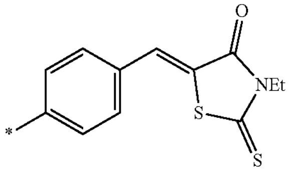 | |
| (2)-50 | —S— | —S— | N | N | Same as above | Same as above | |
| (2)-51 | —O— | —O— | $C—C_8H_{17}$ | $C—C_8H_{17}$ | Same as above | Same as above | |
| (2)-52 | —O— | —O— | N | N | Same as above | Same as above | |
| (2)-53 | —Se— | —Se— | $C—C_8H_{17}$ | $C—C_8H_{17}$ | Same as above | Same as above | |
| (2)-54 | —Se— | —Se— | N | N | Same as above | Same as above | |
| (2)-55 | —Se— | —O— | $C—C_8H_{17}$ | $C—C_8H_{17}$ | Same as above | Same as above | |

TABLE 2-continued (2)

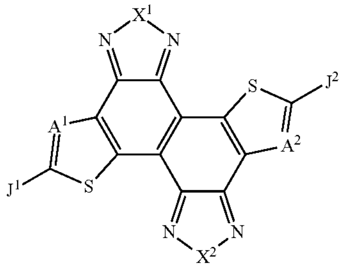

| No. | $X^1$ | $X^2$ | $A^1$ | $A^2$ | $J^1$ | $J^2$ | Phys. Prop. |
|---|---|---|---|---|---|---|---|
| (2)-56 | —Se— | —O— | N | N | Same as above | Same as above | |
| (2)-57 | MeN= | MeN= | C—$C_8H_{17}$ | C—$C_8H_{17}$ | Same as above | Same as above | |
| (2)-58 | MeN= | MeN= | N | N | Same as above | Same as above | |
| (2)-59 | —C=C— | | C—$C_8H_{17}$ | C—$C_8H_{17}$ | Same as above | Same as above | |
| (2)-60 | —C=C— | | N | N | Same as above | Same as above | |
| (2)-61 | —S— | —S— | C—$C_8H_{17}$ | C—$C_8H_{17}$ | 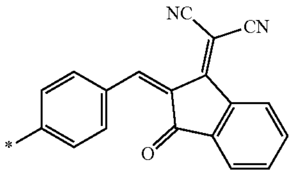 [SMILES: *c1ccc(/C=C2\C(=O)c3ccccc3C2=C(C#N)C#N)cc1] | 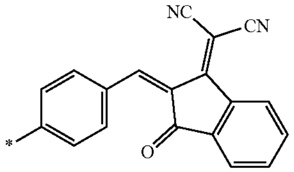 [SMILES: *c1ccc(/C=C2\C(=O)c3ccccc3C2=C(C#N)C#N)cc1] | |
| (2)-62 | —S— | —S— | N | N | Same as above | Same as above | |
| (2)-63 | —O— | —O— | C—$C_8H_{17}$ | C—$C_8H_{17}$ | Same as above | Same as above | |
| (2)-64 | —O— | —O— | N | N | Same as above | Same as above | |
| (2)-65 | —Se— | —Se— | C—$C_8H_{17}$ | C—$C_8H_{17}$ | Same as above | Same as above | |
| (2)-66 | —Se— | —Se— | N | N | Same as above | Same as above | |
| (2)-67 | —Se— | —O— | C—$C_8H_{17}$ | C—$C_8H_{17}$ | Same as above | Same as above | |
| (2)-68 | —Se— | —O— | N | N | Same as above | Same as above | |
| (2)-69 | MeN= | MeN= | C—$C_8H_{17}$ | C—$C_8H_{17}$ | Same as above | Same as above | |
| (2)-70 | MeN= | MeN= | N | N | Same as above | Same as above | |
| (2)-71 | —C=C— | | C—$C_8H_{17}$ | C—$C_8H_{17}$ | Same as above | Same as above | |
| (2)-72 | —C=C— | | N | N | Same as above | Same as above | |
| (2)-73 | —S— | —S— | C—$C_8H_{17}$ | C—$C_8H_{17}$ | 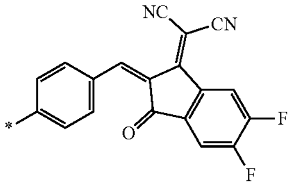 [SMILES: *c1ccc(/C=C2\C(=O)c3cc(F)c(F)cc3C2=C(C#N)C#N)cc1] | 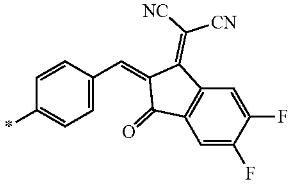 [SMILES: *c1ccc(/C=C2\C(=O)c3cc(F)c(F)cc3C2=C(C#N)C#N)cc1] | |
| (2)-74 | —S— | —S— | N | N | Same as above | Same as above | |
| (2)-75 | —O— | —O— | C—$C_8H_{17}$ | C—$C_8H_{17}$ | Same as above | Same as above | |
| (2)-76 | —O— | —O— | N | N | Same as above | Same as above | |
| (2)-77 | —Se— | —Se— | C—$C_8H_{17}$ | C—$C_8H_{17}$ | Same as above | Same as above | |
| (2)-78 | —Se— | —Se— | N | N | Same as above | Same as above | |
| (2)-79 | —Se— | —O— | C—$C_8H_{17}$ | C—$C_8H_{17}$ | Same as above | Same as above | |
| (2)-80 | —Se— | —O— | N | N | Same as above | Same as above | |
| (2)-81 | MeN= | MeN= | C—$C_8H_{17}$ | C—$C_8H_{17}$ | Same as above | Same as above | |
| (2)-82 | MeN= | MeN= | N | N | Same as above | Same as above | |
| (2)-83 | —C=C— | | C—$C_8H_{17}$ | C—$C_8H_{17}$ | Same as above | Same as above | |
| (2)-84 | —C=C— | | N | N | Same as above | Same as above | |
| (2)-85 | —S— | —S— | C—$C_8H_{17}$ | C—$C_8H_{17}$ | 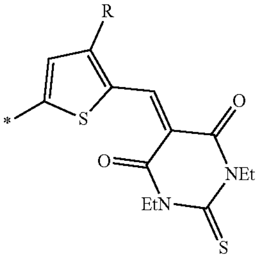<br>(R = 2-ethylhexyl) | 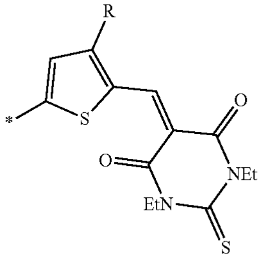<br>(R = 2-ethylhexyl) | |

TABLE 2-continued (2)

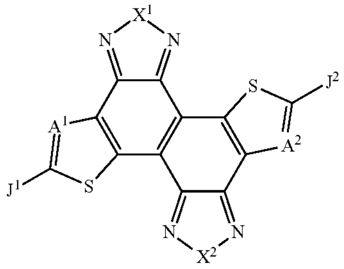

| No. | $X^1$ | $X^2$ | $A^1$ | $A^2$ | $J^1$ | $J^2$ | Phys. Prop. |
|---|---|---|---|---|---|---|---|
| (2)-86 | —S— | —S— | N | N | Same as above | Same as above | |
| (2)-87 | —O— | —O— | C—$C_8H_{17}$ | C—$C_8H_{17}$ | Same as above | Same as above | |
| (2)-88 | —O— | —O— | N | N | Same as above | Same as above | |
| (2)-89 | —Se— | —Se— | C—$C_8H_{17}$ | C—$C_8H_{17}$ | Same as above | Same as above | |
| (2)-90 | —Se— | —Se— | N | N | Same as above | Same as above | |
| (2)-91 | —Se— | —O— | C—$C_8H_{17}$ | C—$C_8H_{17}$ | Same as above | Same as above | |
| (2)-92 | —Se— | —O— | N | N | Same as above | Same as above | |
| (2)-93 | MeN═ | MeN═ | C—$C_8H_{17}$ | C—$C_8H_{17}$ | Same as above | Same as above | |
| (2)-94 | MeN═ | MeN═ | N | N | Same as above | Same as above | |
| (2)-95 | —C═C— | | C—$C_8H_{17}$ | C—$C_8H_{17}$ | Same as above | Same as above | |
| (2)-96 | —C═C— | | N | N | Same as above | Same as above | |

"Comp." stands for "compound".
"Phys. Prop." stands for "physical property".

Example 3

(Evaluation of Performance of Organic Solar Cell)

An organic solar cell was produced with use of the synthesized compound 9 as the n-type organic semiconductor material. Then, evaluation was conducted on the organic solar cell thus obtained.

Used as the substrate was a glass substrate. Used as the p-type organic semiconductor material was P3HT (poly(3-hexilthiophene)). Used as the electrodes were ITO (cathode) and aluminum (anode). Used as the hole transport material was PEDOT:PSS (poly(3,4-ethylenedioxythiophene) doped with poly(4-styrene sulfonate)). Used as the electron transport material was Ca. A solution was prepared in advance by dissolving P3HT (20 mg) and the compound 9 (20 mg) in chloroform (1 mL).

First, the glass substrate on which the ITO film was patterned was subjected to ultrasonic washing with toluene, acetone, water, and isopropanol in order each for 15 minutes. Thereafter, the glass substrate was put into a plasma cleaning machine. Then, an oxygen gas was introduced into the plasma cleaning machine, and the surface of the glass substrate was washed with generated plasma for 20 minutes. Furthermore, the glass substrate was subjected to ozone UV irradiation for 90 minutes so that the surface of the glass substrate was washed. Then, a PEDOT:PSS thin film was formed on the ITO film by a spin-coating film forming device. Next, the glass substrate was subjected to annealing at 135° C. for 10 minutes. A PEDOT:PSS thin film thus formed was 30 nm. In addition, spin-coating of the above-described solution, which was prepared in advance, was carried out onto the PEDOT:PSS thin film by the spin-coating film forming device (at 3000 rpm, for 1 minute), so that an organic semiconductor layer was formed. In this manner, a lamination was obtained. Thereafter, the lamination was subjected to annealing at 120° C. for 10 minutes. Subsequently, the lamination thus obtained was placed on a mask of a small, high-vacuum vapor deposition device, and a film of Ca (20 nm) serving as the electron transport layer and an aluminum layer (80 nm) serving as the metal electrode were formed in order. Consequently, an organic solar cell of 3 mm square was obtained.

Figure 11:
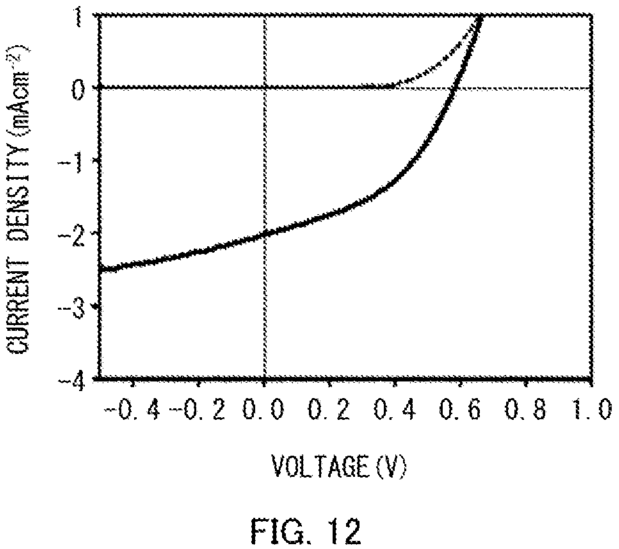
FIG. 11 is a graph showing a current density-voltage characteristic of an organic thin-film solar cell of Example 3.

The organic solar cell thus obtained was subjected to irradiation of constant light by a solar simulator (AM1.5G filter, irradiation intensity: 100 mW/cm$^2$), and a current and a voltage thus generated were measured. FIG. 11 is a graph showing a current density-voltage characteristic of the above organic solar cell.

Based on the graph shown in FIG. 11, a short-circuit current density Jsc (mA/cm$^2$), an open-circuit voltage Voc (V), and a form factor FF were worked out, with the result that Jsc=2.0 mA/cm$^2$, Voc=0.58 V, and FF=0.44. According to the formula "photoelectric conversion efficiency ($\eta$)=(Jsc×Voc×FF)/100", the photoelectric conversion efficiency of the above organic solar cell was calculated as 0.51%.

Example 4

(Evaluation of Performance of Organic Solar Cell)

An organic solar cell was produced with use of the synthesized compound 11 as the n-type organic semiconductor material. Then, evaluation was conducted on the organic solar cell thus obtained.

Used as the substrate was a glass substrate. Used as the p-type organic semiconductor material was P3HT (poly(3-hexilthiophene)). Used as the electrodes were ITO (cathode) and aluminum (anode). Used as the hole transport material was PEDOT:PSS (poly(3,4-ethylenedioxythiophene) doped with poly(4-styrene sulfonate)). Used as the electron transport material was Ca. A solution was prepared in advance by dissolving P3HT (10 mg) and the compound 11 (10 mg) in chloroform (1 mL).

First, the glass substrate on which the ITO film was patterned was subjected to ultrasonic washing with toluene, acetone, water, and isopropanol in order each for 15 minutes. Then, the glass substrate was put into a plasma cleaning machine. Then, an oxygen gas was introduced into the plasma cleaning machine, and the surface of the glass substrate was washed with generated plasma for 20 minutes. Furthermore, the glass substrate was subjected to ozone UV irradiation for 90 minutes so that the surface of the glass substrate was washed. Thereafter, a PEDOT:PSS thin film was formed on the ITO film by a spin-coating film forming device. Next, the glass substrate was subjected to annealing at 135° C. for 10 minutes. A PEDOT:PSS thin film thus formed was 30 nm. In addition, spin-coating of the above-described solution, which was prepared in advance, was carried out onto the PEDOT:PSS thin film by the spin-coating film forming device (at 3000 rpm, for 1 minute), so that an organic semiconductor layer was formed. In this manner, a lamination was obtained. Thereafter, the lamination was subjected to annealing at 120° C. for 10 minutes. Subsequently, the lamination thus obtained was placed on a mask of a small, high-vacuum vapor deposition device, and a film of Ca (20 nm) serving as the electron transport layer and an aluminum layer (80 nm) serving as the metal electrode were formed. Consequently, an organic solar cell of 3 mm square was obtained.

Figure 12:
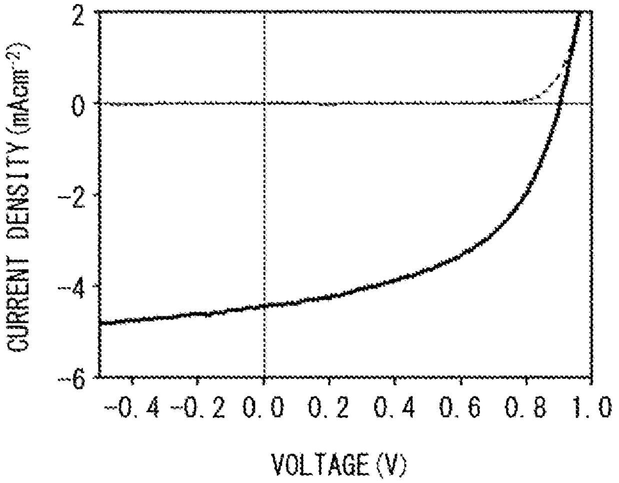
FIG. 12 is a graph showing a current density-voltage characteristic of an organic thin-film solar cell of Example 4.

The organic solar cell thus obtained was subjected to irradiation of constant light by a solar simulator (AM1.5G filter, irradiation intensity: 100 $mW/cm^2$), and a current and a voltage thus generated were measured. FIG. 12 is a graph showing a current density-voltage characteristic of the above organic solar cell.

Based on the graph shown in FIG. 12, a short-circuit current density Jsc ($mA/cm^2$), an open-circuit voltage Voc (V), and a form factor FF were worked out, with the result that Jsc=4.4 $mA/cm^2$, Voc=0.90 V, and FF=0.51. According to the formula "photoelectric conversion efficiency (f)=(Jsc×Voc×FF)/100", the photoelectric conversion efficiency of the above organic solar cell was calculated as 2.0%.

As described above, it was demonstrated that a compound in accordance with an aspect of the present invention can achieves, as an n-type organic semiconductor material, photoelectric conversion efficiency high enough to be an alternative to a fullerene derivative, for example.

INDUSTRIAL APPLICABILITY

An organic semiconductor material including a compound in accordance with an aspect of the present invention has a high photoelectric conversion efficiency and a high charge mobility, i.e., an excellent semiconductor property, and therefore is applicable to various semiconductor devices, such as photoelectric conversion elements, organic thin-film transistors (e.g., field effect transistors), and light emitting devices.

REFERENCE SIGNS LIST

1 substrate
2 organic semiconductor layer
3 insulating layer
4 gate electrode
5 source electrode
6 drain electrode
100, 110, 120, 130, 140, 150, 160 organic thin-film transistor
11 anode
12 cathode
14 photoelectric conversion layer
25 substrate
26 hole transport layer
27 electron transport layer
38 charge recombination layer

What is claimed:

1. A compound represented by a general formula (1):

(1)

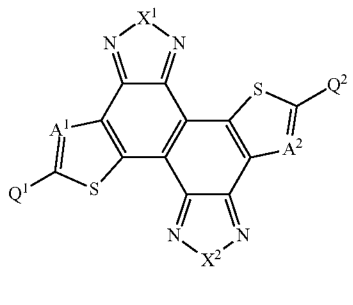

where:

in the general formula (1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

$X^1$ and $X^2$ are each independently

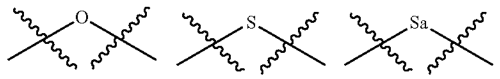

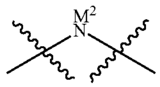

or

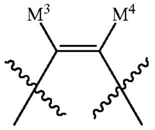

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group.

2. A compound represented by a general formula (2-1):

(2-1)

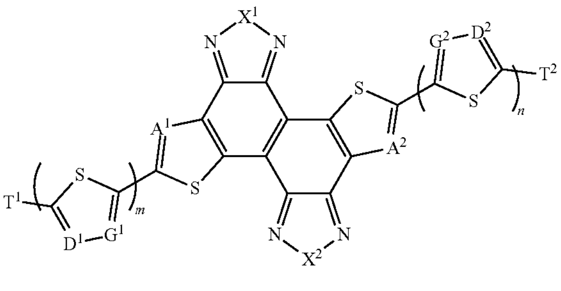

where:

in the general formula (2-1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$X^1$ and $X^2$ are each independently

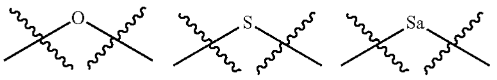

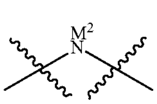

or

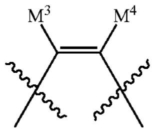

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group, $D^1$, $D^2$, $G^1$, and $G^2$ are each independently $CM^1$ or N;

m and n are each independently 0 or a natural number;

$T^1$ and $T^2$ are each independently

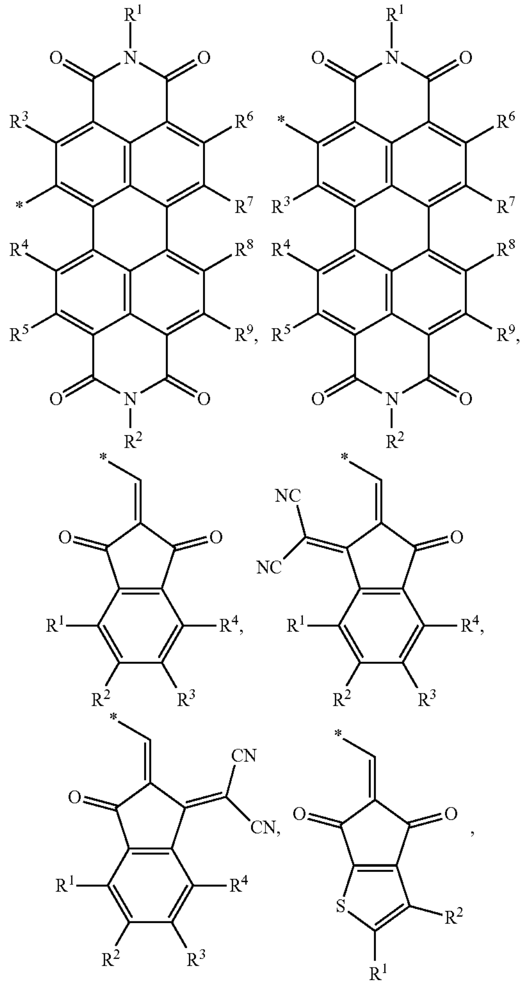

-continued
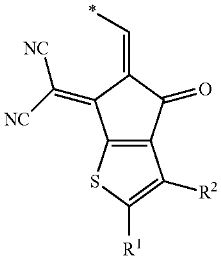
,
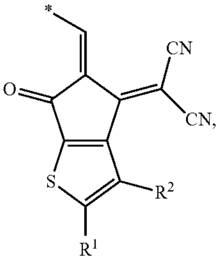
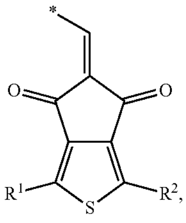
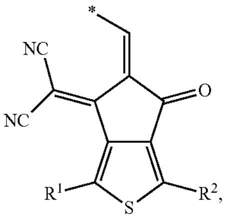
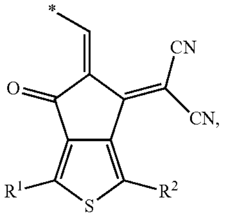
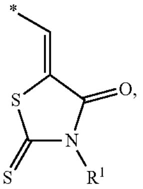
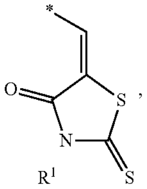
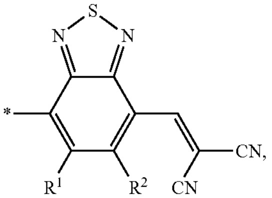
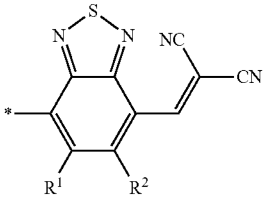
,
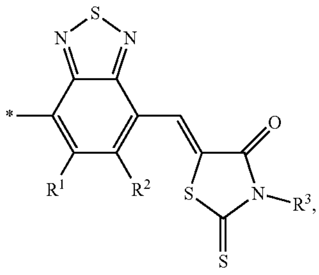
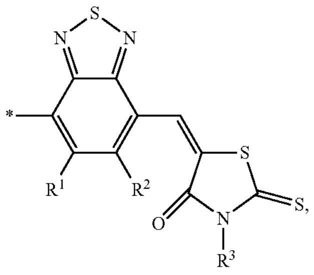
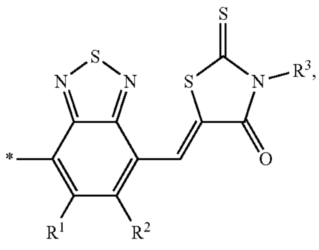
-continued
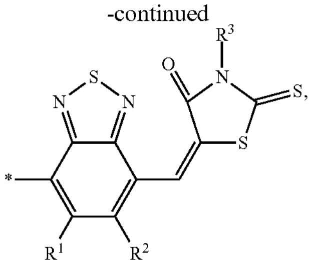
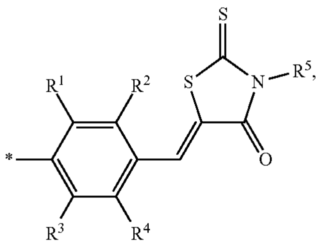
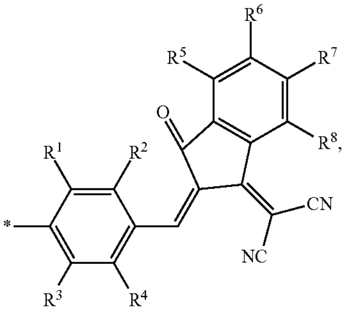
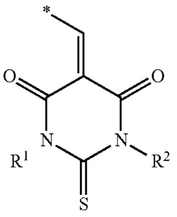
or
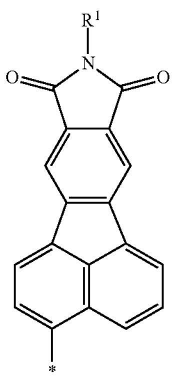
where $R^1$ to $R^9$ are each independently a hydrogen atom, a halogen atom, an alkyl group, an alkoxy group, an alkoxy carbonyl group, an alkyl carbonyl group, or an aryl group; and * represents a bond.
3. The compound as set forth in claim 2, wherein the compound is a compound represented by a general formula (2-2):

(2-2)

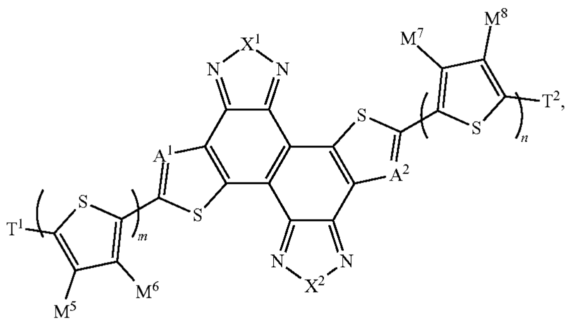

where:

in the general formula (2-2), $M^5$ to $M^8$ are each independently a hydrogen atom, a halogen atom, an alkyl group, an alkoxy group, an alkoxy carbonyl group, an alkyl carbonyl group, or an aryl group.

4. An organic semiconductor material comprising the compound recited in claim 2.

5. An organic semiconductor device comprising the organic semiconductor material recited in claim 4.

6. A method for producing a compound represented by a general formula (1):

(1)

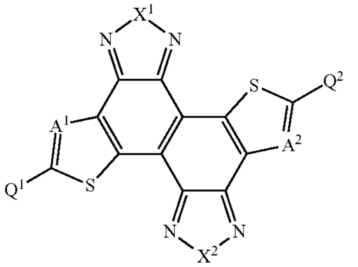

where:

in the general formula (1), $A^1$ and $A^2$ are each independently $CM^1$ or N, and $M^1$ is a hydrogen atom, a halogen atom, an alkyl group optionally substituted with Z, a cyano group, an alkoxy group optionally substituted with Z, an alkylthio group optionally substituted with Z, an alkoxy carbonyl group optionally substituted with Z, an alkyl carbonyl group optionally substituted with Z, or an aryl group optionally substituted with Z;

$Q^1$ and $Q^2$ are each independently a hydrogen atom, a halogen atom, an aryl group optionally substituted with Z, a heterocyclic group optionally substituted with Z, a formyl group, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group;

$X^1$ and $X^2$ are each independently

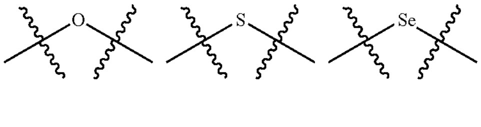

-continued

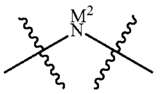

or

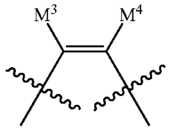

where:

$M^2$ to $M^4$ are each independently a hydrogen atom, a halogen atom, an alkyl group optionally substituted with Z, an alkoxy group optionally substituted with Z, an alkyl ester group optionally substituted with Z, an alkoxy carbonyl group optionally substituted with Z, an alkyl amino carbonyl group optionally substituted with Z, an acyl group optionally substituted with Z, an amino group optionally substituted with Z, an acylamino group optionally substituted with Z, an aryloxy group optionally substituted with Z, an aryloxycarbonyl group optionally substituted with Z, an acyloxy group optionally substituted with Z, an alkoxycarbonylamino group optionally substituted with Z, an aryloxycarbonylamino group optionally substituted with Z, an alkylthio group optionally substituted with Z, an arylthio group optionally substituted with Z, an aryl group optionally substituted with Z, or a heterocyclic group optionally substituted with Z, and $M^3$ and $M^4$ optionally form a ring together; and Z is an alkyl group, a cycloalkyl group, an alkenyl group, an alkynyl group, an aryl group, an acyl group, an alkoxy carbonyl group, an amino group, an alkoxy group, a cycloalkyloxy group, an aryloxy group, an aryloxycarbonyl group, an acyloxy group, an acylamino group, an alkoxycarbonylamino group, an aryloxycarbonylamino group, a sulfonyl amino group, a sulfamoyl group, a carbamoyl group, an alkylthio group, an arylthio group, a silyl group, a sulfonyl group, a sulfinyl group, an ureide group, a phosphoric acid amido group, a halogen atom, a hydroxyl group, a mercapto group, a cyano group, a sulfo group, a carboxyl group, a nitro group, a hydroxamic acid group, a sulfino group, a hydrazino group, or an imino group, said method being any of the following method (1), (2), (3), (4), (5), or (6):

the method (1) including:

(i) a step 1a of causing a compound represented by a general formula (A5) to react with trialkylsilylacetylene to produce a compound represented by a general formula (A6):

(A5)

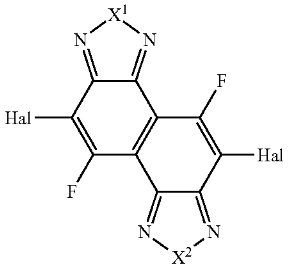

where, in the general formula (A5), each Hal is independently a halogen atom; and $X^1$ and $X^2$ are the same as those defined above, (A6)

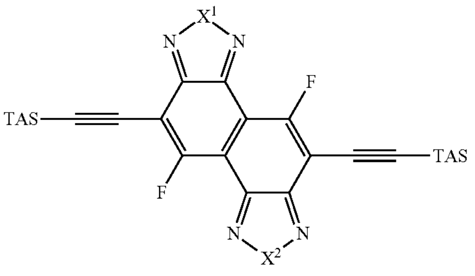

where, in the general formula (A6); TAS represents a trialkylsilyl group; and $X^1$ and $X^2$ are the same as those defined above;

(ii) a step 2a of causing the compound represented by the general formula (A6) obtained in the step 1a to react with a sulphurizing agent to produce a compound represented by a general formula (A7):

(A7)

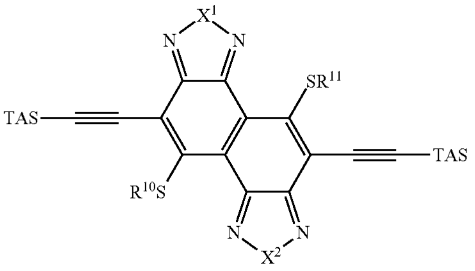

where, in the general formula (A7), TAS, $X^1$, and $X^2$ are the same as those defined above; and $R^{10}$ and $R^{11}$ are each independently an alkyl group optionally substituted with Z, and Z is the same as that defined above; and (iii) a step 3a of causing the compound represented by the general formula (A7) obtained in the step 2a to react with a halogenating agent to produce a compound represented by a general formula (1-1):

(1-1)

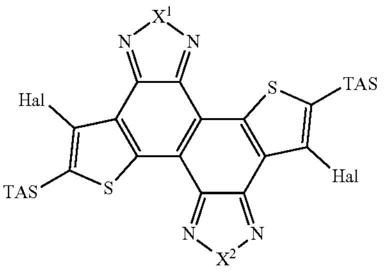

where, in the general formula (1-1), TAS, Hal, $X^1$, and $X^2$ are the same as those defined above, the general formula (1-1) being encompassed in the general formula (1);

the method (2) including:

a step 4a of causing the compound represented by the general formula (1-1) obtained in the step 3a to react with a boron compound to produce a compound represented by a general formula (1-2):

(1-2)

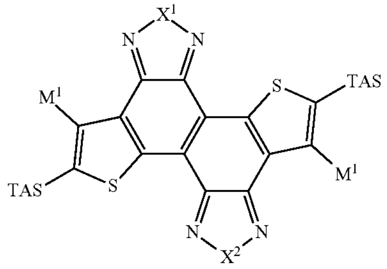

where, in the general formula (1-2), TAS, $M^1$, $X^1$, and $X^2$ are the same as those defined above, the general formula (1-2) being encompassed in the general formula (1);

the method (3) including:

a step 5a of causing the compound represented by the general formula (1-2) obtained in the step 4a to react with a halogenating agent to produce a compound represented by a general formula (1-3):

(1-3)

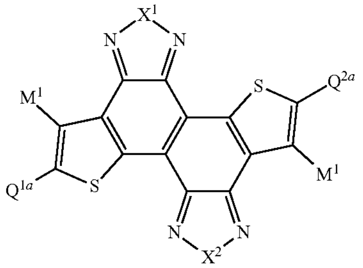

where, in the general formula (1-3), $M^1$, $X^1$, and $X^2$ are the same as those defined above; and $Q^{1a}$ and $Q^{2a}$ are each independently a halogen atom, the general formula (1-3) being encompassed in the general formula (1);

the method (4) including:

a step 6a of causing the compound represented by the general formula (1-3) to react with a boron compound or a tin compound to produce a compound represented by a general formula (1-4):

(1-4)

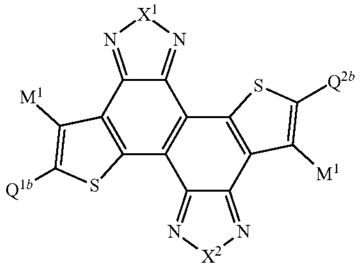

where, in the general formula (1-4), $M^1$, $X^1$, and $X^2$ are the same as those defined above; and $Q^{1b}$ and $Q^{2b}$ are each independently a hydrogen atom, an aryl group optionally substituted with Z, a heterocyclic group optionally substituted with Z, a boronic acid group, a boronic acid ester group, a boronic acid diaminonaphthalene amide group, an N-methyliminodiacetic acid boronate ester group, a trifluoroborate salt group, a triolborate salt group, a trialkylsilyl group, or a trialkylstannyl group, the general formula (1-4) being encompassed in the general formula (1);

the method (5) including:

formylating the compound represented by the general formula (1-4) to produce a compound represented by a general formula (1-5):

(1-5)

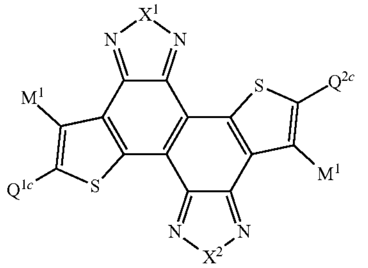

where, in the general formula (1-5), $M^1$, $X^1$, and $X^2$ are the same as those defined above; and $Q^{1c}$ and $Q^{2c}$ are each independently a formyl group;

the method (6) including:

(i) a step 1b of causing a compound represented by a general formula (A9) to react with a halogenating agent to produce a compound represented by a general formula (A10):

(A9)

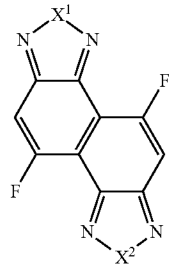

where, in the general formula (A9), $X^1$ and $X^2$ are the same as those defined above;

(A10)

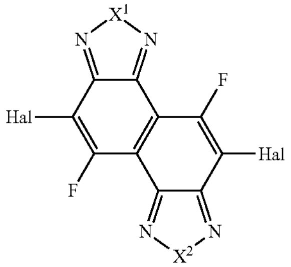

where, in the general formula (A10), $X^1$, $X^2$, and Hal are the same as those defined above;

(ii) a step 2b of causing the compound represented by the general formula (A10) obtained in the step 1b to react with an aminating agent to produce a compound represented by a general formula (A11):

(A11)

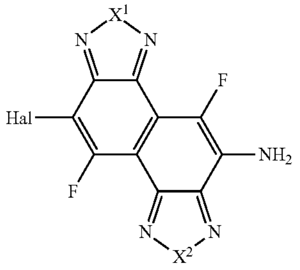

where, in the general formula (A11), $X^1$ and $X^2$ are the same as those defined above;

(iii) a step 3b of causing the compound represented by the general formula (A11) obtained in the step 2b to react with a compound represented by $Q^1$-$CO_2Cl$, where $Q^1$ is the same as that defined above, and a compound represented by $Q^2$-$CO_2Cl$, where $Q^2$ is the same as that defined above, to produce a compound represented by a general formula (A12):

(A12)

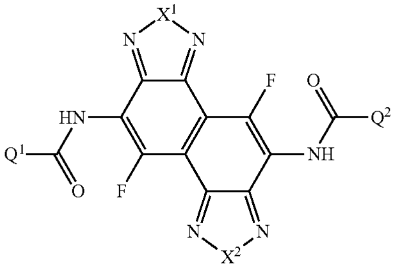

where, in the general formula (A12), $X^1$, $X^2$, $Q^1$, and $Q^2$ are the same as those defined above; and (iv) a step 4b of causing the compound represented by the general formula (A12) obtained in the step 3b to react with a sulphurizing agent to produce a compound represented by a general formula (1-6):

(1-6)

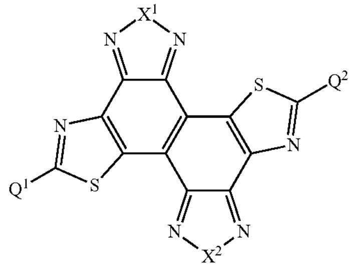

where, in the general formula (1-6), $X^1$, $X^2$, $Q^1$, and $Q^2$ are the same as those defined above, the general formula (1-6) being encompassed in the general formula (1).

7. A method for producing a compound represented by the general formula (2-1) recited in claim 2, said method comprising:

introducing, as $Q^1$ and $Q^2$ in a compound represented by the general formula (1) recited in claim 1, a group represented by a formula below

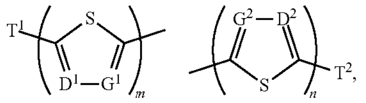

where $T^1$ and $T^2$ are the same as those defined in claim 2, $D^1$ and $G^1$ are the same as those in general formula (iv) below, $D^2$ and $G^2$ are the same as those in general formula (v) below, and m and n are the same as those defined in claim 2, the step of introducing comprising the following steps (a) to (c):

(a) reacting the compound represented by the general formula (1) with a compound represented by general formula (iv)

(iv)

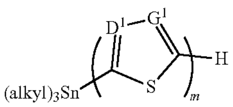

where, in the general formula (iv), $D^1$ and $G^1$ are each independently $CM^1$ or N, $M^1$ is a hydrogen atom, a halogen atom, a cyano group, an alkyl group that may be substituted with Z, or an alkoxy group that may be substituted with Z, and Z is as defined in claim 1, and a compound represented by general formula (v)

(v)

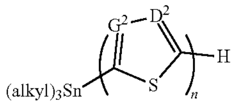

where, in the general formula (v), $D^2$ and $G^2$ are each independently $CM^1$ or N, $M^1$ is a hydrogen atom, a halogen atom, a cyano group, an alkyl group that may be substituted with Z, or an alkoxy group that may be substituted with Z, and Z is as defined in claim 1 to produce a compound represented by general formula (A13)

(A13)

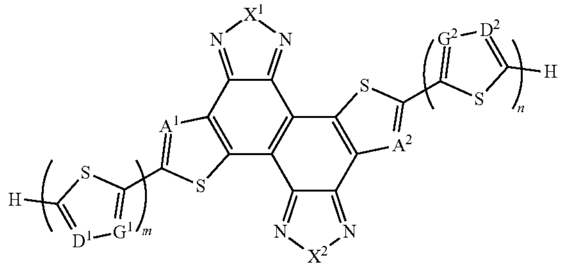

where, in the general formula (A13), $A^1$, $A^2$, $X^1$, $X^2$, m, and n are the same as those defined in claim 2, and $D^1$, $G^1$, $D^2$, and $G^2$ are as defined above;

(b) reacting the compound represented by the general formula (A13) with a formylating reagent to produce a compound represented by general formula (A14)

(A14)

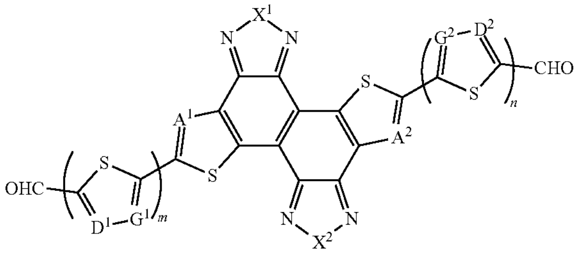

where, in the general formula (A14), $A^1$, $A^2$, $X^1$, $X^2$, m, n, $D^1$, $G^1$, $D^2$ and $G^2$ are as defined above; and (c) producing the compound represented by the general formula (2-1) from the compound represented by the general formula (A14).

* * * * *

UNITED STATES PATENT AND TRADEMARK OFFICE

CERTIFICATE OF CORRECTION

PATENT NO. : 12,331,062 B2
APPLICATION NO. : 17/288949
DATED : June 17, 2025
INVENTOR(S) : Yutaka Ie et al.

It is certified that error appears in the above-identified patent and that said Letters Patent is hereby corrected as shown below:

In the Claims

In Column 76, Claim 1, Lines 43-44, please replace " 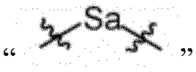 " with -- 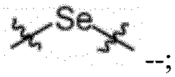 --;

In Column 77, Claim 2, Lines 49-51, please replace " 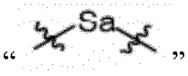 " with -- 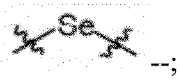 --;

In Column 79, Claim 2, Lines 21-29, please replace " 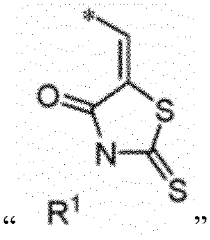 " with -- 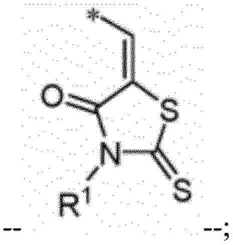 --;

In Column 80, Claim 2, Lines 29-37, please replace " 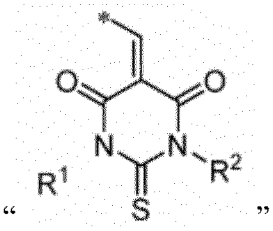 " with -- 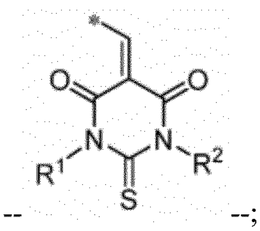 --;

Signed and Sealed this
Twelfth Day of August, 2025

Coke Morgan Stewart
*Acting Director of the United States Patent and Trademark Office*

In Column 86, Claim 6, Lines 5-15, please replace " 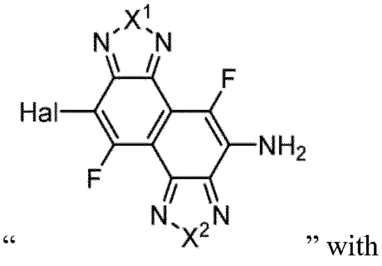 " with
-- 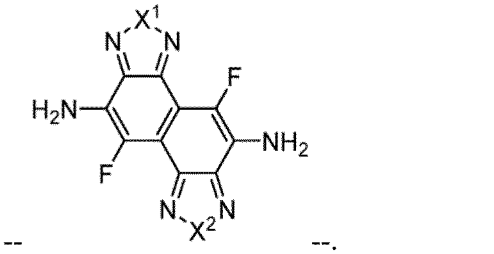 --.